(12) United States Patent
Henry et al.

(10) Patent No.: US 9,758,558 B2
(45) Date of Patent: Sep. 12, 2017

(54) WHEY PROTEIN ISOLATE HYDROGELS AND THEIR USES

(75) Inventors: James E. Henry, Baton Rouge, LA (US); Mia Dvora, Raleigh, NC (US)

(73) Assignee: Board of Supervisors of Louisiana State University And Agriculture and Mechanical College, Baton Rouge, LA (US)

( * ) Notice: Subject to any disclaimer, the term of this patent is extended or adjusted under 35 U.S.C. 154(b) by 774 days.

(21) Appl. No.: 13/637,699

(22) PCT Filed: Apr. 1, 2011

(86) PCT No.: PCT/US2011/030903
§ 371 (c)(1),
(2), (4) Date: Dec. 11, 2012

(87) PCT Pub. No.: WO2011/123760
PCT Pub. Date: Oct. 6, 2011

(65) Prior Publication Data
US 2013/0101548 A1 Apr. 25, 2013

Related U.S. Application Data

(60) Provisional application No. 61/320,010, filed on Apr. 1, 2010.

(51) Int. Cl.
| | |
|---|---|
| A01N 25/08 | (2006.01) |
| A01K 97/04 | (2006.01) |
| A01K 85/00 | (2006.01) |
| C07K 14/47 | (2006.01) |
| A23J 3/08 | (2006.01) |
| A61L 27/26 | (2006.01) |
| A61L 27/52 | (2006.01) |
| A61L 27/54 | (2006.01) |
| A61L 27/58 | (2006.01) |
| D01D 5/00 | (2006.01) |
| D01F 4/00 | (2006.01) |
| A23K 20/147 | (2016.01) |
| A23K 50/80 | (2016.01) |

(52) U.S. Cl.
CPC ........ *C07K 14/4717* (2013.01); *A01K 97/045* (2013.01); *A23J 3/08* (2013.01); *A23K 20/147* (2016.05); *A23K 50/80* (2016.05); *A61L 27/26* (2013.01); *A61L 27/52* (2013.01); *A61L 27/54* (2013.01); *A61L 27/58* (2013.01); *D01D 5/0038* (2013.01); *D01F 4/00* (2013.01); *A61L 2300/414* (2013.01); *A61L 2430/02* (2013.01); *A61L 2430/06* (2013.01)

(58) Field of Classification Search
None
See application file for complete search history.

(56) References Cited

U.S. PATENT DOCUMENTS

| | | | |
|---|---|---|---|
| 6,337,198 B1 | 1/2002 | Levene et al. | 435/174 |
| 6,753,004 B2 | 6/2004 | Ollis et al. | 424/410 |
| 7,556,800 B2 | 7/2009 | Etayo Garralda et al. | 424/84 |
| 7,615,593 B2 | 11/2009 | Kao et al. | 525/54.1 |
| 2002/0107292 A1 | 8/2002 | Bortlik et al. | 514/773 |
| 2006/0008445 A1 | 1/2006 | Garralda et al. | 424/84 |
| 2006/0233850 A1 | 10/2006 | Michal | 424/422 |
| 2006/0240076 A1 | 10/2006 | Henson et al. | 424/439 |
| 2008/0131509 A1 | 6/2008 | Hossainy et al. | 424/484 |
| 2008/0274156 A1 | 11/2008 | Nurcombe et al. | 424/423 |
| 2008/0311172 A1 | 12/2008 | Schapira et al. | 424/423 |
| 2009/0226530 A1* | 9/2009 | Lassner | A61K 9/1605 514/1.1 |
| 2009/0232876 A1 | 9/2009 | Montes et al. | 424/447 |

FOREIGN PATENT DOCUMENTS

JP  2004236600 A  *  8/2004

OTHER PUBLICATIONS

Gunasekaran et al. Use of whey proteins for encapsulation and controlled delivery applications. Journal of Food Engineering. 2007; 83(1): 31-40.*
Pareta et al. A novel method for the preparation of starch films and coatings. Carbohydrate Polymers, 2006; 63(3): 425-431.*
Euston et al. Food Hydrocolloids, 2000; 14:155-161.*
Munialo et al. Food Hydrocolloids, 2016; 52:707-720.*
Chang, B.S. and Hershenson, S. 2002. Practical approaches to protein formulation development. in "Rationale Design of stable protein formulations—theory and practice" (J.F. Carpenter and M.C. Manning eds.) Kluwer Academic/Plenum publishers, New York, pp. 1-25.*
Euston et al. Aggregation kinetics of heated whey protein stabilzed emulsions. Food Hydrocolloids, 2000; 14:155-161.*

(Continued)

*Primary Examiner* — Vanessa L Ford
*Assistant Examiner* — Sandra Dillahunt
(74) *Attorney, Agent, or Firm* — John H. Runnels; Bonnie J. Davis

(57) ABSTRACT

A biodegradable hydrogel has been made based on high concentrations of whey protein isolate (WPI). WPI gels of different compositions were fabricated by thermally inducing gelation of high-concentration suspensions of protein, and characterized for compressive strength and modulus, hydration swelling and drying properties, mechanical behavior change due to polysaccharide additives, and intrinsic pore network structure. The gels were shown to be compatible with bone cells and could be used as bone tissue scaffolds. In addition, WPI fibers were produced by electrospinning. Several additives could be incorporated into the WPI gels, including structural additives, growth factors, amino acids, etc. The WPI hydrogels can be made with glycerol to increase flexibility and stability. The hydrogels could be used for tissue regeneration, food protection, controlled-release applications (including drug encapsulation, dietary supplement release, attractant release in lures, nutrient release to plants (fertilizers), column packing for compound separation, and membrane development.

13 Claims, 36 Drawing Sheets

(56) References Cited

OTHER PUBLICATIONS

Munialo et al.The effect of polysaccharides on the ability of whey protein gels to either store or dissipate energy upn mechanical defomration. Food Hydrocolloids, 2016; 52:707-720.*

ASTM Standard D 638-97, Standard test method for tensile property of plastics, Annual Book of ASTM Standards. West Conshonocken, PA, USA: ASTM International; 1998; pp. 46-58 (1998).

Bryant, C.M. et al., "Influence of xanthan gum on physical characteristics of heat-denatured whey protein solutions and gels," Food Hydrocolloids, vol. 14, pp. 383-390 (2000).

Cao, X. et al., "New nanocomposite materials reinforced with flax cellulose nanocrystals in waterborne polyurethane," Biomacromolecules, vol. 8, pp. 899-904 (2007).

Caussin, F. et al., "Mineral modulation of thermal aggregation and gelation of whey proteins: from beta-lactoglobulin model system to whey protein isolate," Lait, vol. 83, pp. 1-12 (2003).

Chrysina, E.D. et al., "Crystal structures of apo- and holo-bovine alpha-lactalbumin at 2.2—A resolution reveal an effect of calcium on inter-lobe interactions," Journal of Biological Chemistry, vol. 275, pp. 37021-37029 (2000).

Chung, H.J. et al., "Surface engineered and drug releasing prefabricated scaffolds for tissue engineering," Advanced Drug Delivery Reviews, vol. 59, pp. 249-262 (2007).

Drury, J.L. et al., "Hydrogels for tissue engineering: scaffold design variables and applications," Biomaterials, vol. 24, pp. 4337-4351 (2003).

Dvora, Mia et al., "Altering the Mechanical Properties of Protein-Based Solids", 2006 AIChE (American Institute of Chemical Engineers) Annual Meeting, San Francisco, California (Nov. 12-17, 2007).

Dvora, Mia et al., "Characterization of whey protein isolate sol-gels as scaffolds for bone regeneration," an abstract and presentation given to the 2007 AIChE Annual Meeting, Salt Lake City, Utah (Nov. 4-9, 2007).

Dvora, Mia, "Designing a whey protein based material as a scaffold for bone regeneration," a thesis submitted to Louisiana State University (Aug. 2010).

Dvora, Mia et al., "Design of a whey protein isolate composite as a bone regeneration scaffold: optimization of mechanical properties," an abstract and poster given at the 2008 International Symposium on Polymer Physics, Xiamen, China (Jun. 8-12, 2008).

Dvora, Mia et al., "Optimization of preosteoblast proliferation rate on whey protein gels for bone tissue regeneration," an abstract and presentation given to the 2008 AIChE Annual Meeting, Philadelphia, PA (Nov. 16-21, 2008).

Dvora, Mia et al., "Tuning the Microarchitecture and Biodegradability of Whey Protein Isolate Composite Scaffolds for Bone Tissue Regeneration" in American Institute of Chemical Engineers, 2009 Annual Meeting, Nashville, TN, AICHE, p. 686f (Nov. 13, 2009).

Dvora, Mia et al., "Whey protein isolate sol-gel as a scaffold for bone tissue regeneration: investigating the osteoprogenitor response," abstracts and posters given at the 2009 American Chemical Society Annual Meeting, Washington, D.C. (Aug. 16-20, 2009).

Dvora, Mia et al., "X-Ray tomography for analysis of biological scaffold materials," an abstract and presentation given at the 2007 AIChE (American Institute of Chemical Engineers) Annual Meeting, Salt Lake City, Utah (Nov. 4-9, 2007).

Foegeding, E.A. et al., "Advances in modifying and understanding whey protein functionality," Trends in Food Science & Technology, vol. 13, pp. 151-159 (2002).

Fox, P.F., "Milk proteins as food ingredients," International Journal of Dairy Technology, vol. 54, pp. 41-55 (2001).

Goldstein, A.S. et al., "Effect of convection on osteoblastic cell growth and function in biodegradable polymer foam scaffolds," Biomaterials, vol. 22, pp. 1279-1288 (2001).

Goldstein, S.A. et al., "The mechanical properties of human tibial trabecular bone as a function of metaphyseal location," Journal of Biomechanics., vol. 16, pp. 965-969 (1983).

Grunert, M. et al., "Nanocomposites of cellulose acetate butyrate reinforced with cellulose nanocrystals," Journal of Polymers and the Environment, vol. 10, pp. 27-30 (2002).

Hussain, F. et al., Review article: "Polymer-matrix nanocomposites, processing, manufacturing, and application: An overview," Journal of Composite Materials, vol. 40, pp. 1511-1575 (2006).

Hutmacher, D.W., "Scaffolds in tissue engineering bone and cartilage," Biomaterials, vol. 21, pp. 2529-2543 (2000).

Ju, Z.Y. et al., "Aggregation induced by calcium chloride and subsequent thermal gelation of whey protein isolate," J. Dairy Sci, vol. 81, pp. 925-931 (1998).

Ju, Z.Y. et al., "Gelation of pH-aggregated whey protein isolate solution induced by heat, protease, calcium salt, and acidulant," Journal of Agricultural and Food Chemistry, vol. 46, No. 5, pp. 1830-1835 (1998).

Ju, Z.Y. et al., "Properties of gels induced by heat, protease, calcium salt, and acidulant from calcium ion-aggregated whey protein isolate," Journal of Dairy Science, vol. 81, pp. 1236-1243 (1998).

Ju, Z.Y. et al., "Thermal properties of whey protein aggregates," J Dairy Sci, vol. 82, pp. 1882-1889 (1999).

Kanungo, B.P. et al., "Characterization of mineralized collagen-glycosaminoglycan scaffolds for bone regeneration," Acta Biomaterialia, vol. 4, pp. 490-503 (2008).

Kato, K. et al., "Milk basic protein enhances the bone strength in ovariectomized rats," Journal of Food Biochemistry, vol. 24, pp. 467-476 (2000).

Kinekawa, Y-I. et al., "Effects of salts on the properties of sols and gels prepared from whey protein isolate and process whey protein," Journal of Dairy Science, vol. 81, pp. 1532-1544 (1998).

Kinsella, J.E. et al., "Proteins in whey: chemical, physical, and functional properties," Advances in Food and Nutrition Research, vol. 33, pp. 343-438 (1989).

Kuhn, P.R. et al., "Mineral salt effects on whey-protein gelation," Journal of Agricultural and Food Chemistry, vol. 39, pp. 1013-1016 (1991).

Kuwata, K. et al., "Solution structure and dynamics of bovine beta-lactoglobulin A," Protein Science, vol. 8 , pp. 2541-2545 (1999).

Laurencin, C.T. et al., "Tissue engineered bone-regeneration using degradable polymers: The formation of mineralized matrices," Bone, vol. 19, pp. S93-S99 (1996).

Lee, S.H. et al., Matrices and scaffolds for delivery of bioactive molecules in bone and cartilage tissue engineering. Advanced Drug Delivery Reviews, vol. 59, pp. 339-359 (2007).

Liu, C. et al., "Design and development of three-dimensional scaffolds for tissue engineering," Chem Eng Res Design, vol. 85, pp. 1051-1064 (2007).

Marangoni, A.G. et al., "On the structure of particulate gels the case of salt-induced cold gelation of heat-denatured whey protein isolate," Food Hydrocolloids, vol. 14, pp. 61-74 (2000).

Mockaitis, G. et al., "Anaerobic whey treatment by a stirred sequencing batch reactor (ASBR): effects of organic loading and supplemented alkalinity," Journal of Environmental Management, vol. 79, pp. 198-206 (2006).

Mulvihill, D.M. et al., "Gelation of beta-lactoglobulin—effects of sodium-chloride and calcium-chloride on the rheological and structural properties of gels," Journal of Food Science, vol. 53, pp. 231-236 (1988).

Murugan, R. et al., "Nano-featured scaffolds for tissue engineering: A review of spinning methodologies," Tissue Engineering, vol. 12, pp. 435-447 (2006).

Ostojic, S. et al., "Processing of whey from dairy industry waste," Environmental Chemistry Letters, vol. 3, pp. 29-32 (2005).

Patocka, G. et al., "Rheological behaviour of dairy products as affected by soluble whey protein isolate," International Dairy Journal, vol. 16, pp. 399-405 (2006).

Rouabhia, M. et al., "In vivo evaluation of whey protein-based biofilms as scaffolds for cutaneous cell cultures and biomedical applications," Biomedical Materials, vol. 2 , pp. S38-S44 (2007).

Shin, H. et al., "Biomimetic materials for tissue engineering," Biomaterials. 2003;24:4353-64 (2003).

(56) References Cited

OTHER PUBLICATIONS

Takada, Y. et al., "Whey protein stimulates the proliferation and differentiation of osteoblastic MC3T3-E1 cells," Biochemical and Biophysical Research Communications, vol. 223, pp. 445-449 (1996).

Takada, Y. et al., "Whey protein suppresses the osteoclast-mediated bone resorption and osteoclast cell formation," International Dairy Journal, vol. 7, pp. 821-825 (1997).

Teo, J.Y. et al., "Novel solvent stable micro-porous membrane made of whey protein isolate gel," Journal of Membrane Science, vol. 192, pp. 71-82 (2001).

Uenishi, K. et al., "Milk basic protein increases bone mineral density and improves bone metabolism in healthy young women," Osteoporosis International, vol. 18, pp. 385-390 (2007).

van den Berg, L. et al., "Breakdown properties and sensory perception of whey proteins/polysaccharide mixed gels as a function of microstructure," Food Hydrocolloids, vol. 21, pp. 961-976 (2007); published as Ch.4 of "Texture of Food Gels Explained by Combining Structure and Large Deformation Properties," pp. 49-79 (2008).

Vardhanabhuti, B. et al., "Rheological properties and characterization of polymerized whey protein isolates," Journal of Agricultural and Food Chemistry, vol. 47, pp. 3649-3655 (1999).

Walzem, R.L. et al., "Whey components: Millennia of evolution create functionalities for mammalian nutrition: What we know and what we may be overlooking," Critical Reviews in Food Science & Nutrition, vol. 42, pp. 353-375 (2002).

Yaszemski, M.J. et al., In vitro degradation of a poly(propylene fumarate)-based composite material. Biomaterials, vol. 17, pp. 2127-2130 (1996).

\* cited by examiner

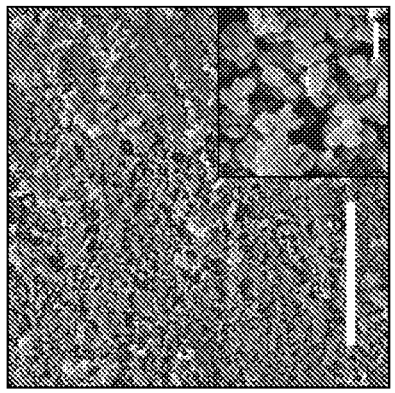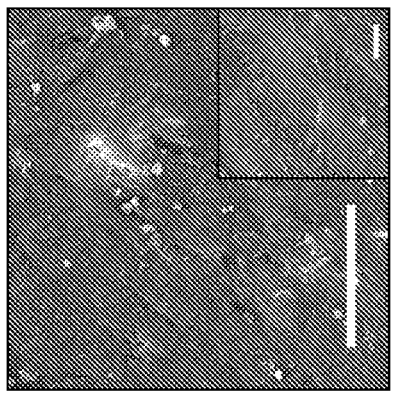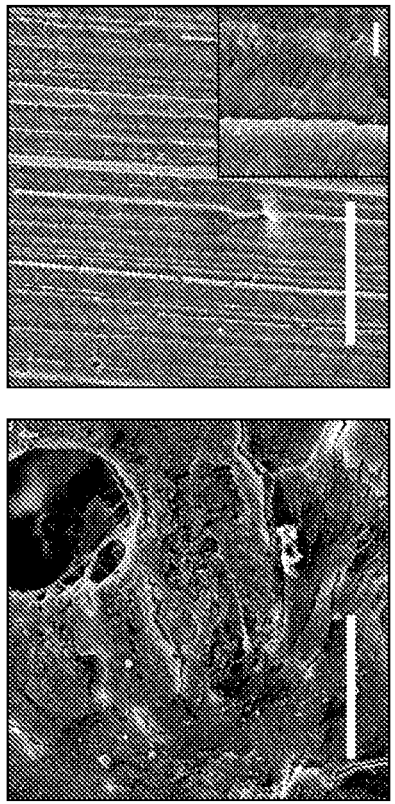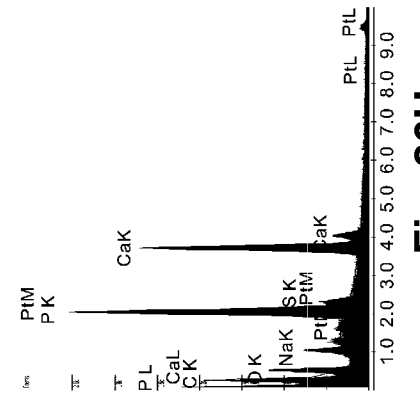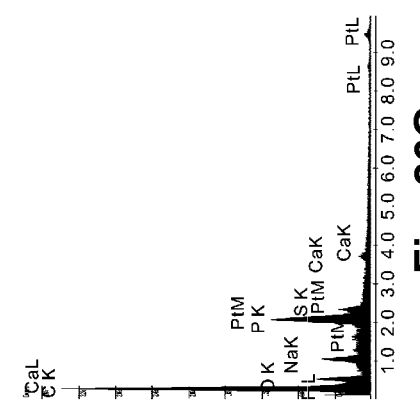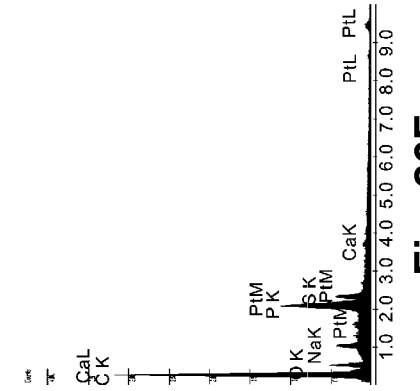
Fig. 26A Fig. 26B Fig. 26C Fig. 26D
Fig. 26E Fig. 26F Fig. 26G Fig. 26H

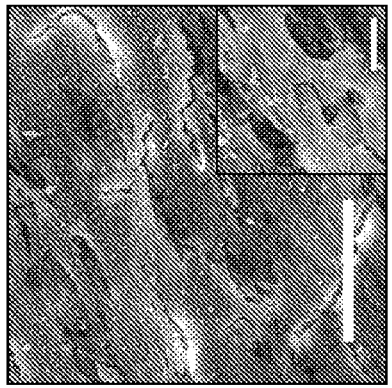 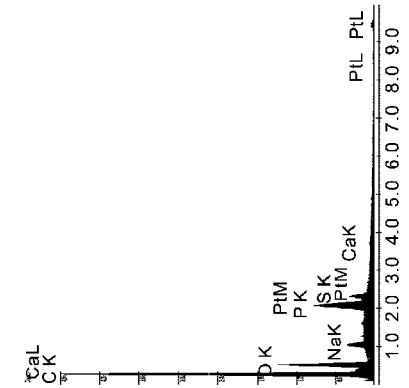
Fig. 27A  Fig. 27B  Fig. 27C  Fig. 27D
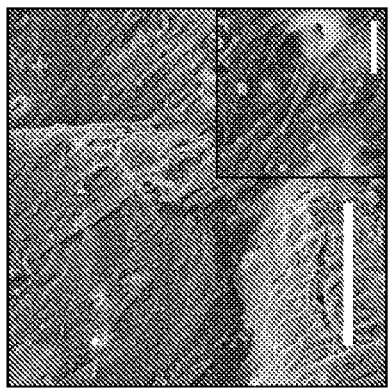 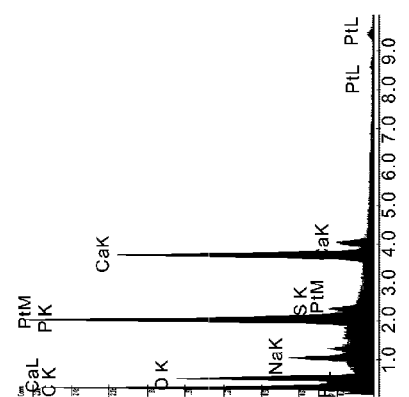
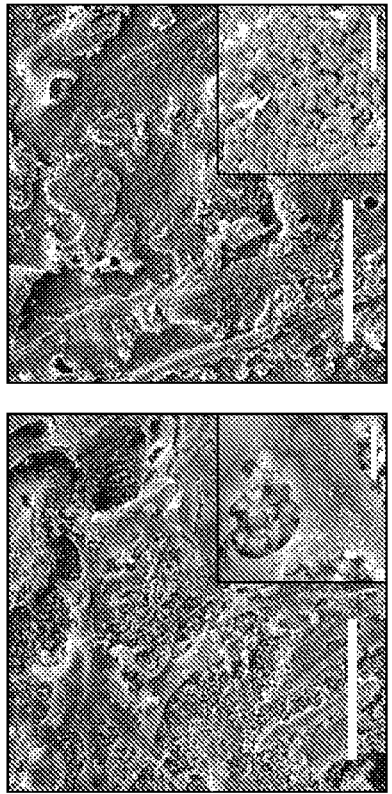 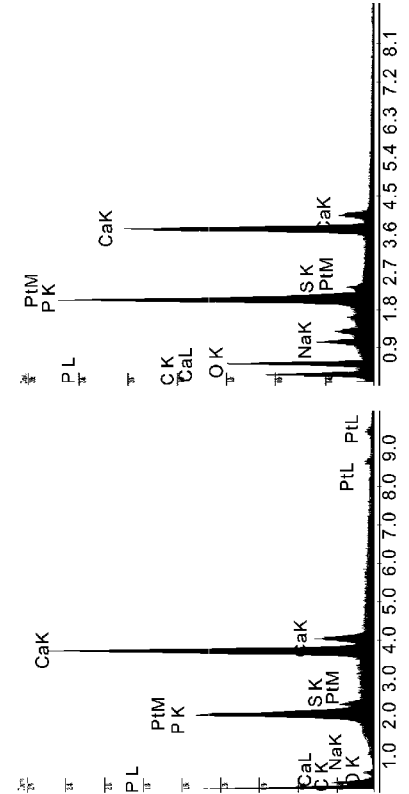
Fig. 27E  Fig. 27F  Fig. 27G  Fig. 27H

WHEY PROTEIN ISOLATE HYDROGELS AND THEIR USES

This is the United States national stage of international application PCT/US2011/030903, international filing date Apr. 1, 2011,which claims the benefit of the filing date of provisional U.S. application Ser. No. 61,320,010, filed Apr. 1, 2010, under 35 U.S.C. §119(e).

TECHNICAL FIELD

This invention pertains to biodegradable and biocompatible hydrogels or nanofibrous matrices using whey protein isolate, and the use of such gels or matrices for tissue engineering, for DNA or drug controlled-delivery, for fishing lures, and for other known uses for such gels or matrices.

BACKGROUND ART

The field of tissue engineering and regenerative medicine is making strides in succeeding the field of organ and tissue replacement for the improved safety and affordability of medical care and the increase of patient lifespan and improvement of quality of life. In the midst of advancement in the field, many hurdles remain in the path to implementation of the techniques developed for regenerating bone following massive tissue loss caused by injury or disease or regenerating other body tissues, e.g., skin. It is generally accepted that a compressive strength of 5 MPa and an elastic modulus of 50 MPa make a material suitable as a scaffold for bone regeneration [1-2].

Several polymers—both natural and synthetic—are of great interest in the tissue regeneration field and are being investigated for use as tissue engineering scaffolds [3]. This class of materials is so diverse and versatile that it can be made suitable for many applications. However, finding an ideal material has proven to be a challenge. The approach in many applications of engineered tissue is to introduce a 3D polymeric or ceramic scaffold seeded with cells into a defect site, where the scaffold provides structure, essential nutrient, and growth factors to the cells proliferating and differentiating in the defect site. [4]. While it provides a temporary template for the newly formed tissue, it is resorbed harmlessly by the body. When the scaffold is intended for bone regeneration, achieving the proper mechanical characteristics, namely the strength and stiffness of the support, becomes integral to its success [5].

One promising biopolymer is collagen, which is a key component of the extracellular matrix produced by differentiated osteoblasts during bone formation [3]. It has shown great potential for other tissue engineering applications, or in composites of other materials, but by itself lacks the compressive strength to be applied to bone regeneration [6]. Furthermore, at more than $150/g, collagen is quite costly and its use in a large implant would likely be prohibitively expensive for the average patient. Other popular natural scaffolds include fibrin and hyaluronic acid hydrogels [7], which possess similar limitations. In addition other additives have been proposed for scaffolds and other ways to generate the scaffold, including electrospinning [39-42].

Whey Protein

As an important staple in the food industry, whey protein and its components have been subjected to in-depth characterization and study, though primarily as they relate to food science and engineering [8-9]. In various journals information can be found concerning the rheological properties of whey protein solutions of less than 10% WP [10], the onset of gelation of protein solutions below 20% [11], and extensive information on properties such as flavor, foaming, texture, film properties, and the like [12]. Numerous studies have determined the correlation between protein concentration and mechanical and rheological properties of whey protein isolate gels using a variety of conditions, fabrication methods, and gel compositions. These studies have used protein concentrations equal to or lower than about 20% [27-29, 43, 44]. A micro-porous membrane was developed using an acidic mixture of whey protein isolate in concentrations from 30-40%, 0.015M-0.1M calcium chloride, and optionally a surfactant. The mixture was adjusted to pH 6.15 and centrifuged to remove the gases before heating to 120° C. on a baking sheet [21].

Bovine whey protein has been shown to promote the growth and differentiation of osteoblasts in different species [13-16] and to suppress osteoclast activity, preventing bone resorption [17]. Whey protein isolate is extremely inexpensive and abundantly available. Recent years have shown an increased drive to develop uses for whey protein in order to increase the value of milk products and reduce disposal costs and organic pollution [18-19]. Whey is considered a byproduct in cheese production, and the cheese manufacture industry pays for its disposal, as whey constitutes 80-90% of the original milk volume [20]. One study investigated the use of whey protein gels as non-fouling filtration membranes [21].

The components of the WPI protein mixture are well characterized [9] both in structure and in sequence [22-23], and its gelling properties have been extensively studied and are favorable for the application. Information on whey protein solutions and gels at low concentrations is known primarily as it relates to food science [24-29]. Whey protein is heat sensitive so thermal denaturing can be done at low temperatures, making thermal curing of protein solutions straight-forward. Added calcium ions participate in cross-linking, hydrogen bonding, and hydrophobic interactions on cooling, thus tightening the network and forming a strong matrix [8, 37-38].

Bovine whey protein has been shown to promote the growth and differentiation of osteoblasts across species [14-16], while suppressing osteoclast activity [17]. The role of osteoblasts is to construct and remodel bone tissue, while osteoclasts dissolve bone minerals and break down bone. The immunogenicity of WPI using WPI biofilms (10% WPI with glycerol or diethylene glycol) has been found to be benign in mice when implanted for up to 60 days [30].

Calcium chloride is added to improve gelling properties [31, 37, 43]. In an extensive study covering different salts and their relative impacts on the viscosity and gelation ability of whey protein solutions, calcium chloride ranked among the best gel-inducing salts [32]. These results have since been reproduced in other studies [11, 21], making the precursor suspension similar to the well-studied solutions of lower protein content.

Nanocomposites have been shown to drastically enhance the mechanical properties of a polymer matrix [33]. Polysaccharides were selected due to the proven ability of cellulose to reinforce a polymer matrix [34-35], and because it has been suggested that their hydro lytic degradation products may serve as an added nutrient source for proliferating cells. A built-in nutrient source would improve the growth and mineralization characteristics and expand the feasible scaffold dimensions—generally physically limited by insufficient diffusion into the scaffold interior [36].

U.S. Pat. No. 6,337,198 discloses a biodegradable and biocompatible porous scaffold for tissue engineering, using several polymers including, for example, hydroxycarboxylic acid and copolymers thereof, bisphenol-A based polyphosphoesters, and tyrosine-derived diphenol compounds.

U.S. Pat. No. 6,753,004 discloses a biodegradable fishing lure formed from a material which includes sucrose, gelatin, sodium alginate, locust bean gum, calcium chloride, starch, corn syrup, glycerin, sodium benzoate, and sodium metaphosphate. Whey is listed as one potential protein component.

U.S. Pat. No. 7,556,800 discloses a fishing lure comprised of fibrous collagen.

U.S. Pat. No. 7,615,593 discloses hydrogels where a polymer matrix is modified to contain a bifunctional poly(alkylene glycol) molecule covalently bonded to the polymer matrix, including polymer matrix made from whey protein gels.

U.S. Patent Application Publication No. 2006/0008445 discloses a fishing lure comprised of a matrix of fibrous collagen.

DISCLOSURE OF INVENTION

We have developed a new biodegradable hydrogel material based on whey protein isolate (WPI). We have characterized the new hydrogel, and tested for use as a bioscaffold in bone regeneration and for use as a fishing lure. WPI gels of different compositions were fabricated by thermally inducing gelation of high-concentration suspensions of protein, and characterized for compressive strength and modulus, hydration swelling and drying properties, mechanical behavior change due to polysaccharide additives, and intrinsic pore network structure. The gels were also tested for their compatibility with MC3T3-E1 cells, and interactions such as cell adhesion, cytotoxicity, proliferation kinetics, and bone formation. We found the most preferred bioscaffold for bone tissue regeneration would comprise about 40% w/v WPI, about 10 mM $CaCl_2$, and about 0.2 g amylopectin per g WPI. The mechanical properties of this composite approached the ultimate strength necessary for a load-bearing scaffold, and were within one order of magnitude of the lower limit of the necessary compressive modulus.

The observed cell-scaffold interactions were highly suitable. All tested naïve gels and composites supported the adhesion and proliferation of the model cell line for extended culture periods. Amylopectin incorporation decreased initial preosteoblast adhesion but improved the proliferation rate constant—the more important system parameter. Both the naïve gel and the composites enabled cells to differentiate and create bone in vitro, and sustained viability for the length of the 4-week study. In addition, we tested electrospinning as a method to make the bioscaffold material.

We have made thermally-induced whey protein hydrogels containing varying amounts of additives (including salts and polysaccharides) and have cast or machined the hydrogels into various shapes, including fishing lures. We have also made a nanofibrous matrix of WPI using electrospinning, which could be formed into a nanofibrous 3D nonwoven porous structure. The advantages of these whey protein isolate (WPI) hydrogels include biodegradability, biocompatibility, environmentally friendly, adjustable range of mechanical and physical properties, easy manufacturing process, and sustainable precursors.

Areas of possible commercial interest include tissue regeneration, food protection, controlled-release applications (including drug encapsulation, dietary supplement release, attractant release in lures, nutrient release to plants (fertilizers)), column packing for compound separation, and membrane development.

BRIEF DESCRIPTION OF THE DRAWINGS

FIGS. 12C and 12D are expanded views of the shorter times (<250 min) of the same data shown in FIGS. 12A and 12B.

FIGS. 13C and 13D are expanded views of the shorter times (<250 min) of the same data shown in FIGS. 13A and 13B.

FIGS. 25A-25C are SEM micrographs of mineralized scaffolds with FIG. 25A showing MC3T3-E1, subclone 4 cells on a scaffold containing 35% w/v WPI scaffolds, FIG. 25B showing an acellular scaffold containing 45% w/v WPI, and FIG. 25C showing a subclone 24 (non-differentiating) cells on a scaffold containing 20% w/v WPI—all cultured for 28 days in mineralization medium. The scale bar in the figure represents 20 μm; and the inlay bar represents 2 μm. FIGS. 25D-25F show the elemental analysis of the mineralized scaffolds using EDS spectra and showing the analysis for the cells of FIG. 25A (FIG. 25D), FIG. 25B (FIG. 25E) and FIG. 25C (FIG. 25F), respectively. The x axis represents energy in keV, and the y axis represents intensity in counts.

FIGS. 26A-H illustrate SEM micrographs and elemental analysis of mineralized scaffolds of varying $CaCl_2$ concentrations, FIGS. 26A-D show SEM micrographs of 35%) w/v WPI mineralized scaffolds with FIG. 26A showing MC3T3-E1, subclone 4 cells on a scaffold with 0 mM $CaCl_2$, FIG. 26B showing an acellular scaffold containing with 0 mM $CaCl_2$, FIG. 26C showing MC3T3-E1, subclone 4 cells on a scaffold with 20 mM $CaCl_2$, and 26D showing an acellular scaffold containing with 20 mM $CaCl_2$, —all cultured for 28 days in mineralization medium. The scale bar in the figure represents 50 μm; and the inlay bar represents 2 μm. FIGS. 26E-26H show the elemental analysis of the mineralized scaffolds using EDS spectra and showing the analysis for the cells of FIG. 26A (FIG. 25E), FIG. 26B (FIG. 26F), FIG. 26C (FIG. 26G), and FIG. 25D (FIG. 25H), respectively. The x axis represents energy in keV, and the y axis represents intensity in counts.

FIGS. 27A-G illustrate SEM micrographs and elemental analysis of mineralized scaffolds of varying amylopectin concentration. FIGS. 27A-27D are SEM micrographs of mineralized scaffolds of varying amylopectin concentration using scaffolds of 35% w/v WPI and 10 mM $CaCl_2$ scaffolds with FIG. 27A showing a scaffold containing 0.05 g amylopectin per g WPI with MC3T3-E1, subclone 4 cells, FIG. 27B showing a scaffold with acellular, containing 0 g amylopectin per g WPI, FIG. 27C showing a scaffold containing 0.25 g amylopectin per g WPI with subclone 4 (differentiating) cells, and FIG. 27D showing a scaffold containing 0.25 g amylopectin per g WPI with subclone 24 (non-differentiating) cells—all cultured for 28 days in mineralization medium. The scale bar represents 50 μm; and the inlay scale bar represents 5 μm. FIGS. 27E-27H show the EDS spectra with elemental analysis of FIG. 27A (FIG. 27D), FIG. 27B (FIG. 27E), FIG. 27C (FIG. 27G) and FIG. 27D (FIG. 27H. The x axis represents energy in keV; y axis represents intensity in counts.

FIG. 28A, porosity; FIG. 28B, pore coordination number; FIG. 28C, pore diameter; and FIG. 28D, throat diameter.

FIG. 29A shows the viscosities of six WPI suspensions (20%, 25%, 30%, 35%, 40%) and 45% w/v WPI) measured over a range of shear rates; and FIG. 29B shows viscosities for a shear rate of 10.5 $s^{-1}$ using cone and plate configuration with the calculated threshold viscosity to support 100 μm bubbles indicated by the horizontal line.

MODES FOR CARRYING OUT THE INVENTION

Figure 1:
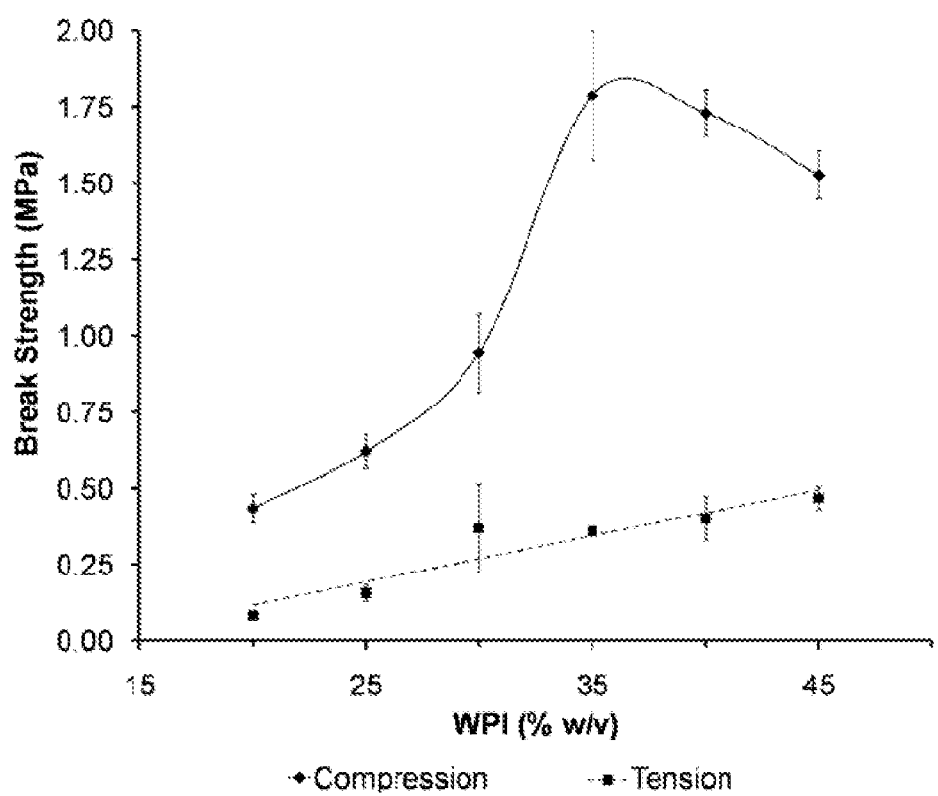
FIG. 1 illustrates the effect of whey protein isolate (WPI) on the mechanical strength (Break Strength) of WPI gels with 10 mM $CaCl_2$, with the curves representing stress at failure under compression and under tension.

We have designed a biodegradable, hydrogel material based on a high-concentration WPI gel. The compressive properties of the WPI gels depended on their compositions. Compressive strength was highest for a gel containing 35% w/v WPI and 2.5-10 mM $CaCl_2$. Elastic modulus was proportional to WPI concentration, but was highest between 5 and 15 mM $CaCl_2$. These trends corresponded to the aggregate size and the size of interconnects between aggregates that formed the gel. The most stable network corresponded to the gel with the highest mechanical strength. The composition of the gels also dictated both their initial water content and their swelling properties. The swelling was dependent on WPI concentration and to a greater extend, $CaCl_2$ concentration. Gels of higher WPI content or higher $CaCl_2$ content took up more water mass and grew to larger dimensions than gels of lower WPI or $CaCl_2$ content.

Five polysaccharide additives were incorporated into WPI precursor suspensions, and the gels analyzed. Of these, amylose, cellulose, and dextran detracted from the mechanical properties of the gel. Chitosan showed a possible increase in modulus but a decrease in compressive strength over the naïve gels. The best properties for a hydrogel were achieved for 40% w/v WPI, 10 mM $CaCl_2$, and 0.2 g amylopectin per g WPI, but the gel was showed 70% of the strength for a bone scaffold. For an effective bone regeneration scaffold, a nanocomposite might be used that has a filler on the nanoscale, functionalized with side groups that will strongly interact with the amino acid side groups of the protein, or the gel could be made using a mixture with the WPI of other known polymers, both synthetic and natural, e.g., fibrin, collagen, gelatin, chitosan, alginate, hyaluronic acid, polyethylene glycol, poly(alpha-hydroxyester)s, and polycolide.

In the two-dimensional in vitro experiments performed, the preosteoblast cells showed a high affinity towards the naïve WPI gels as well as the composites containing amylopectin. The cells adhered with high efficiency by static seeding in short seeding times (1 hour), with enough force to withstand subsequent rinsing prior to incubation. After short incubation they displayed the desired flat, stellate morphology indicating high-quality adhesion to the surface. The cells remained viable for long-term incubation (3 and 4 weeks in culture). On ail tested gel surfaces—spanning the feasible range of compositions—the cells exhibited exponential growth kinetics until saturation of the scaffold occurred. The proliferation kinetics depended to a degree on scaffold compositions. Seeding efficiency was enhanced by scaffold concentrations of at least 35% w/v WPI and 0-10 mM $CaCl_2$. The growth rate constants were roughly independent of composition, with a suggested increased rate for increasing $CaCl_2$ and amylopectin concentration. The rate of retardation constant did not exhibit a compositional dependence.

When provided with ascorbic acid to induce differentiation and an inorganic phosphate source, the cells were able to form a mineralized extracellular matrix during a 28-day culture period. Calcium and phosphorous were detected on all acellular scaffolds initially containing calcium in the matrix, indicating the deposition of a calcium phosphate layer on the surface. Saturation of almost all seeded scaffolds was reached during the 28-day period, and scaffolds seeded with the differentiating subclone of the cell line showed mineralized ECM, though only sporadic mineralization was seen on surfaces containing 0 mM $CaCl_2$. This indicated that the calcium source built into the matrix aided in scaffold mineralization. Scaffolds seeded with non-mineralizing subclones served as negative controls and showed no evidence of calcium phosphate formation, though the cultures thrived on the WPI and composite surfaces.

The proliferation and mineralization behavior of the WPI scaffolds were found to be suitable for use in bone regeneration. All tested scaffolds supported both proliferation and mineralization (and implicitly, osteoblastic differentiation) of progenitor cells. The optimal cellular behavior was observed for scaffolds contained high WPI, low-to-medium $CaCl_2$, and high amylopectin concentrations.

The WPI gel pore network structure was found to depend heavily on WPI concentration in the gel precursor suspension. It was determined that a threshold WPI concentration was necessary to obtain any detectable pore content in the material. This threshold is between 20% and 35% w/v WPI, and is dictated primarily by the viscosity of the gel precursor suspension. Between 20% and 35% w/v WPI, the suspension undergoes a shift from Newtonian to shear-thinning characteristics, and experiences a 33-fold increase in viscosity. The added suspension viscosity imparts a drag force great enough to trap large gas bubbles introduced during suspension preparation that escape during gelation when the viscosity is lower. Thus the presence of gas bubbles is important in making a scaffold with sufficient pore size. The incorporation of pores into the scaffold is important and can be accomplished with the above method, or with alternative methods of pore incorporation, including without limitation, electrospinning, salt leaching, and foaming. Pore size distributions within the proper range for successful 3D culture can be achieved for the porous gels (35% and 45% w/v WPI). Using the current processing technique, the highest porosity attained was 17.8%), which is below the range for a bone regeneration scaffold. Pore interconnectivity and inter-pore throat diameters were also found to be low. Additional void volume can be readily incorporated by modifying the current scaffold fabrication technique, e.g., by additional aeration and agitation, by electrospinning, by salt crystals, or by polymer solid leaching, or adding other known polymers. We were able to produce fibers of varying diameter using electrospinning.

One scaffold formulation was 40% w/v WPI, 10 mM $CaCl_2$, and 0.2 g amylopectin per g WPI in water. This composition was optimal for thermal gelation at 80° C. for approximately 12 minutes for every millimeter of characteristic length. At this composition, the compressive strength and compressive modulus were the highest achieved, the porosity was near its highest, and the pore size distribution was favorable. Seeded cells on the WPI gels showed high seeding efficiency (>75% after 1 hour), rapid proliferation, and unobstructed differentiation and mineralization.

We have also replaced water in the WPI gels with a fraction of glycerol. The glycerol-containing gels showed at least two advantages over WPI gels with no glycerol: the gels containing glycerol had higher flexibility, and the gels maintain their hydrated state for a substantially longer period of time (greater than 6 months) when glycerol is incorporated in the matrix in quantities equal to or greater than that of water. There was no significant changes in processing of the gel as glycerol shows similar solvent properties to water. The glycerol/water WPI gels are useful for producing fully biodegradable fishing lures in addition to use as scaffolds or mats for more flexible tissues, particularly cartilage and skin.

In addition, the WPI gels can incorporate other additives (e.g., amino acids, growth factors, DNA, drugs), to improve the performance of the gel as a tissue regeneration scaffold (e.g., for bone, cartilage, skin in wound healing), a controlled-release hydrogel, or a fishing lure. For example, additives to be added to improve the structure of the WPI hydrogel include cellulose, amylose, amylopectin, glycogen, dextran, other polysaccharides or polymers. Natural or synthetic polymers could be added including fibrin, collagen, gelatin, chitosan, alginate, hyaluronic acid, poly(lactic acid) poly(glycolic) acid, poly(lactic-co-glycolic acid), poly(ether ketone), poly(ε-caprolacotone), poly(alpha-hydroxyester)s, and polyglycolide. Natural or synthetic amino acids can be added to improve a fishing lure or improve the cell growth on scaffolding. Other known additives for tissue scaffolds include, but are not limited to, antibiotics, stem cell growth factors, heparin-binding proteins, hyaluronic acid, nerve growth factor, adrenomedullin, autocrine motility factor, bone morphogenetic proteins (BMPs), brain-derived neurotrophic factor (BDNF), epidermal growth factor (EGF), erythropoietin (EPO), fibroblast growth factor (FGF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin-like growth factor (IGF), migration-stimulating factor, myostatin (GDF-8), nerve growth factor (NGF) and other neurotrophins, platelet-derived growth factor (PDGF), thrombopoietin (TPO), transforming growth factor alpha (TGF-α), transforming growth factor beta (TGF-β), tumor necrosis factor-alpha (TNF-α), vascular endothelial growth factor (VEGF), Wnt Signaling Pathway factors, placental growth factor (PlGF), adhesion factors (e.g., RGD, IKVAV (SEQ ID NO:1), YIGSR (SEQ ID NO:2), RNAIAAEIIKDI (SEQ ID NO:3), HAV), hyaluronic acid, galactose, heparin, and carbohydrates. In addition, lipids or lipid derivatives could be added.

As indicated above and shown below, the WPI hydrogels can be formulated various ways to meet the use intended for the hydrogel. Some preferred formulations are the following. For use as a fishing lure, the formulation can be adjusted depending on if strength or flexibility is more important. For example, a fishing lure with high strength could be about 40% WPI, 20 mM calcium chloride (or other salt), 15% amylopectin by weight, and water. For a fishing lure with high flexibility, the formulation could be about 30% WPI, about 5 mM calcium chloride (or other salt), 5% amylopectin by weight, and water. To improve hydration stability of the lures, use of a solvent that is at least 25% v/v glycerol in water (as opposed to water only) can be used. This would allow for lure storage in an open environment for greater than 6 months without compromising the physical properties of the lure. For a fishing lure with intermediate flexibility and strength, the formulation could be a blend of the above compounds. Other compounds can be added to a fishing lure to attract the fish to the lure, including various amino acids or other known fish attractants, e.g., proteins, fish extracts, other animal extracts, and blood.

For a bone tissue regeneration scaffold, the preferred system would be from about 30-45% WPI with 5-25 mM calcium chloride or other salt or calcium source and up to 30% of amylopectin or other compounding agent. The most preferred formulation would be about 35-40% WPI, 10 mM calcium chloride (or other salt), 20% amylopectin by weight, addition of one or more compounding additives for strength (e.g., amylopectin), and water. Other compounds known to promote bone regeneration could be added, including without limitation, transforming growth factor-β superfamily (especially TGF-β1), platelet-derived growth factor (PDGF), insulin-like growth factor (IGF), hone morphogenic proteins (BMPs), fibroblast growth factor (FGF), and vascular endothelial growth factor (VEGF)[42].

For a skin tissue scaffold, the preferred formulation would be about 20-45% WPI, 2-25 mM calcium chloride or other salt or calcium source, any concentration of glycerol greater than 25% v/v and up to 25% of amylose or other compounding agent would be acceptable. The most preferred formulation for use on skin is about 30% WPI, about 5 mM calcium chloride (or other salt), 10% amylose by weight, and a 1:1 solution of glycerol and water. Compounds known to promote skin regeneration or wound healing could be added, included without limitation, epidermal growth factor (EGF), fibroblast growth factors (FGFs), TGF-β, and PDGF.

The preferred formulation for a cartilage tissue scaffold is about 20-45% WPI, 2-25 mM calcium chloride or other salt or calcium source, any concentration of glycerol greater than 25% v/v water and up to 25% of amylose or other compounding agent. For a cartilage tissue scaffold, the most preferred formulation would be about 35% WPI, about 8 mM calcium chloride (or other salt), 20% amylopectin by weight, and a 1:3 solution of glycerol and water. Compounds known to promote cartilage regeneration could be added, included without limitation, IGF, PGF, FGFs, BMPs, TGF-β, and PDGF.

EXAMPLE 1

Mechanical Properties of the Naïve Gel

Materials: All water used in this work was >18 MΩ polished water from a Direct-Q® 3 water purification system (Millipore, Billerica, Mass.). The materials used were Whey Protein Isolate (WPI) powder from Davisco Foods International (Eden Prairie, Minn.), where powder composition was: beta-lactoglobulin 68-75%, alpha-lactalbumin 19-25%), bovine serum albumin 2-3%, immunoglobulin 2-3%; calcium chloride dihydrate from Maliinckrodt Chemicals (Hazelwood, Mo.); and phosphate buffered saline solution (NaCl, KCl, $Na_2HPO_4$, $KH_2PO_4$ from Sigma-Aldrich, St. Louis, Mo.). MC3T3-E1 subclone 4 preosteoblast cells were purchased from ATCC (Manassas, Va.), and αMEM, penicillin/streptomycin, fetal bovine serum, and Fungizone from Invitrogen (Carlsbad, Calif.).

Scaffold Fabrication: Samples for material testing were prepared by adding WPI powder to an aqueous $CaCl_2$ solution of half the volume and double the concentration desired for the final mixture. The final compositions ranged from 20 to 45% w/v WPI and 0 to 50 mM $CaCl_2$. To achieve these high WPI-containing slurries, protein powder was gradually added to the aqueous solution with vortexing to mix between steps. Then the mixtures were adjusted to the final weight ratio by adding water and vortexing once more.

The pH of the various mixtures ranged from about 6.5 to about 6.8. The volume of slurry was kept at 20% of that of the vessel, to allow for effective vortexing. The resulting viscous precursor slurries were then cast into the desired sample geometries.

Samples for compressive testing were loaded into custom PTFE molds manufactured in-house. The molds were cylinders of 7.62 cm (3 inches) in length, and 10 mm in diameter. Samples for tensile testing were loaded into aluminum molds to generate type-IV dogbones as specified in ASTM D638 [45]. Gelation was induced thermally by curing at 80° C. for 60 minutes (cylinders) or 45 minutes (dogbones). The cure time was established based on results shown in Example 3, which indicate that increasing cure time above 45 minutes resulted in no change in mechanical properties. Additional time was used for the cylinders to compensate for the heat conductivity of PTFE vs. aluminum and for the increased characteristic length of the sample (5 mm vs. 1.5 mm). The samples were then cooled at room temperature for 10 minutes and removed from the molds. The cylinders were cut to 10 mm lengths using a diamond-blade rotating saw for an aspect ratio of 1. The finished samples were allowed to swell in PBS for 2 hours prior to testing to ensure proper hydration and achieve their final dimensions.

Ultimate Mechanical Testing: Compressive and tensile testing was performed using an Instron universal testing system (model #4411, Instron, Norwood, Mass.) at a cross-arm speed of 5 mm/min until failure. Only samples with breaks near the center of the sample were included in stress/strain calculations and analysis to eliminate break artifacts related to geometry. The load-deformation data were converted to stress-strain curves, and the failure point and initial slope of each were identified. The stress was calculated as load per initial cross-sectional area and strain was calculated as the change in length divided by the initial length. The sets of samples were designed to test the full range of WPI concentrations forming a solid gel (20 to 45% w/v) at a constant $CaCl_2$ concentration, and a wide range of salt concentrations (0 to 40 mM) for constant protein concentrations: 30, 35%, and 40% w/v WPI.

In Vitro Testing: Mouse preosteoblast MC3T3-E1 subclone 4 (SC-4) cells were cultured in alpha-minimum essential medium (α-MEM) with 10% fetal bovine serum (FBS), 100 U/mL penicillin, 100 µg/mL streptomycin, and 2.5 µg/mL Fungizone (amphotericin B). The cells were incubated at 37° C. in high-humidity and 5% $CO_2$ atmosphere.

Samples of WPI gels were seeded with MC3T3-E1 mouse preosteoblasts and cultured in vitro to assess the capability of WPI gels to support cell growth. A precursor WPI solution of 45% w/v WPI and 10 mM $CaCl_2$ was cast into the wells of a non-tissue culture treated 12-well polystyrene plate and cured for 20 minutes at 80° C. The plate was then cooled to room temperature and sterilized under UV overnight. In each well, 1 mL of $10^4$ cells/mL cell suspension (passage 4) were used for static seeding, and the cells were cultured for 53 hours at 37° C. in 5% $CO_2$ atmosphere and 99% humidity. The samples were then prepared for scanning electron microscopy in order to visualize the growth surfaces.

Scanning Electron Microscopy: To correlate the topography of WPI gels with mechanical data, sample cross-sections comprising a range of WPI and $CaCl_2$ concentrations were viewed by scanning electron microscopy (SEM). Samples fabricated for SEM were rinsed with phosphate buffered saline (PBS) and fixed by a 2%-gluteraldehyde/ 1%-formaldehyde fixative solution and rinsed three times with 0.1 M cacodylate buffer. A postfix in a 0.1 M cacodylate buffer/0.004 M glycine solution followed. The fixed samples were dehydrated via submersion in a graded series of ethanol and then dried by critical point $CO_2$. The dried samples were then mounted to SEM stages using double-sided conducting adhesive and sputter-coated with gold for 2 minutes at 10 mA plasma discharge. The samples were imaged under vacuum at 5 kV.

Samples from in vitro studies were processed in a similar fashion with the following modifications. The surface of interest was already exposed, so the samples were not fractured, but were cored so-as to conform to sample-size specifications of the stage. Also, prior to ethanol dehydration, the samples underwent a post-fixation step with osmium tetroxide.

Statistical Analysis: Data are presented as means of at least three replications and standard deviation. Statistical significance was determined by performing a Studentized Tukey test ($\alpha=0.05$) for every paired means in the mechanical testing data.

Figure 2:
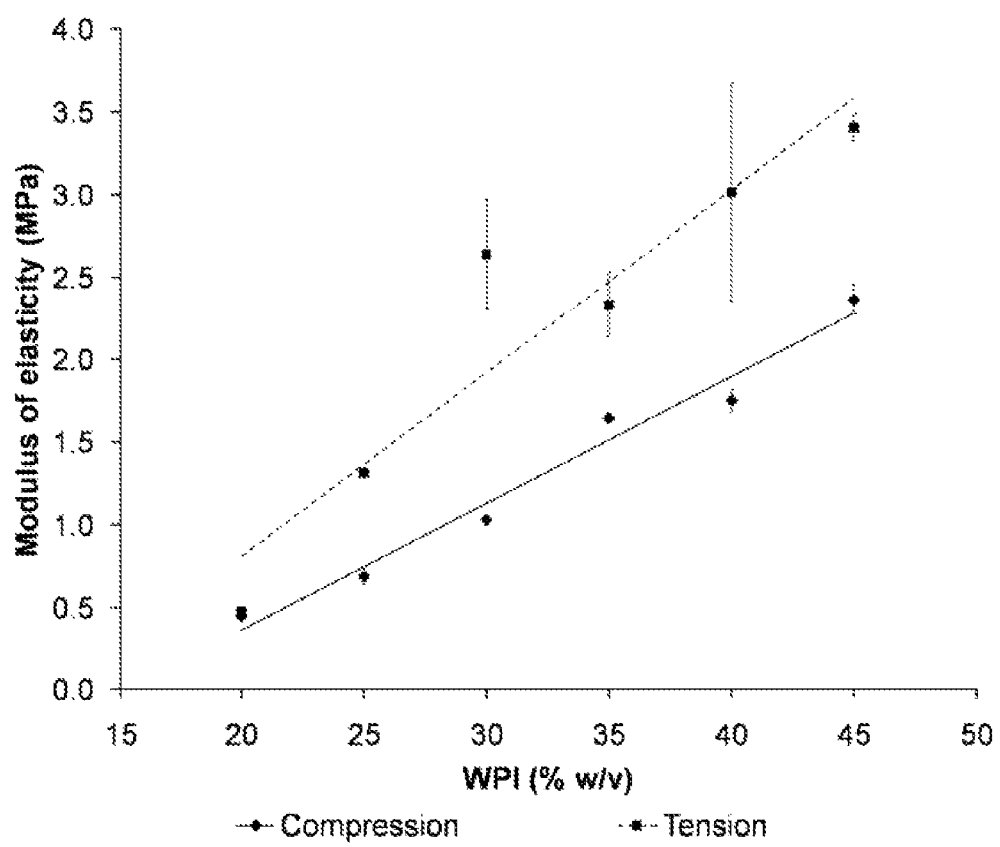
FIG. 2 illustrates the effect of whey protein isolate (WPI) on the modulus of elasticity of WPI gels with 10 mM $CaCl_2$, with the curves representing compressive modulus and Young's modulus.

Concentration Effects of Whey Protein Isolate on Mechanical Properties: The compressive and tensile properties of the whey protein gels were shown to be functions of WPI concentration (FIGS. 1-2). FIG. 1 plots the mechanical strength of the gel versus the WPI concentration. The curves represent stress at failure under compression and tension of WPI gels of 10 mM $CaCl_2$. FIG. 2 plots the modulus of elasticity versus the WPI concentration. The lines represent compressive modulus and Young's modulus of WPI gels of 10 mM $CaCl_2$. The ultimate compressive strength increased with protein concentration, up to a point, then reached a maximum and decreased (FIG. 1). The maximum strength observed was 1.79±0.21 MPa, and corresponded to 35% w/v WPI at 10 mM $CaCl_2$. The tensile strength increased proportionally with protein concentration. The highest tensile strength observed was 0.47±0.04 MPa, and corresponded to 45% w/v WPI at 10 mM $CaCl_2$.

Figure 3:
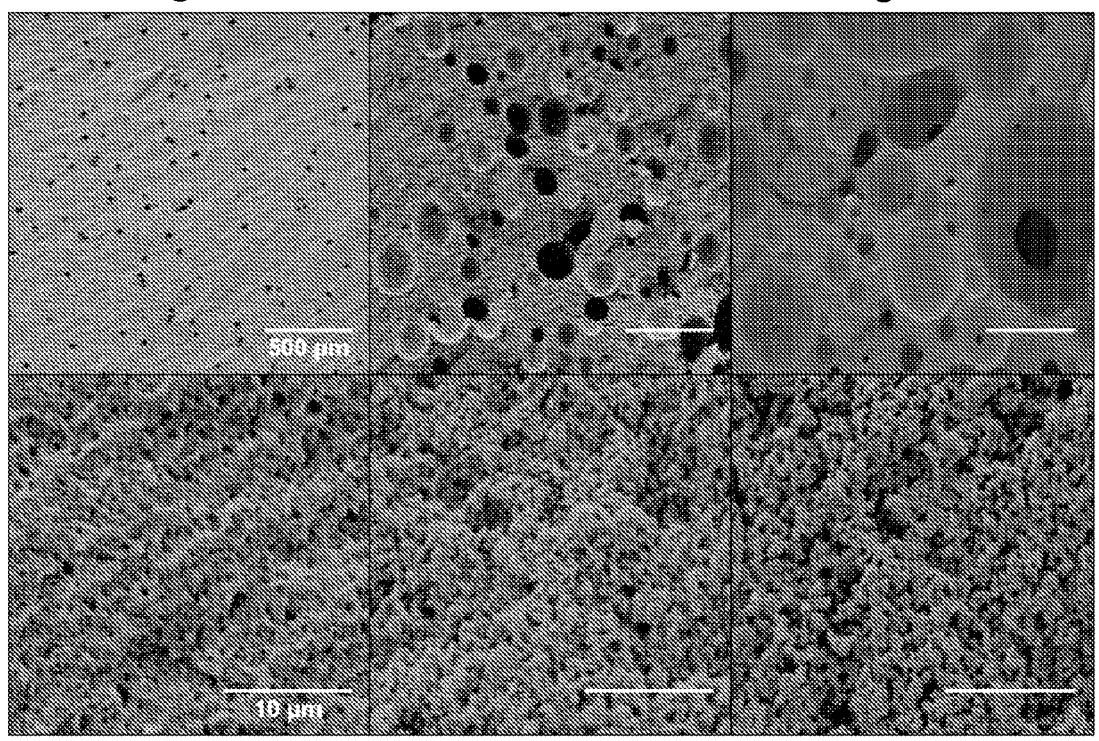
FIGS. 3A-3F illustrate scanning electron micrographs (SEMs) at a lower (FIG. 3A-3C) and higher (FIGS. 3D-3F) magnification of WPI gels of 20% WPI (FIGS. 3A, 3D), 35% WPI (FIGS. 3B, 3E), and 45% WPI (FIGS. 3C, 3F).

The ultimate tensile material strength was consistently lower than the corresponding compressive strength. FIGS. 3A-3F are scanning electron micrographs (SEMs) at a lower (FIG. 3A-3C) and higher (FIGS. 3D-3F) magnification of WPI gels of 20% WPI (FIGS. 3A, 3D), 35% WPI (FIGS. 3B,3E), and 45% WPI (FIGS. 3C, 3F). The SEMs show the change in microarchitecture as the WPI concentration increases. When a compressive load is applied, the force is displaced into the collapse of the prevalent macropores observed in FIGS. 3A-3C, delaying the full failure of the material. Under a tensile load, the pores cannot offset the force, and the cross-links between protein molecules dictate the failure—resulting in lower strength. The scarcity of pores in FIG. 3A supports this theory, as the difference in strength for this gel between the two testing directions is the smallest in the range.

The failure trend under compression was an unexpected result, though it proved repeatable and statistically significant. The closest conditions to the ones in this study were heat-induced WPI gels of up to 18% WPI [37]. Since protein concentration has such an impact on gel structure and properties, it is impossible to extrapolate these results to the range addressed in this work. The results above show a peak strength between about 35 and 40% w/v WPI. The added void volume in the gels likely contributes to the phenomenon, since the SEMs in FIGS. 3A-3C show an increased porosity as WPI content increases. The decrease in material strength between 35% and 45% w/v WPI could also be explained by the change in the type of gel structure formed, as evident by the images in FIGS. 3A-3F, discussed below.

Both the compressive and tensile elastic moduli of the gels followed a linear relationship with respect to WPI concentration (FIG. 2). The compressive modulus increased linearly with protein concentration, with the highest observed being 2.37±0.09 MPa. The modulus corresponding to the highest-strength sample (35% w/v WPI) was 1.65±0.02 MPa. The highest observed tensile elastic modulus was 3.41±0.08 MPa which corresponded to 45% w/v WPI and 10 mM $CaCl_2$. This relationship is caused in part by the crosslink density of the gel, which increases with protein concentration. FIG. 2 shows that the tensile elastic modulus is higher than the compressive modulus throughout the range.

Gel Morphology and Microstructure: Scanning electron micrographs of gel cross-sections of different WPI concentrations at 10 mM $CaCl_2$ were used to correlate the mechanical behavior observed to the microarchitecture of the gels (FIGS. 3A-3F). The effects of protein concentration on the macrostructure can be seen in FIGS. 3A-3C, which represent gels of WPI concentrations of 20, 35, and 45% WPI, respectively. A distinct increase in both porosity and pore size is observed as protein concentration is increased. Additionally, at higher protein concentrations, greater pore interconnectivity can be observed (FIGS. 3B-3C). The differences observed were caused by the varying viscosities between the precursor slurries. The higher WPI slurries were more viscous and able to support larger air bubbles, which became pores upon curing. The scarcity of pores in FIG. 3A helps explain the difference between compressive and tensile ultimate strength, as the difference in strength for this gel between the two testing directions is the smallest in the tested range.

The microstructure of the same gels can be seen in FIGS. 3D-3F, at higher magnification. These images indicate a direct correlation between WPI concentration and the surface roughness of the cross section. The surface of the low-WPI gel (FIG. 3D) is relatively smooth and flat, while the higher-WPI gels are rougher with a more globular structure (FIGS. 3E-3F). The images in FIGS. 3A-3F suggest a phase-separated microarchitecture of the gel, which transitions from a coarse-grained structure—consisting primarily of a fine-stranded network, connected by fine strands of associated protein, to a biocontinuous structure—characterized by small aggregates interconnected by aggregated strands, to a protein-continuous structure—characterized by large protein aggregates mostly separated by the aqueous phase.

EXAMPLE 2

Concentration Effects of Calcium Chloride

Figure 4:
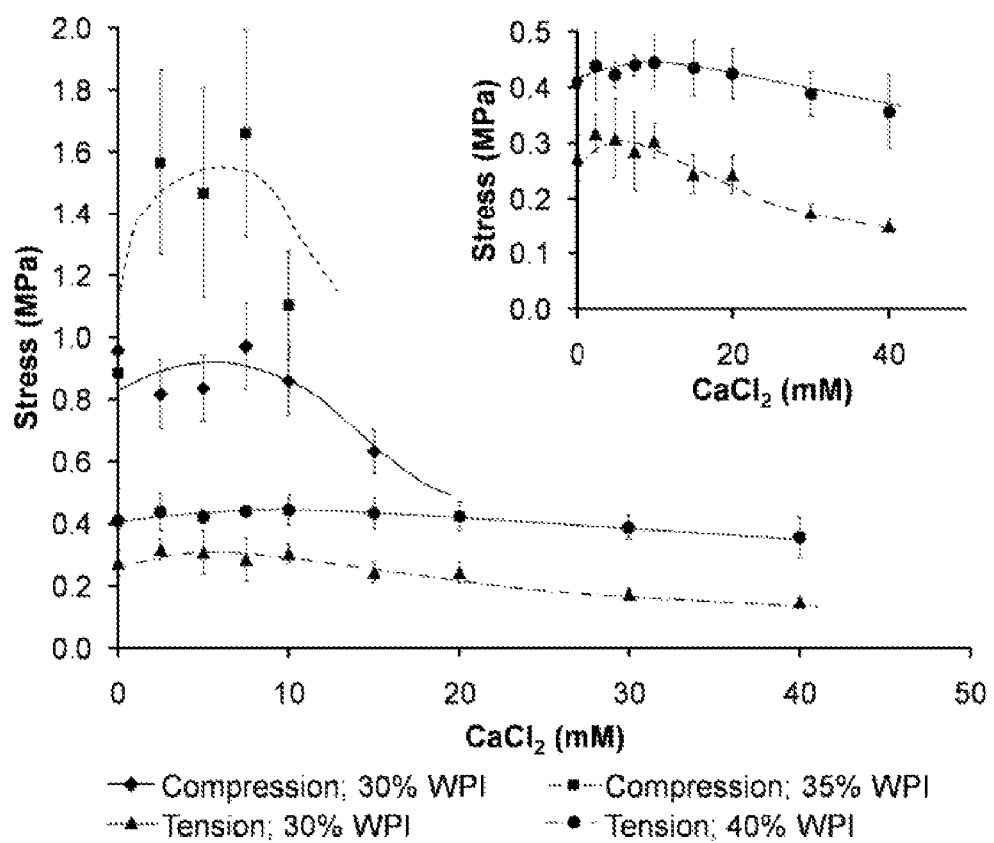
FIG. 4 illustrates the change in mechanical strength as a function of calcium chloride concentration. The curves represent stress at failure under compression of 30% w/v WPI and 35% w/v WPI, and under tension of 30% w/v WPI and 40% w/v WPI. The inlay plot is a clearer view of the tensile results.

Mechanical Properties: Using methods as described in Example 1, two sets of gels were tested to failure in compression. One was at 30% w/v WPI, and the second at 35%) w/v WPI—the concentration resulting in the highest observed mechanical strength. The effects of calcium chloride on the compressive strength of the material were evident but difficult to quantify, since gels made with a concentration greater than 20 mM $CaCl_2$ compressed uniformly to greater than 90% deformation without failure. FIG. 4 shows a plot of mechanical strength versus calcium chloride concentration. The curves represent stress at failure under compression of 30% w/v WPI and 35% w/v WPI, and under tension of 30% w/v WPI and 40% w/v WPI. The inlay plot is a clearer view of the tensile results. The results for gels of lower concentration demonstrate an optimum strength, observed at 1.66±0.34 MPa, corresponding to a concentration of 7.5 mM $CaCl_2$ and 35% WPI (FIG. 4). Under tension, two sets of gels were also tested—this time, one was at 30% w/v WPI (for comparison to compressive results), and the second at 40% w/v WPI—as a change less than 10% in WPI concentration exhibited no statistical difference in tensile properties. Results are also shown in FIG. 4. At both protein concentrations, the ultimate tensile strength showed the same trend with respect to $CaCl_2$ concentration as the compressive strength (FIG. 4 inlay). The maximum tensile strength achieved was 0.44±0.05 MPa and occurred at a $CaCl_2$ concentration of 10 mM and 40% w/v WPI. As before, the compressive strength was consistently higher that the tensile strength.

Figure 5:
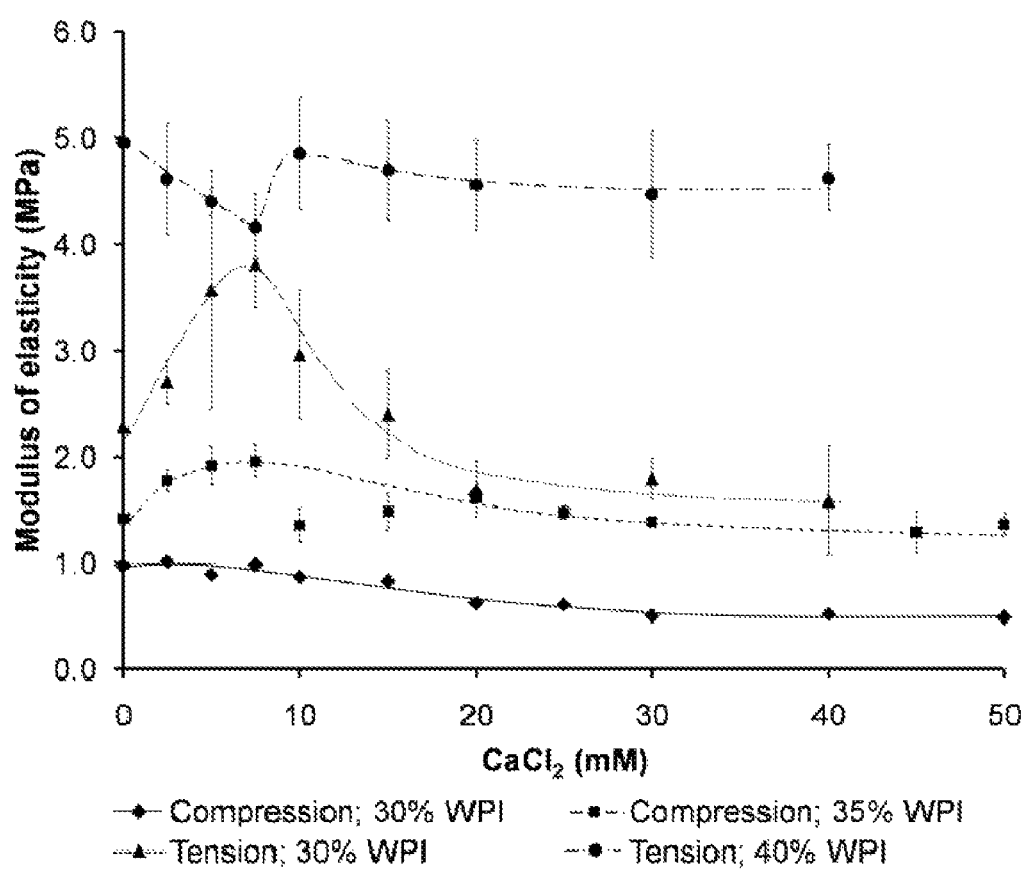
FIG. 5 illustrates the change in the modulus of elasticity as a function of calcium chloride concentration. The curves represent Young's modulus of gels of 30% w/v WPI and 40%) w/v WPI, and compression modulus of gels of 30% w/v WPI and 35%) w/v WPI.

The compressive modulus was determined to be a weak function of $CaCl_2$ concentration (FIG. 5), and is available for the full range tested, since it is a property inherent to the initial behavior of the gel under compression. FIG. 5 is a plot of the modulus of elasticity versus calcium chloride concentration. The curves represent Young's modulus of gels of 30% w/v WPI and 40% w/v WPI, and compression modulus of gels of 30% w/v WPI and 35% w/v WPI. A maximum compressive modulus of 1.96±0.15 MPa was obtained at a concentration of 7.5 mM $CaCl_2$ and 35% WPI. The tensile elastic modulus of the gels was shown to be a stronger function of $CaCl_2$ concentration at the WPI concentrations tested, particularly at 30% w/v WPI (FIG. 5). The maximum tensile elastic modulus achieved was 4.95±0.22 MPa and corresponded to a $CaCl_2$ concentration of 0 mM and protein concentration of 40% w/v WPI. An important indicator of the of WPI gels is the aggregate size in the precursor solution. It is this property that calcium chloride affects, leading to gels of varying strengths for varying $CaCl_2$ concentrations. Added calcium chloride results in larger aggregates, and aggregate size prior to gelation inversely affects gel strength.

Figures 6A, 6B, 6C, 6D, 6E, 6F:
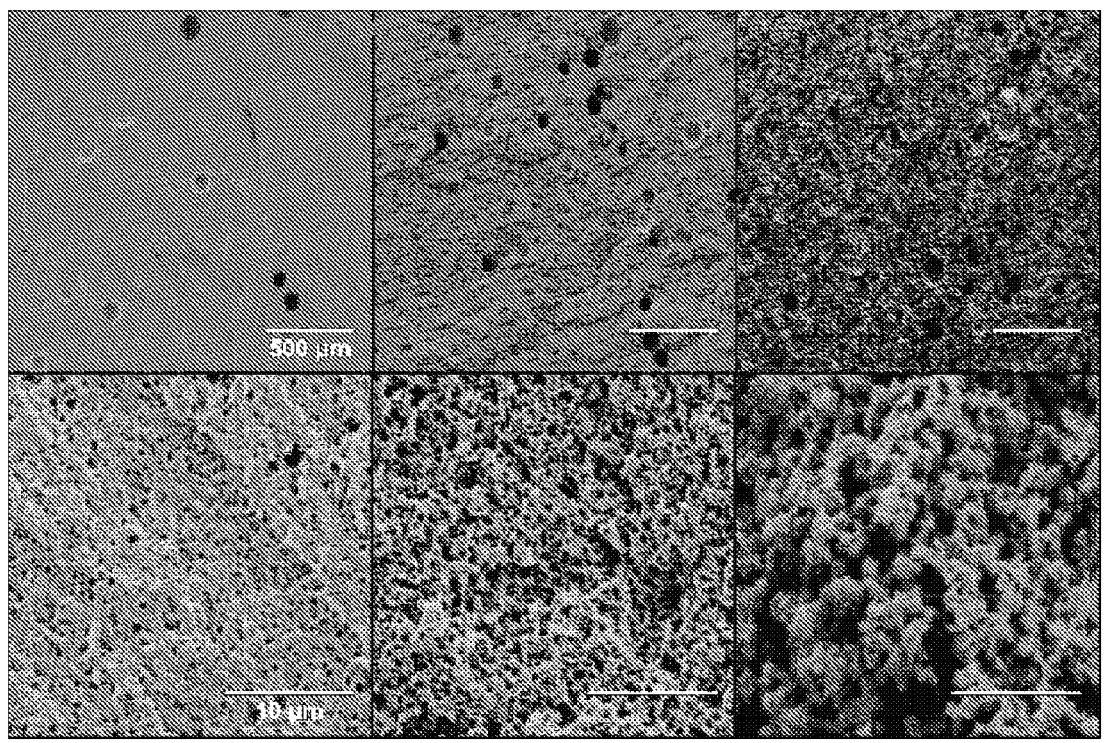
FIGS. 6A-6F are scanning electron micrographs (SEMs) of gels of 30% w/v WPI at a lower (FIG. 6A-6C) and higher (FIGS. 6D-6F) magnification of WPI gels of 0 mM $CaCl_2$ (FIGS. 6A, 6D), 10 mM $CaCl_2$ (FIGS. 6B,6E), and 40 mM $CaCl_2$ (FIGS. 6C, 6F).
Figures 7A, 7B, 7C, 7D, 7E, 7F:
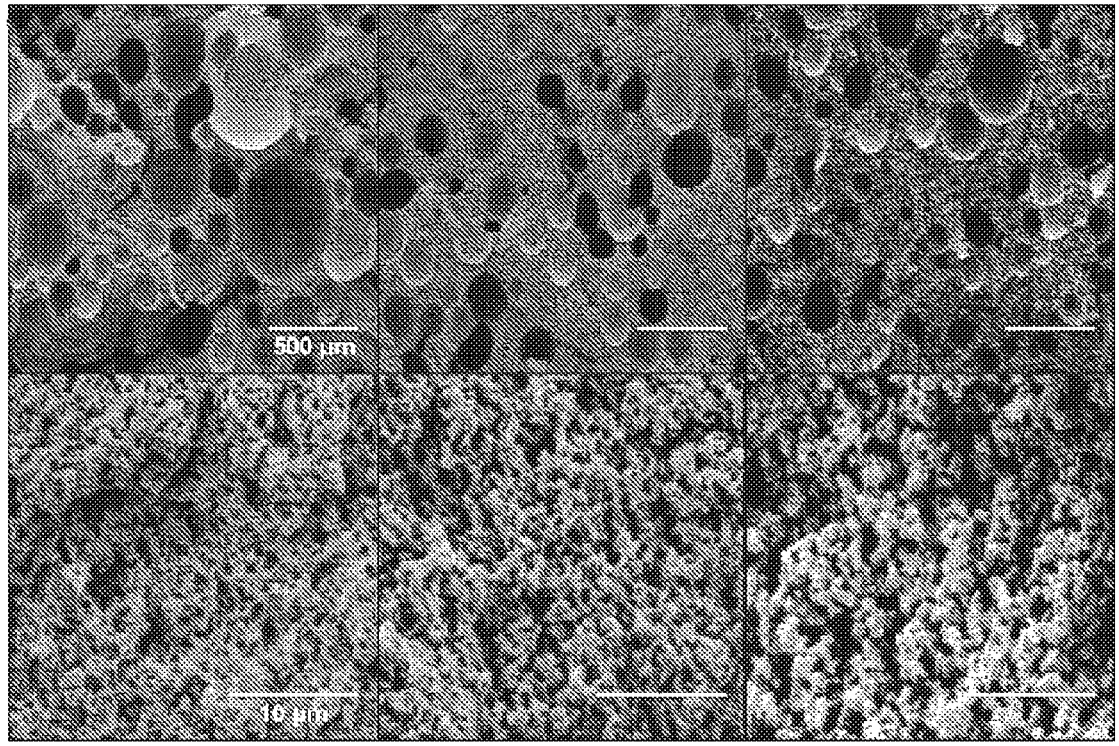
FIGS. 7A-7F are scanning electron micrographs (SEMs) of gels of 40% w/v WPI at a lower (FIG. 7A-7C) and higher (FIGS. 7D-7F) magnification of WPI gels of 0 mM $CaCl_2$ (FIGS. 7A, 7D), 10 mM $CaCl_2$ (FIGS. 7B, 7E), and 40 mM $CaCl_2$ (FIGS. 7C, 7F).

Gel Morphology and Microstructure: Scanning electron micrographs of gel cross-sections for varying $CaCl_2$ concentrations at 30% w/v WPI (FIGS. 6A-6F) and 40% w/v WPI (FIGS. 7A-7F) were used to correlate the mechanical behavior observed to the microarchitecture of the gels. FIGS. 6A-6F are scanning electron micrographs (SEMs) of gels of 30% w/v WPI at a lower (FIG. 6A-6C) and higher (FIGS. 6D-6F) magnification of WPI gels of 0 mM $CaCl_2$ (FIGS. 6A, 6D), 10 mM $CaCl_2$ (FIGS. 6B,6E), and 40 mM $CaCl_2$ (FIGS. 6C, 6F). FIGS. 7A-7F are scanning electron micrographs (SEMs) of gels of 40% w/v WPI at a lower (FIG. 7A-7C) and higher (FIGS. 7D-7F) magnification of WPI gels of 0 mM $CaCl_2$ (FIGS. 7A, 7D), 10 mM $CaCl_2$ (FIGS. 7B, 7E), and 40 mM $CaCl_2$ (FIGS. 7C, 7F). The effects of $CaCl_2$ concentration on the gel macrostructure can be seen in FIGS. 6A-6C, as well as FIGS. 7A-7C, which represent gels of $CaCl_2$ concentrations of 0, 10, and 40 mM, respectively. Direct comparison of FIGS. 6A-6C with FIGS. 7A-7C suggest that, although the increased calcium chloride in the gels may contribute to an increased frequency of macropores present in the gels, the pore size is independent of this variable. On the other hand, a pronounced increase in surface roughness can be attributed to the increased $CaCl_2$. This finding makes it possible to select the concentration of calcium chloride to optimize the mechanical properties of the gel without further consideration of the macropore structure, which was found to be dictated only by the viscosity of the precursor slurry and pre-gelation air content.

The microstructure of the same gels is visible in FIGS. 6D-6F and FIGS. 7D-7F. These images indicate a direct correlation between calcium chloride concentration in a gel and its roughness, nanoporosity, and structural globularity.

These properties increase with the added salt. Also noteworthy was the ability to form a self-supporting gel without the addition of salt. In some studies the addition of salt was essential to heat-induced gelation [28-29]. These studies generally used a maximum protein concentration of 10%. With no calcium chloride (FIG. 6D), the gel is exceedingly smooth and the small aggregates are scarcely discernable from the connections between them. On the other hand, with 10 mM $CaCl_2$ (FIG. 6E), the aggregates are larger and form a globular structure with a more prevalent nanopore network. This structure is even more pronounced in the 40 mM $CaCl_2$ gel (FIG. 6F), where the mean aggregate size approaches the micrometer scale. Furthermore, for each calcium chloride concentration, additional aggregation behavior is seen in the higher WPI gels shown in FIGS. 7D-7E.

Figure 8A:
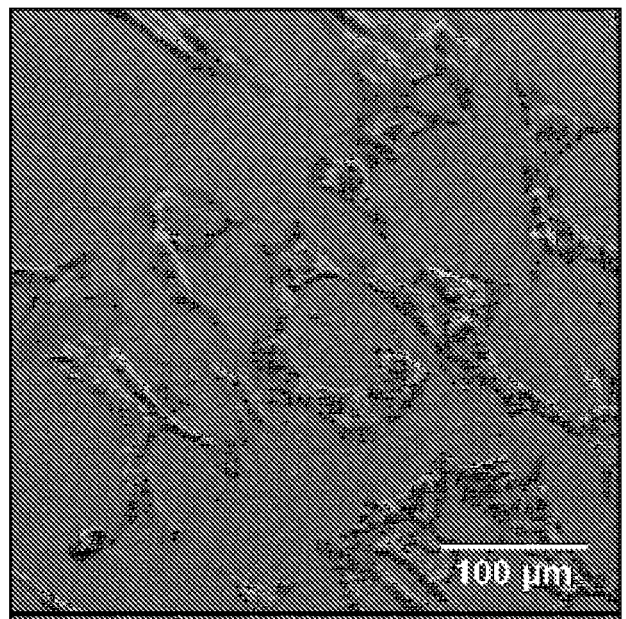
FIGS. 8A-8B show SEMs of MC3T3-E1 cells cultured on the surface of a 45% w/v WPI gel with 10 mM $CaCl_2$ at lower (FIG. 8A) and higher (FIG. 8B) magnification.
Figure 8B:
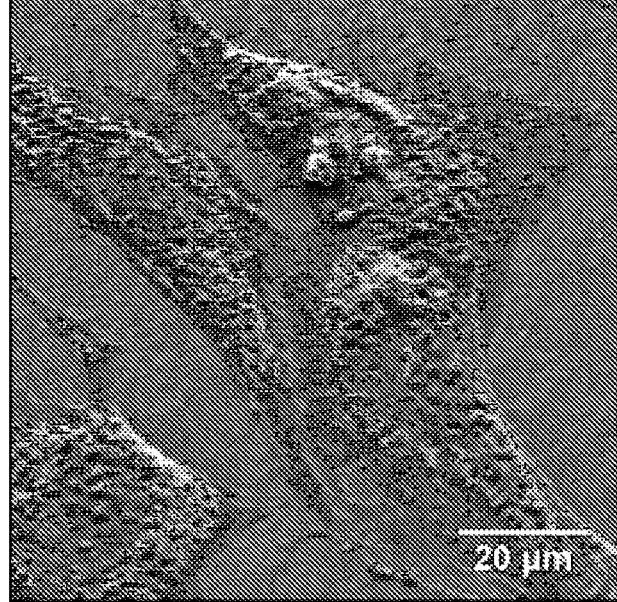

A rough scaffold surface improves its osteoinductive properties, or promotes the ingrowth of tissue into the scaffold. The gels of high WPI content and all but the lowest salt content exhibit the desired morphology for tissue regeneration. SEM micrographs of the 2D WPI gel surface prove the ability of the material to support the adhesion and proliferation of MC3T3-E1 mouse preosteoblasts. FIGS. 8A-8B show SEMs of MC3T3-E1 cells cultured on a WPI gel surface at lower (FIG. 8A) and higher (FIG. 8B) magnification. The cells were shown to be viable, with a morphology that was fiat and stellate, with pronounced filopodial extensions after 53 hours in static culture. Flat, large cells indicate good adhesion and a high affinity to the substrate, and the presence of filopodia suggests active cell motility—essential to form a uniform population of a scaffold. A distinct advantages of whey protein isolate as a scaffold thus is the ability to have favorable adhesion and proliferation characteristics, without any coating, physical or chemical surface modification, or bioactivation. WPI also requires no hazardous solvents during processing; rather, the fabrication is neat and carried out entirely in the aqueous phase.

A potential pitfall for the use of any material for implantation is the possibility of an adverse immune response. In the case of WPI, which contains proteins of known immunogenicity in hypersensitive individuals, the concern is increased. However, this immune response is greatly reduced by heat denaturation and at alkaline conditions, as used below in the examples. Others have reported suitability of WPI for implantation by conducting in vivo studies for up to 60-day finding WPI-based films to be non-immunogenic [30].

The dependence of the mechanical properties of high-concentration whey protein isolate gels on protein concentration and concentration of calcium chloride was characterized in detail. The highest material strength was achieved by using the optimum composition between about 35% and about 40% w/v WPI and 5-15 mM $CaCl_2$. The behavior of the elastic modulus followed the same trend as low-protein solutions and increased linearly with protein concentration. The ultimate strength and modulus necessary for a scaffold material for bone regeneration are likely achievable in a composite material based in the naïve gel examined in this study. The gels have demonstrated the ability to support the adhesion and proliferation of preosteoblast cells. The compressive modulus of WPI gels depended on their compositions. Compositions from 20% to 45% WPI were tested. Compressive strength was highest for a gel containing 35% w/v WPI and 2.5-10 mM $CaCl_2$. Elastic modulus was proportional to WPI concentration, but was highest between 5 and 15 mM $CaCl_2$. These trends corresponded to the aggregate size and the size of interconnects between aggregates that formed the gel. The most stable network corresponded to the gel with the highest mechanical strength.

EXAMPLE 3

Curing Time Profiles for WPI Gels

Figure 9A:
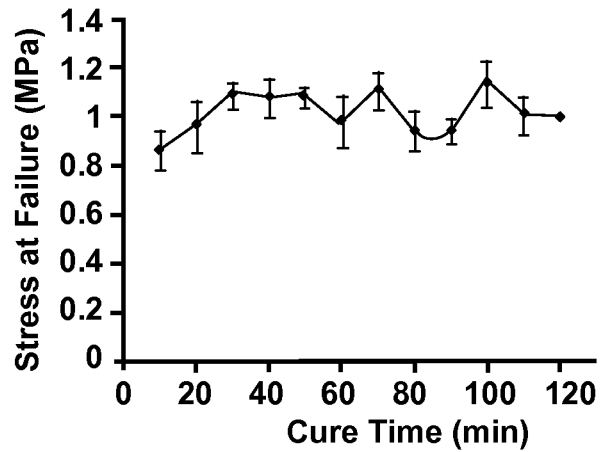
FIGS. 9A-9C show the mechanical properties of WPI gels as a function of cure time, with FIG. 9A showing compressive strength, FIG. 9B showing compressive modulus, and FIG. 9C showing break strain.
Figure 9B:
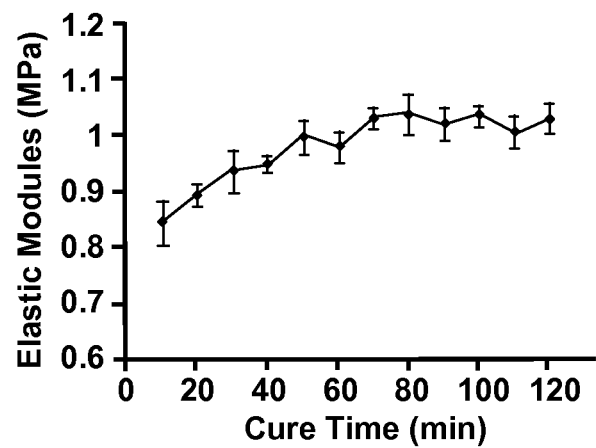
Figure 9C:
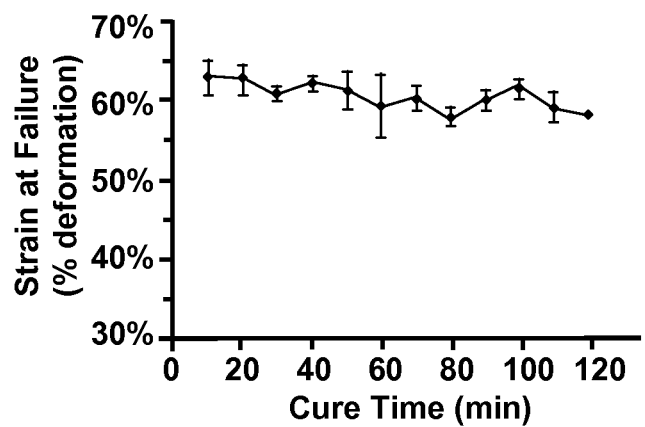

The time to cure the sol-gel precursor solution was determined by varying the cure times of gels of a representative composition. FIGS. 9A-9C shows the mechanical properties of WPI gels as a function of cure time, with FIG. 9A showing compressive strength. FIG. 9B showing compressive modulus, and FIG. 9C showing break strain. The optimal cure time will depend on the volume and surface area of the desired geometry. For the geometry tested is FIGS. 9A-9C (D=1 cm, L=5 cm), the cure time selected was 60 minutes, since it was the shortest time that yielded the best properties. The results can be translated qualitatively to other gel geometries, since the optimal cure time depends on the characteristic length of the gel. In a cylindrical sample of aspect ratio greater than one, as in this experiment, the characteristic length is the radius. A rule-of-thumb that can be used is 12 minutes of cure time per millimeter of characteristic length.

EXAMPLE 4

Hydration Characteristics of High-Concentration WPI Hydrogels

Materials and Methods: Experiments were conducted using WPI powder from Davisco Foods International (Eden Prairie, Minn.), calcium chloride dihydrate from Mallinckrodt Chemicals (Hazelwood, Mo.), and polished water (>18 MΩ) from a Direct-Q® 3 water purification system (Millipore, Billerica, Mass.). All other reagents were purchased from Sigma-Aldrich (St. Louis, Mo.). The WPI gels were fabricated as described above in Example 1. Briefly, WPI powder was mixed into aqueous $CaCl_2$ solutions in varying concentrations, and vortexed to mix. Water was added to adjust to weight, and reagitated to mix. These gel precursor suspensions were cast into PTFE molds and gelled thermally at 80° C. for 60 minutes. The cylindrical gels were cooled for 10 minutes before removal from the molds, and cut into lengths for repeated samples.

The freshly-gelled samples were weighed, measured for diameter and length using microcalipers, and submerged in 0.1 M phosphate buffered saline (PBS) for 24 hours. At various times during this interval, the gels were each removed, lightly wiped with an absorbant wipe to remove excess moisture, measured for weight and dimensions, and resubmerged in PBS. A second set of gels was initially weighed and measured as before, but instead of being hydrated, was allowed to air-dry until no further mass loss was observed.

The mass and volume swelling data for each composition were normalized to the initial mass or volume of the sample and expressed as percent increase over the initial values. The normalized data for each composition were fit to a power law model ($Q=a*t^b$) using SAS statistical software. The regressions were performed using the Levenberg-Marquardt minimization algorithm, with 1 and 0.01 as initial guesses for parameters a and b, respectively. Parameter b was used to compare the swelling properties of the different gels. The data are presented as means of three replications. The convergence criterion for the objective function was set to $1 \times 10^{-6}$ in all regressions. The Wald test in SAS was used to calculate 95% confidence intervals corresponding to the regression parameters.

Figure 10A:
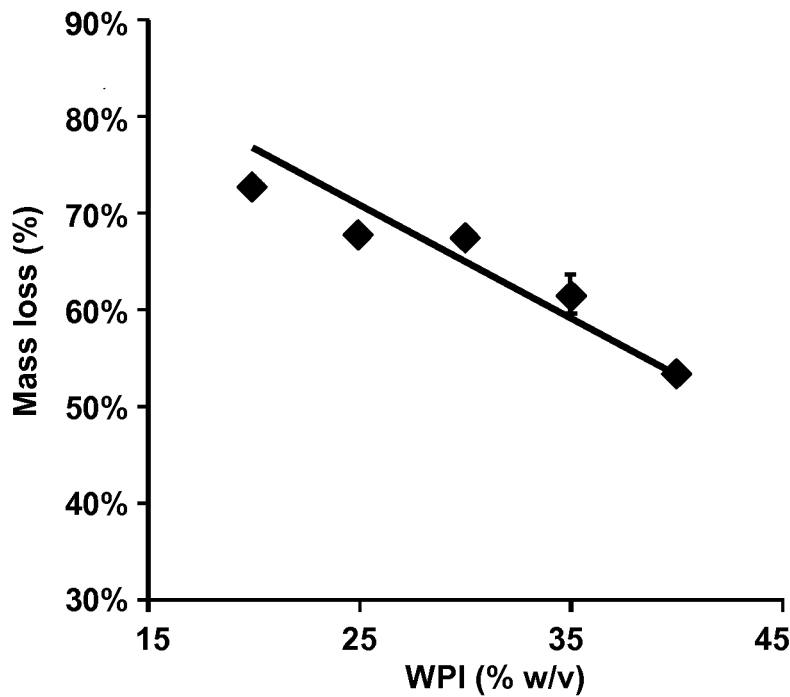
FIGS. 10A and 10B represent the initial water content in fresh gels as a function of WPI concentration. Water content is represented by both mass loss (FIG. 10A) and volume loss (FIG. 10B) upon drying. Data shown are the percent loss of the original mass or volume of the gel. The error bars represent standard deviation.
Figure 10B:
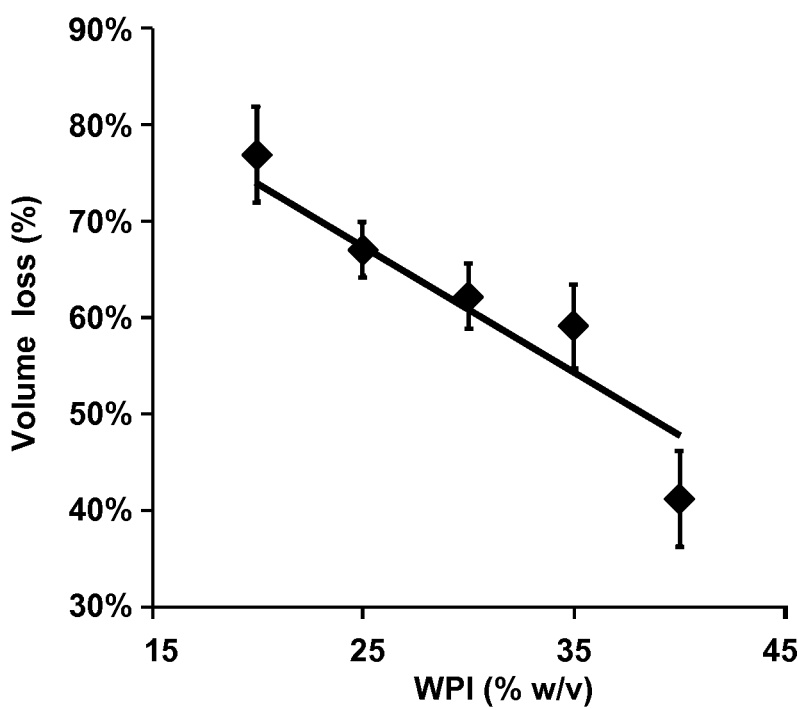

Initial Water Content: Freshly prepared gels of varying WPI concentrations were air-dried until their mass and dimensions remained constant. Initial and final mass and dimensions were recorded, and the difference was due to the evaporation of water. FIGS. 10A and 10B represent the initial water content in fresh gels as a function of WPI concentration. Water content is represented by both mass loss (FIG. 10A) and volume loss (FIG. 10B) upon drying. Data shown are the percent loss of the original mass or volume of the gel. As the WPI content of the gel increased, less water was lost since less water was initially present in the matrix. For every 1% w/v WPI added to the gel, 1.2% decreased mass loss due to drying was observed. The difference could be attributed to the slight variation in density between the WPI suspension and pure water. The volume change due to drying was greater than that of the mass. The shrinking is brought on primarily by interfacial forces acting on the inner surface of the gel. Also, in absence of water, the protein chains enter a glassy state, becoming more compact to neutralize secondary charges.

Figure 11A:
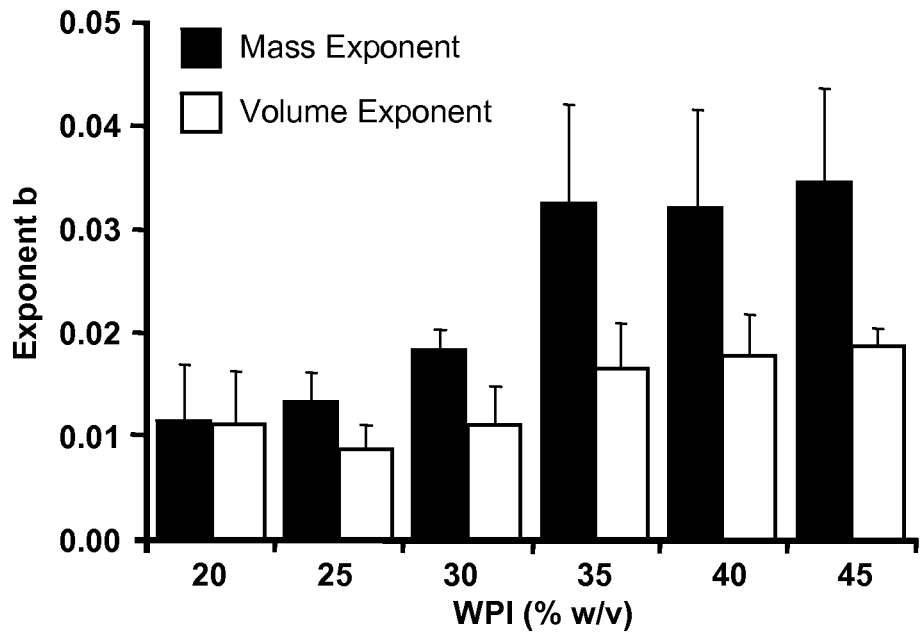
FIGS. 11A-11B show the values for the exponent b from power law regression of hydrogel swelling measurements for varying WPI concentrations (FIG. 11A) and $CaCl_2$ concentrations (FIG. 11B). The error bars represent 95% confidence intervals on the parameters.
Figure 11B:
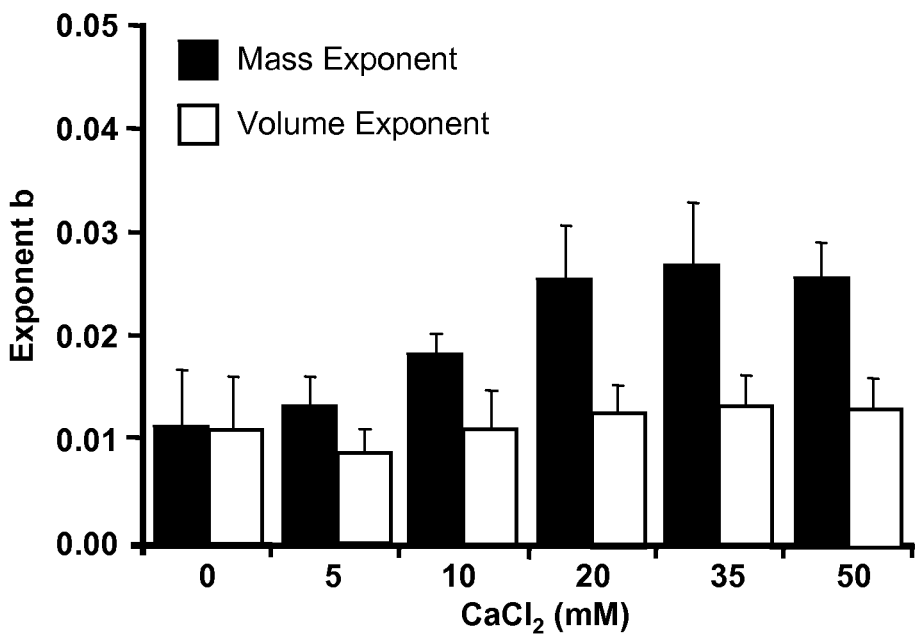

Swelling and Power Law Fits: The mass and volume data were fit to power law models to describe the swelling kinetics of each gel. The regressions were performed for the purpose of comparing exponent b for the different gels and using the information to quantitatively assess the effect that concentration had on the swelling behavior of the gels. The power law models were effective in describing the shape of the swelling curves. FIGS. 11A and 11B show the parameter values for the exponent b as a result of the mass and volume regressions. The mass-defined swelling parameter was found to be a function of WPI concentration, but the volume-defined parameter remained independent of WPI (FIG. 11A). $CaCl_2$ strongly affected the swelling parameter for both mass and volume of the gels (FIG. 11B). The value of the swelling parameter increased with $CaCl_2$ concentration, with the largest change between 10 mM and 20 mM $CaCl_2$. For concentrations between 20 mM and 50 mM, the swelling parameters remained relatively constant (FIG. 11B). For every tested composition, the mass-defined swelling parameter was higher than the volume-defined swelling parameter.

Figure 12A:
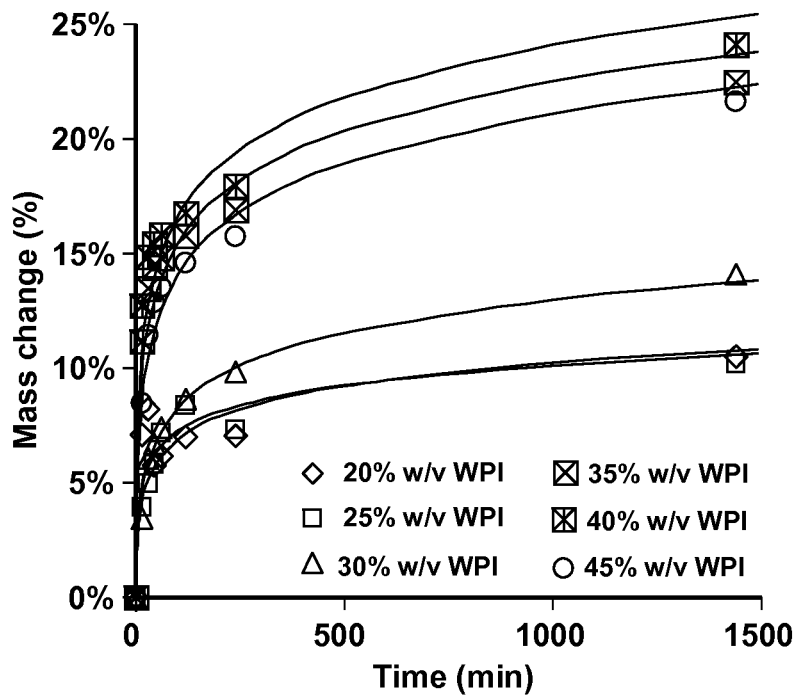
FIGS. 12A-12D show the gel swelling curves at varying WPI concentrations for mass change (FIGS. 12A and 12C) and for volume change (FIGS. 12B and 12D). Data are presented as the percent increase over initial mass or volume; curves are power-law fits to the data.
Figure 12B:
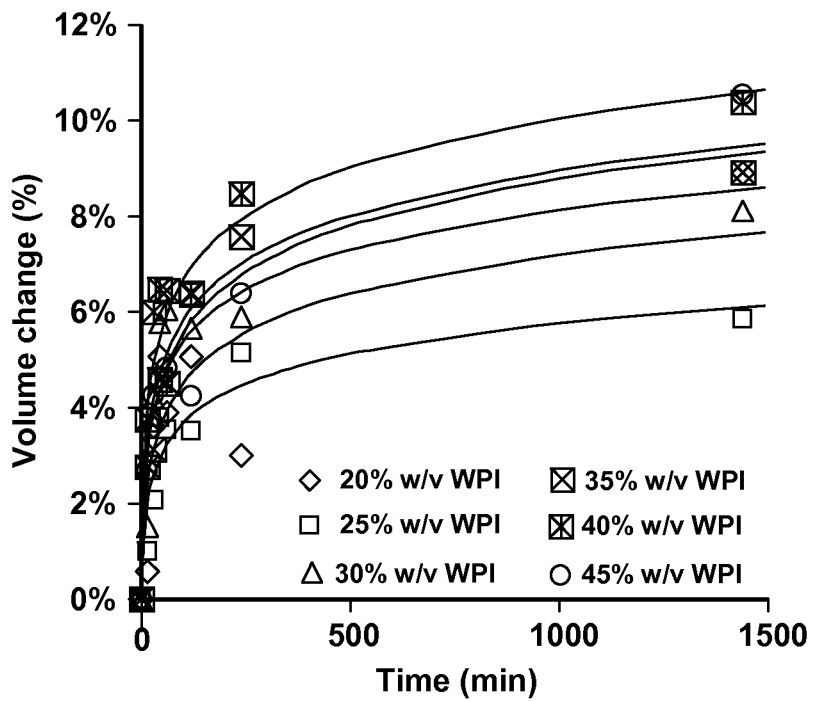
Figure 12C:
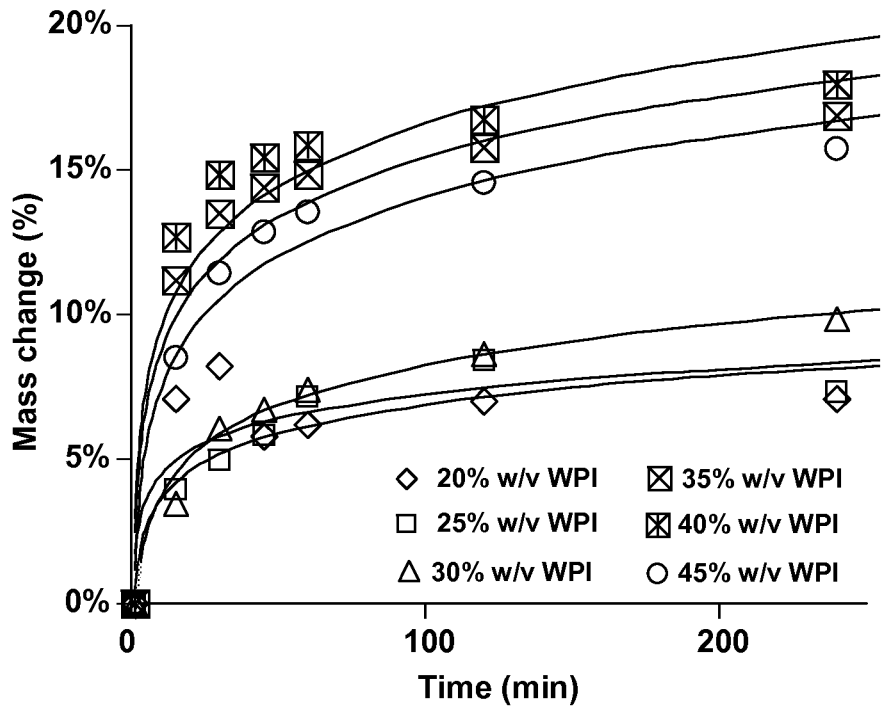
Figure 12D:
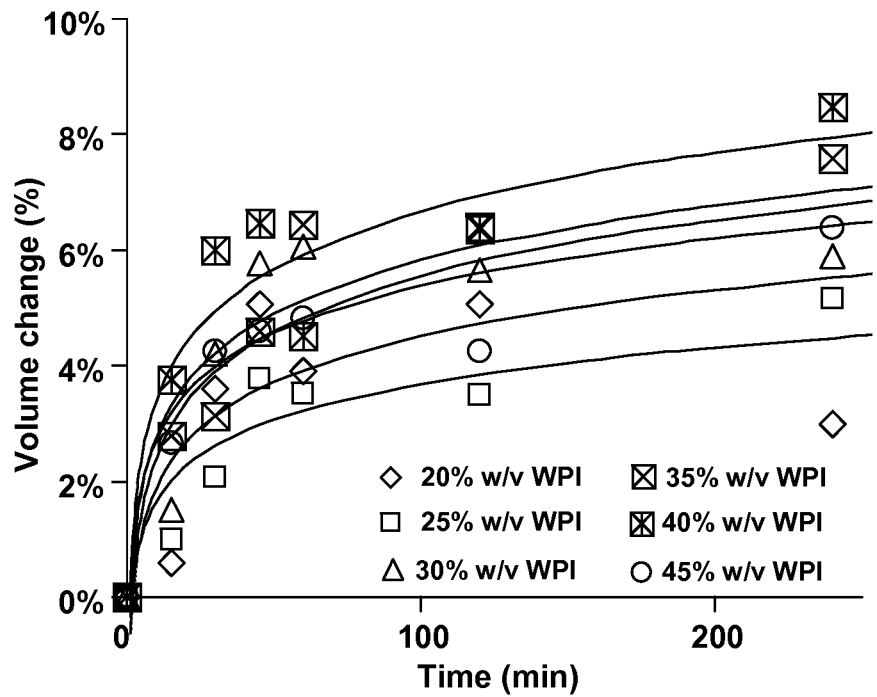

The observed swelling trend with respect to WPI concentration could be explained by several factors. FIGS. 12A-12D show the gel swelling curves at varying WPI concentrations for mass change (FIGS. 12A and 12C) and for volume change (FIGS. 12B and 12D). Data are presented as the percent increase over initial mass or volume; curves are power-law fits to the data. FIGS. 12C and 12D are expanded views of the shorter times (<250 min) of the same data shown in FIGS. 12A and 12B. At low WPI concentration, macroporosity is limited and does not greatly inflate the mass change compared to the volume change, so a wider gap is seen in the mass change for gels of 20%-30% w/v WPI vs. 35%-45% w/v WPI, than is seen for the volume change (FIGS. 12A and 12B). Overall, the degree of swelling increased with WPI concentration as a result of the increased charge density created by increasing the protein content per volume of gel. The higher charge density raises the driving force controlling the flow of water into the gel, thereby increasing the rate and degree of swelling. The crosslink density decreases the swelling by restricting the motion of protein chains. At a certain threshold protein concentration, the crosslink density is high enough to mitigate the driving force for solvent infiltration, and at 45% w/v WPI, the gel exhibits less overall swelling than gels of lower concentration.

Figure 13A:
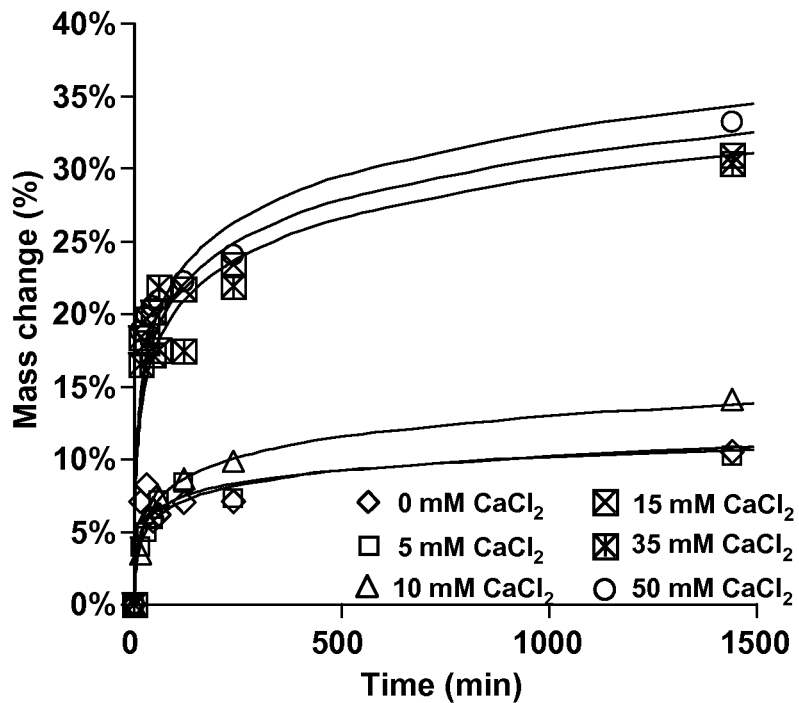
FIGS. 13A-13D show the gel swelling curves at varying $CaCl_2$ concentrations for mass change (FIGS. 13A and 13C) and for volume change (FIGS. 13B and 13D). Data are presented as the percent increase over initial mass or volume; curves are power-law fits to the data.
Figure 13B:
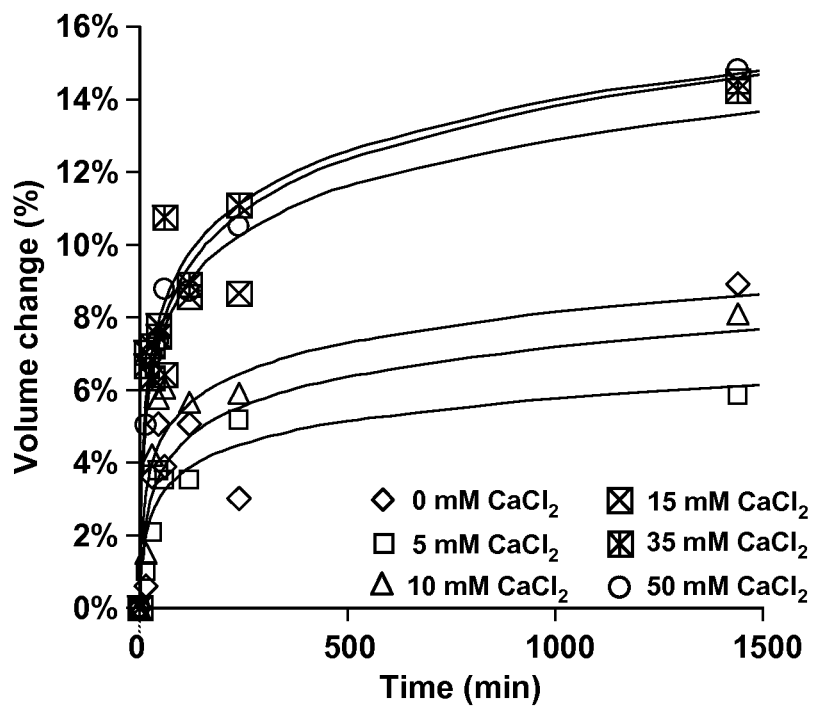
Figure 13C:
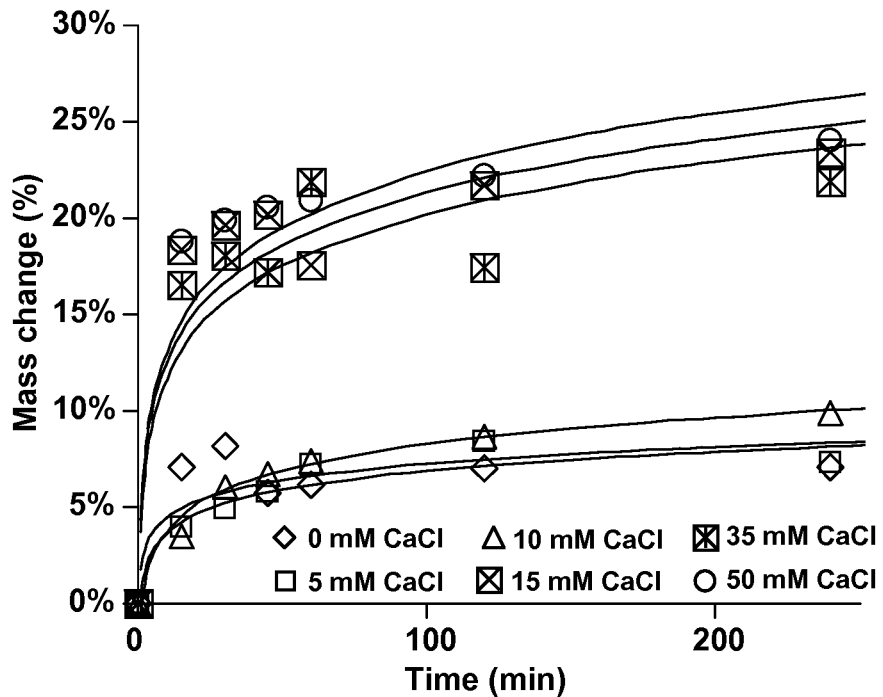
Figure 13D:
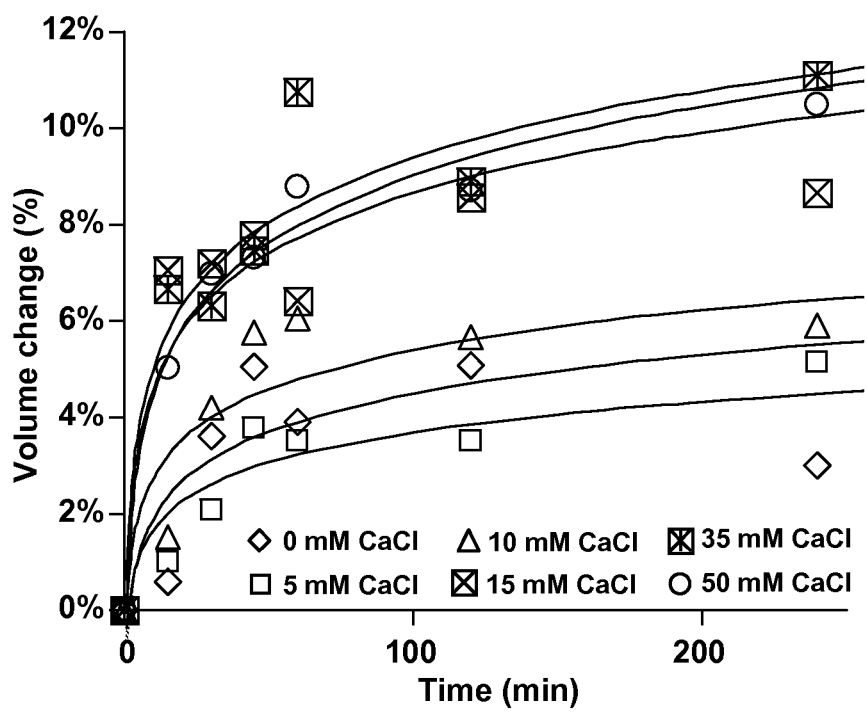

Swelling was also observed to be dependent on $CaCl_2$ concentration. FIGS. 13A-13D show the gel swelling curves at varying $CaCl_2$ concentrations for mass change (FIGS. 13A and 13C) and for volume change (FIGS. 13B and 13D). Data are presented as the percent increase over initial mass or volume; curves are power-law fits to the data. FIGS. 13C and 13D are expanded views of the shorter times (<250 min) of the same data shown in FIGS. 13A and 13B. An increased discrepancy with increased $CaCl_2$ was seen between mass-defined and volume-defined swelling (FIGS. 13A and 13B). As $CaCl_2$ was added to the matrix, the charges of calcium and chloride ions, and WPI side groups, neutralized one another, mitigating the charge gradient driving the solvent flow into the gel. This neutralization behavior likely accounts for the observed saturation in swelling parameter reached at 20 mM $CaCl_2$. Following 24 hours in buffer, the highest degree of swelling observed for a 10 mM gel was at 24.1%, corresponding to the mass of 40% w/v WPI (FIG. 12A). The highest observed volume change was 10.5%, corresponding to 45% w/v WPI (FIG. 12B). The highest degree of swelling by mass observed for a 35% w/v WPI gel was 33.2% by mass (FIG. 13A), or 14.8% by volume (FIG. 13B), both corresponding to 50 mM $CaCl_2$.

Although the swelling kinetics are relatively slow compared to some gels, use of hydrogels as bioscaffolds or fishing lures does not need a fast-response hydrogel. Furthermore, the degrees of swelling observed for the various gels appeared low within the range for common hydrogels. However, the degrees of swelling were calculated using the gelation conditions as the reference state. When the full hydration range is considered—from dry, glassy gel to fully-hydrated gel—most gels reach approximately 85% swelling in 0.1 M PBS. For the sake of reproducibility and predictability of dimensions and properties, a 2-15% change in sample dimensions is preferable to a 70-80% change.

Complete drying of the gels showed that initial water content was linearly dependent on WPI concentration and agreed well with values which would be obtained by performing a mass balance on each gel. The swelling parameters of WPI gels were characterized as a function of composition. Swelling was found to increase with increased WPI or increased $CaCl_2$ concentration. Water uptake during gel hydration caused swelling of up to 33.2% by mass and 14.8% by volume over the gelation reference state. The mass and volume changes due to hydration could be modeled by a power law. Factors controlling the swelling were determined to be the gradient in charge density between the solvent and the gel, the crosslink density, and macro- and nanoporosity of the gels. All these factors were dictated in part by the composition of the gel and led to the observed responses.

EXAMPLE 5

Polysaccharide Composites to Enhance WPI Gels

Materials and Methods. The materials used were as described above in Example 1. All water used in this work was >18 MΩ polished water from a Direct-Q® 3 water purification system (Millipore, Billerica, Mass.). The materials used were WPI powder from Davisco Foods International (Eden Prairie, Minn.); calcium chloride dihydrate from Mallinckrodt Chemicals (Hazelwood, Mo.); chitosan from Polysciences Inc. (Warrington, Pa.); cellulose, amylopectin from maize, amylose, dextran, and phosphate buffered saline solution components (NaCl, KCl, $Na_2HPO_4$, $KH_2PO_4$) from Sigma-Aldrich (St. Louis, Mo.). All materials were used as provided without further purification. Scaffold fabrication was as described above in Example 1, materials were prepared by stepwise addition of WPI powder and polysaccharide powder (amylose, amylopectin, cellulose, chitosan, or dextran) to an aqueous $CaCl_2$ solution of half the volume and double the concentration desired for the final mixture. The final compositions ranged from 20 to 45% w/v WPI, 0 to 0.25 g polysaccharide additive per g WPI, with 10 mM $CaCl_2$. The mixtures were homogenized by vortex followed by a submerged wand mixer, and adjusted to the final weight ratio by adding water to achieve the target concentration. The precursor suspension was then cast into the desired sample geometry.

The samples were loaded into custom PTFE molds manufactured in-house. The molds were constructed to generate cylinders of 7.62 cm (3 inches) in length, and 10 mm in diameter. Gelation was induced thermally by curing at 80° C. for 60 minutes. The samples were then cooled at room temperature for 10 minutes and removed from the molds. The cylinders were cut to 10 mm lengths using a diamond-blade rotating saw for an aspect ratio of 1. The finished samples were stored in PBS for 2 hours prior to testing to ensure proper hydration.

Compressive testing was performed using an Instron universal testing system (model 4411, Instron, Norwood, Mass.) at a cross-arm speed of 5 mm/min until failure. The mechanism for failure was the buckling of the gel in failure lines parallel to the direction of applied force. The load-deformation data were converted to stress-strain curves, and the failure point and initial slope of each were identified. The sets of samples were designed to test the full range of each polysaccharide composition to the processing-ability limit of the casting suspension, and subsequently, a full range of WPI concentrations forming a solid gel (20 to 45% w/v) at a constant amylopectin concentration was tested. The data were each presented as a mean±standard deviation of at least three replications per data point. Statistical significance was determined by performing a Studentized Tukey test ($\alpha=0.05$) for every pair of means in the mechanical testing data, or the Welch's t-test for comparison of amylopectin composites to naïve WPI gels.

Additive Type Effect: The different polysaccharide additives (amylose, amylopectin, cellulose, chitosan, or dextran) had varying effects on the composite material, but the predominant outcome of polysaccharide incorporation was the reduction in the strength and stiffness of the material. The compressive strength values, compressive moduli, and break strain values for the various scaffolds as a function of Additive/WPI weight ratio are presented in FIGS. 14, 15, and 16, respectively. All composites contained 35% w/v WPI and 10 mM $CaCl_2$. All sets of composites were compared to a nominal, additive-free gel. The nominal value was taken as the average between all additive-free gels. Amylopectin was the exception to the general result, exhibiting an increased compressive strength and some evidence of increased modulus at a constant WPI concentration. In contrast, the tested amylose, cellulose, chitosan and dextran additives all caused a decrease in compressive strength, and all but chitosan caused a decrease in compressive modulus. The data suggest that low chitosan concentrations slightly improve the compressive modulus. While the threshold values of compressive strength and modulus suitable for a bone regeneration scaffold are well defined, there is no agreed-upon value of deformation a scaffold should withstand before failure. The additives effected changes to the break strain of the material, but may not affect the overall quality of the scaffold. Amylopectin increased the strain at which failure occurred, and amylose tended to increase the strain. Cellulose showed little effect, and chitosan and dextran tended to make the material fail at lower deformation.

Figure 14:
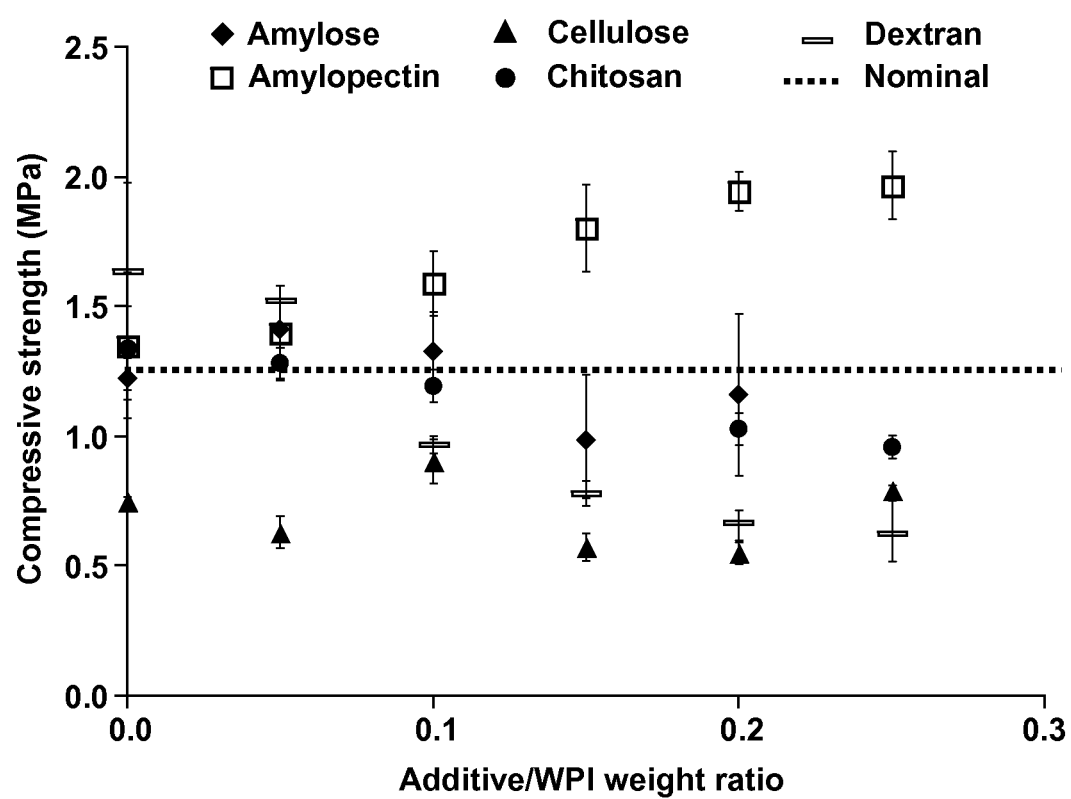
FIG. 14 illustrates the change in composite compressive strength as a function of change in additive/WPI weight ratio, for the additives of amylose, cellulose, dextran, amylopectin, and chitosan, using gels of 35% w/v WPI and 10 mM $CaCl_2$. The nominal dotted line represents the average naïve WPI gel strength.
Figure 15:
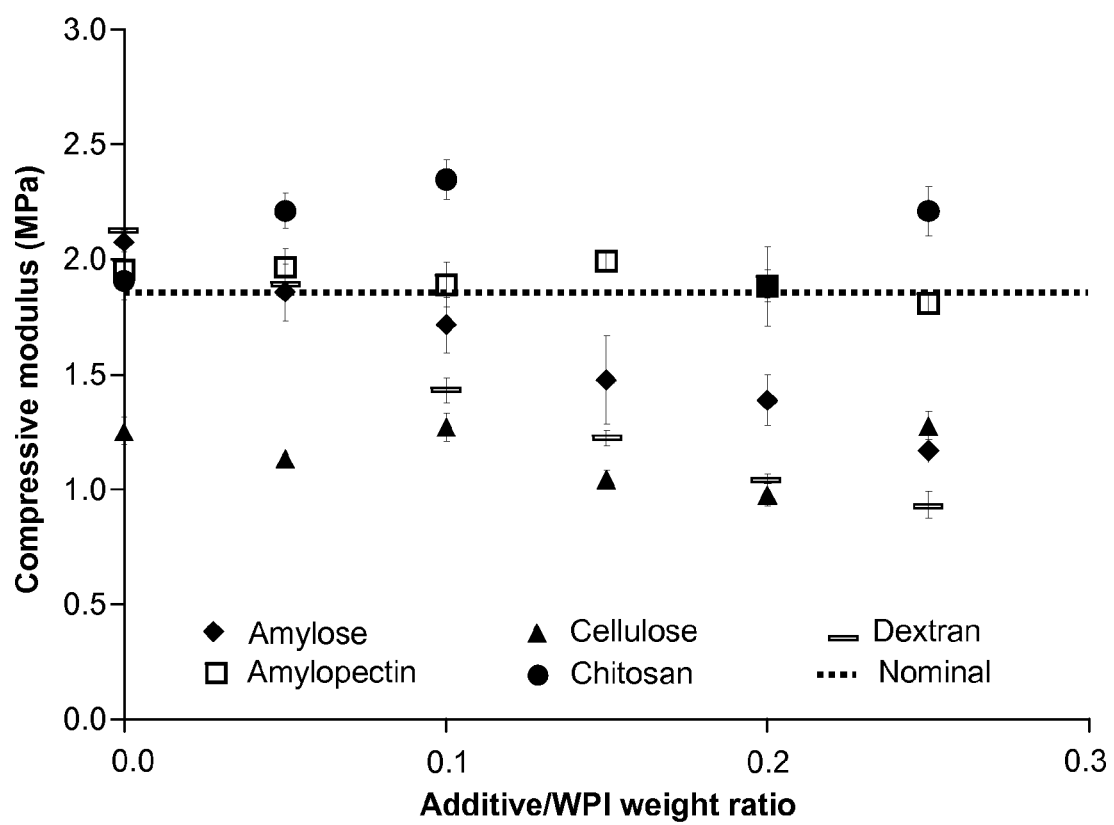
FIG. 15 illustrates the change in composite compressive modulus as a function of change in additive/WPI weight ratio, for the additives of amylose, cellulose, dextran, amylopectin, and chitosan, using gels of 35% w/v WPI and 10 mM $CaCl_2$. The nominal dotted line represents the average naïve WPI gel modulus.
Figure 16:
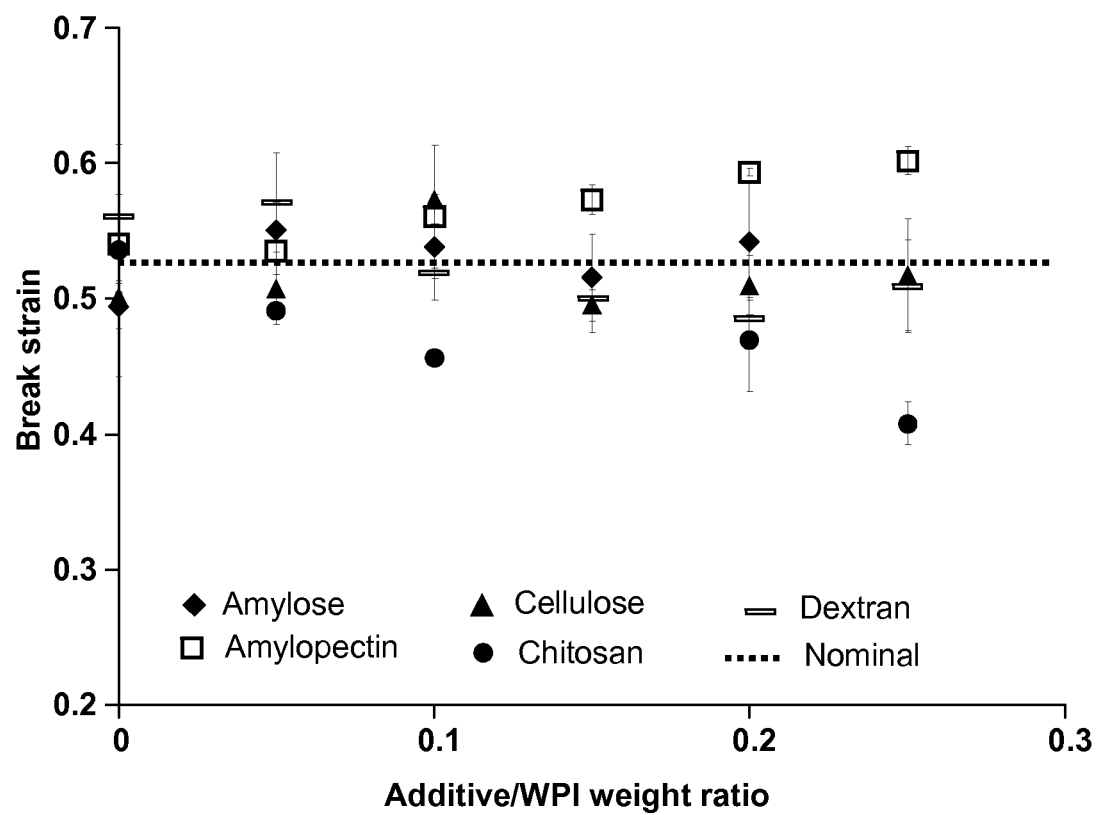
FIG. 16 illustrates the change in composite break strain as a function of change in additive/WPI weight ratio, for the additives of amylose, cellulose, dextran, amylopectin, and chitosan, using gels of 35% w/v WPI and 10 mM $CaCl_2$. The nominal dotted line represents the average naïve WPI gel break strain.

Additive Ratio Effect: The mechanical properties of each polysaccharide additive displayed a different concentration dependence. Any claim as to a trend exhibited by a set of composites is based upon 95% significance level as determined using the Tukey test. Amylose-containing composites showed a maximum strength at a ratio between 0.05 and 0.10 amylose/WPI, whereas higher ratios decreased strength below the nominal value (FIG. 14). The compressive modulus decreased proportionally with amylose/WPI ratio (FIG. 15). The strain at which failure occurred qualitatively followed the trend seen for the material strength, but all strain values exceeded the nominal value (FIG. 16).

Figure 17A:
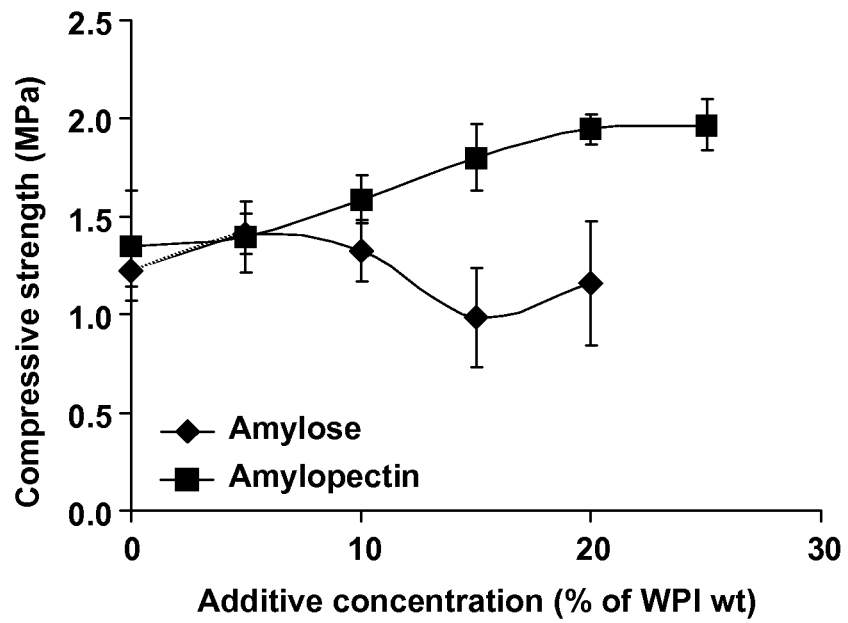
FIGS. 17A and 17B show the compressive strength (FIG. 17A) and compressive modulus (FIG. 17B) of amylose- or amylopectin-based composites with 35% w/v WPI and 10 mM $CaCl_2$.
Figure 17B:
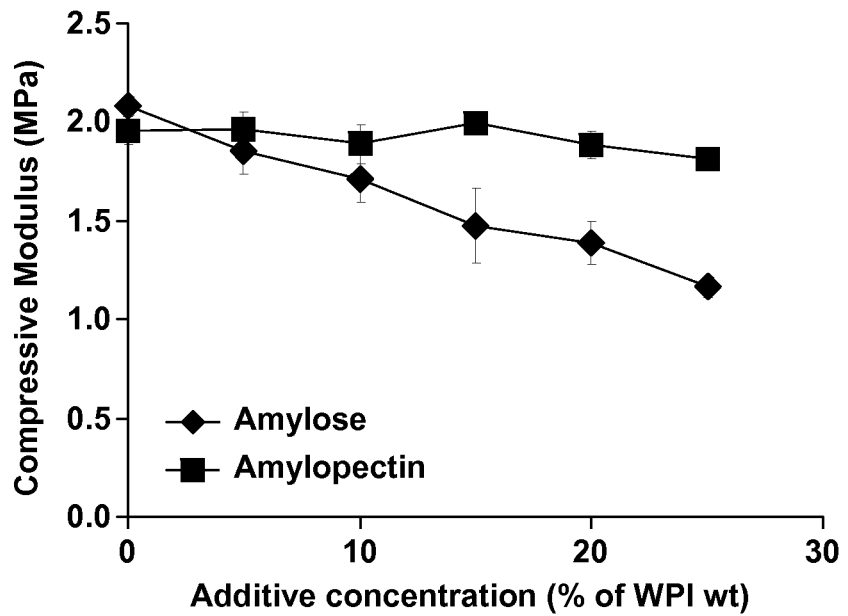

Amylopectin-containing composites with 35% w/v WPI followed a gradual sigmoidal increase in mechanical strength with increased amylopectin/WPI ratio (FIG. 14). The modulus did not exhibit a consistent pattern, but no composite had a modulus significantly higher than the nominal, while for several composites the moduli were significantly lower (FIG. 15)—a result that was later found to be anomolous in a range of protein concentrations. For amylopectin, as for amylose, the break strain was qualitatively similar in behavior to the mechanical strength. A gradual sigmoidal increase was observed and supported statistically (FIG. 16). FIGS. 17A and 17B show the compressive strength (FIG. 17A) and compressive modulus (FIG. 17B) of amylose- or amylopectin-based composites with 35% w/v WPI and 10 mM $CaCl_2$. The two starch components have an identical backbone, but very different contributions to the composite (FIGS. 17A and 17B), suggesting that the difference between them—in the highly branched structure of amylopectin—is responsible for the change.

Cellulose-containing composites effected no consistent change to the properties tested. Variations were significant, but occurred in both directions for strength (FIG. 14). The modulus also did not exhibit a predictable trend with respect to cellulose/WPI ratio, but no ratio was significantly higher than nominal, while several were significantly lower (FIG. 15). The break strain remained nearly independent of cellulose/WPI ratio save an inconsistent experimental value for 0.1 g cellulose/g WPI (FIG. 16).

Chitosan-containing composites decreased in compressive strength proportionally with chitosan/WPI ratio (FIG. 14). The modulus did not exhibit a predictable trend with respect to chitosan/WPI ratio but suggests an intermediate maximum stiffness corresponding to approximately 0.10 g chitosan/g WPI (FIG. 15). Like the mechanical strength, the break strain decreased roughly proportionally with chitosan/WPI ratio (FIG. 16).

Compressive strength decreases first rapidly, then gradually to a plateau as dextran/WPI ratio is increased (FIG. 14). The compressive modulus follows the same relationship (FIG. 15). The break strain relationship is similar if less distinctly clear than the other two properties (FIG. 16).

Figure 18A:
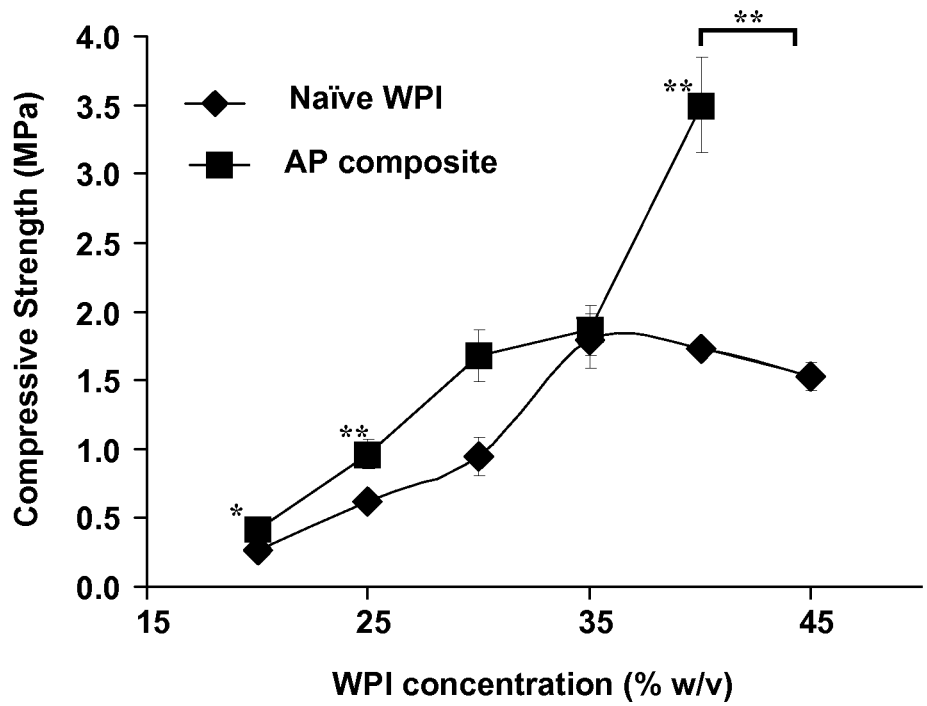
FIGS. 18A and 18B plot compressive strength and compressive modulus, respectively, as a function of WPI concentration in amylopectin-based composite as compared to naïve WPI gels that contain 10 mM $CaCl_2$ and 0.77 g amylopectin per g WPI—e.g., 0.2 g amylopectin per g WPI for 35% w/v WPI composite. The symbols correspond to difference between composite and corresponding naïve gel of significance of $p<0.05$ (*), $p<0.01$ (†), $p<0.005$ (**), $p<0.001$ (††), or $p<0.0005$ (‡).
Figure 18B:
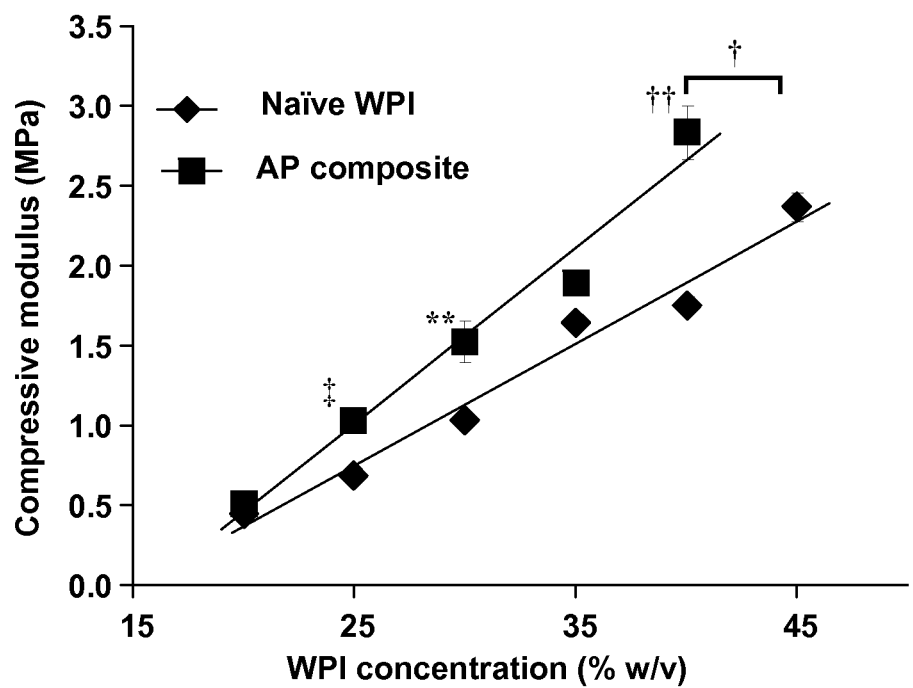

WPI Concentration Effect: As the most promising of the tested polysaccharides, amylopectin was incorporated into gels of a range of protein concentrations to determine if its effect would carry across to other concentrations. Between the two components, WPI is the one that causes a greater effect upon—and thus dominates—the mechanical properties. The compressive strength and modulus of gels with constant amylopectin concentration and varying WPI content are plotted and compared to naïve WPI gels of the same concentration in FIGS. 18A and 18B. FIG. 18A plots compressive strength and FIG. 18B plots compressive modulus as a function of WPI concentration in amylopectin-based composite as compared to naïve WPI gels that contain 10 mM $CaCl_2$ and 0.77 g amylopectin per g WPI—e.g., 0.2 g amylopectin per g WPI for 35% w/v WPI composite. Amylopectin was found to bring about a significant enhancement of the mechanical properties of the gel. An increase of as much as 100% was observed for 40% w/v WPI compressive strength, and up to 60% greater compressive modulus was observed for the same gel.

Chitosan addition showed some increase in the modulus of the material, if a decrease in mechanical strength. The cause for the behavior may stem from chitosan's backbone chemistry. A chitosan molecule contains many primary amines that become available for protein-polysaccharide interactions during and following gelation. This interaction would serve to make the gel more rigid.

Amylose and amylopectin have identical backbones, yet their contributions to the mechanical properties of the matrix in which they were dispersed were quite different (FIG. 17). The only differences in the molecular structure of the two is the high degree of branching by $\alpha(1-6)$ linkages in amylopectin which is absent in amylose. The branching of the polymer, along with molecular weight, affects its water solubility, rendering amylopectin insoluble, which could contribute to the difference in effects. However, cellulose, chitosan, and dextran are not soluble in water. None of these demonstrates the behavior of amylopectin in the matrix, so the solubility is not believed to cause the change. The branching also causes molecular crystallinity in amylopectin as compared to amylose, which is generally helical until associated. The crystalline structure adds to the stiffness of the dispersed phase and facilitates load transfer from the dispersing phase.

The applicable length scale of the additive has a great impact on the composite properties. By using the materials tested in this study in nanoparticulate form, the measured mechanical properties could be improved. Nanocomposites are known to display traits different from their conventional counterparts with a very small fraction of additive. The driving force for the change is the increased interfacial area between phases. By replacing microparticles with nanoparticles of the same material, specific surface area increases by up to three orders of magnitude. If the interaction between the dispersed phase and the matrix can be made favorable, the increased interaction can lead to enhancement of mechanical properties that cannot be achieved with conventional composites. Thus, both amylopectin and chitosan could be added as nanoparticles to increase the mechanical properties of the gel matrix into a range better for bone regeneration. Without wishing to be bound by this theory, we also believe added cellulose with compatible surface groups—in this case amine or carboxyl groups—would achieve similar results.

Composite scaffolds were fabricated using varying compositions of whey protein isolate and different polysaccharides. Amylose, amylopectin, cellulose, chitosan, and dextran were evaluated as a dispersed phase in the WPI gel matrix in conventional, particulate form. In this form, chitosan improved gel compressive modulus over the naïve gel, but detracted from the compressive strength. Amylose, cellulose, and dextran all formed composites of inferior mechanical properties to those of naïve WPI gel. Scaffolds containing amylopectin had higher compressive strength and modulus than naïve WPI gel, with up to a 100% improvement in compressive strength and up to 60% improvement in modulus in a 40% w/v WPI gel with 0.20 g amylopectin per g WPI. The best composite tested in this study had a compressive strength of 3.50±0.35 MPa and a modulus of 2.84±0.17 MPa. The best composite was 70% of the desired strength for a bone scaffold, but still one order of magnitude below the desired compressive modulus. The amylopectin composite properties were better suited for application in bone tissue regeneration requiring load-bearing capability. Amylopectin does not interfere with cell adhesion and proliferation known to occur on the naïve WPI gel surface and vital to the function of the scaffold.

EXAMPLE 6

Proliferation and Mineralization of Preosteoblasts on WPI Scaffolds for Bone Tissue Regeneration Materials and Methods: The water used in this study was polished water, with resistivity greater than 18 MΩ, from a Direct-Q® 3 water purification system (Millipore, Billeriea, Mass.). Whey protein isolate was obtained from Davisco Foods International (Eden Prairie, Minn.) and used as provided. Unless otherwise stated, all other chemicals used were obtained from Sigma-Aldrich Corporation (St. Louis, Mo.). The scaffolds consisted of thermally-induced WPI gels of varying compositions. Whey protein was mixed into aqueous solutions of calcium chloride by vortexing to form suspensions ranging from 20 to 45% w/v WPI, from 0 to 20 mM $CaCl_2$, and from 0 to 0.25 g/g WPI of amylopectin. The suspensions were poured into aluminum molds and gelation was thermally induced at 80° C. for 20 minutes in a heated press to obtain the desired thickness. The gels were then cored to the desired diameter such that each scaffold was 10 mm in diameter and 1.57 mm thick.

Prior to use, all scaffolds were sterilized by submersion in 200-proof ethanol, performed under vacuum to drive the ethanol into inner pores. The scaffolds were kept in ethanol for 5 hours under agitation, with additional vacuum drawn twice during the process. All scaffold processing after this stage was performed in an aseptic environment with sterile materials and buffers. The sterile scaffolds were rinsed with 0.1 M phosphate buffered saline (PBS), and transferred to 25 mL of PBS in 50 mL centrifuge tubes. The tubes were placed under agitation, with PBS replaced with fresh solution after 2, 4, and 6 hours, and continued under agitation overnight. This procedure removed the ethanol from the scaffolds to allow for cell growth.

In Vitro Culture: Sub-confluent MC3T3-E1, subclone 4 (ATCC, Manassas, Va.) mouse preosteoblasts were statically seeded onto the sterile WPI scaffolds to begin each time study. Complete growth medium was ascorbic acid free, α-modified essential medium supplemented with 10% fetal bovine serum, 10,000 units/mL penicillin-streptomycin, and 25 μM amphotericin B, all obtained from Invitrogen (Carlsbad, Calif.). All cells used were passage 10 or lower. The cells were removed from the culture flask with Trypsin-EDTA, then pelletted by centrifuge. The supernatant was removed and the cell pellet was resuspended in fresh growth medium.

The cell suspension (20 μl of $10^5$ cells/mL) was pipetted onto each scaffold surface and incubated for one hour at 37° C. in a 5% $CO_2$ atmosphere with 99% humidity to allow cells to adhere. Each scaffold was then rinsed with fresh medium to remove unadhered or loosely adhered cells, and supplied with 1 mL of fresh medium per scaffold. The seeded scaffolds were maintained in the wells of non-tissueculture-treated 24-well plates. The cells were grown in complete growth medium for 1, 3, 5, 7, 14, or 21 days. Fresh medium was supplied every three days in culture.

Mineralization Studies: Samples used in mineralization studies were seeded with cell suspension, 100 μl of $10^4$ cells/mL, and cultured in complete growth medium, supplemented with 50 μg/mL ascorbic acid to induce differentiation and 3.0 mM $Na_2HPO_4$ to provide a source of phosphate. The scaffolds were cultured for 28 days, with fresh medium supplied every three days.

Fluorescence Microscopy: At the end of each incubation period, the in-vitro cultured scaffolds were rinsed with PBS, then fixed with 4% paraformaldehyde solution and permeablized with 0.1% Triton™ X-100. Following fixation and permeablization the nuclei were stained with Hoescht 33258 (Invitrogen, Carlsbad, Calif.) and the samples were rinsed and placed in PBS in preparation for viewing. No viability stain was employed, as several rinses with PBS prior to fixation were assumed to remove non-viable cells loosely associated with the scaffolds. The samples were imaged by a Nikon Microphot-FXA fluorescent stereomicroscope at 10× magnification at 14 blindly-selected locations per sample, and the nuclei visible within the viewing window were counted. Images were enhanced using ImageJ for Microscopy software to increase the contrast between the signal and the background, and to suppress the light from non-specific binding of the dye (as this study was to qualitatively label the nucleus). Cell density was calculated by first dividing each cell count obtained by the known area of the viewing window. The mean of all values obtained for each sample was used as a single measurement, and at least three such independent repetitions were carried out for each data point.

Curve Fitting: The cell densities obtained from the fluorescence micrographs were converted to total cell numbers by multiplying by the surface area of each scaffold, assuming a perfectly circular two-dimensional surface. Only the top surface of each disc-shaped scaffold was considered, since the bottom surfaces of several scaffolds were viewed and shown to contain no adhered cells. The cell numbers obtained were plotted versus incubation time, and fit to each of two equations. Data for 0-14 days in culture were fit to an exponential growth model (Eq. 1), and the full data sets were fit to the Gompertz model (Eq.2), which captures the saturation behavior characteristic in the proliferation of cells on a finite growing surface in the form of a retardation constant.

$$N(t) = N_0 \exp(kt) \quad \text{(Eq. 1)}$$

$$N(t) = N_0 \exp\left[\frac{k_+}{k_-}(1 - e^{-k_- t})\right] \quad \text{(Eq. 2)}$$

N(t) is the cell density (cells per unit area) as a function of incubation time, t, with $N_0$ representing the initial cell density. The exponential growth constant is represented by k in Eq. 1 and $k_+$ in Eq. 5.2, and k in Eq. 2 is the retardation constant. SAS software was used to perform the non-linear regression. The regressions were completed using Levenberg-Marquardt minimization algorithm and tested for sensitivity to initial guess. Only stable solutions with regard to initial guess were considered reliable fits. Stability is defined as a solution shown to be independent of the initial guess values within a reasonable range. Parameters extracted from these regressions were used to characterize the contributions of the various scaffold components to the scaffold performance in supporting the adhesion and proliferation of osteoprogenitor cells.

Scanning Electron Microscopy with Energy Dispersive X-Roy Spectroscopy: Mineralization samples were imaged using an FEI Quanta 200 scanning electron microscope (SEM) coupled with energy dispersive x-ray spectroscopy (EDS) for elemental analysis to elucidate the extracellular nature of the culture. Upon reaching the end of their incubation, the samples were each rinsed with PBS, fixed with 2% gluteraldehyde/1% formaldehyde in 0.1 M PBS. The samples were then post-fixed with 0.1 M cacodylate buffer with 0.004 M glycine, dehydrated in a graded series of ethanol and dried by critical point $CO_2$. Immediately prior to imaging, the samples were mounted to SEM stages and sputter-coated with platinum. prior to imaging, the samples were mounted to SEM stages and sputter-coated with platinum. Samples were imaged under high vacuum at 10 kV or 15 kV for image capture and 15 kV for EDS analysis.

Statistical Analysis: At least three repetitions were used for each scaffold composition, with 14 images for each scaffold, similarly distributed about the scaffold to account for radial changes in cell density, but blindly selected and captured (n≥ 42). The convergence criterion for the objective function was set to $1\times10^{-4}$ in all regressions. The Wald test in SAS was used to calculate 95% confidence intervals corresponding to regression parameters.

Results—Direct Cell Count: A direct approach was used to quantitate the effect that each gel component had on the overall behavior of the tissue scaffold. Discrete cell counts were performed of cells as they were in their native state. This was shown to be a more reliable approach. We used fluorescent direct cell counts for rigorous calculation of total cell numbers on bone scaffolds. From previous experiments, viable cells on all scaffolds were expected. We used the comparison of the kinetic parameters associated with the cell growth to shed light on these differences in an objective manner.

Non-Linear Regression: Two different functions were used to model the growth since two distinct growth regimes are observed for adherent cells on a finite growth surface. So long as space and nutrients are ample, cell proliferation proceeds exponentially. This behavior characterized the system at short incubation times and low cell densities, and was modeled by a simple exponential growth model. However, as space becomes limited, intercellular communication inhibits cell division, resulting in longer doubling times and a deceleration in growth. This behavior characterized the system at long incubation times and high cell densities, and was modeled by the Gompertz function. This relation does not describe initial growth as well as the exponential growth model, but captures the deceleration in the latter saturation regime inherent to the system, whereas the exponential function is quick to diverge.

Figure 19:
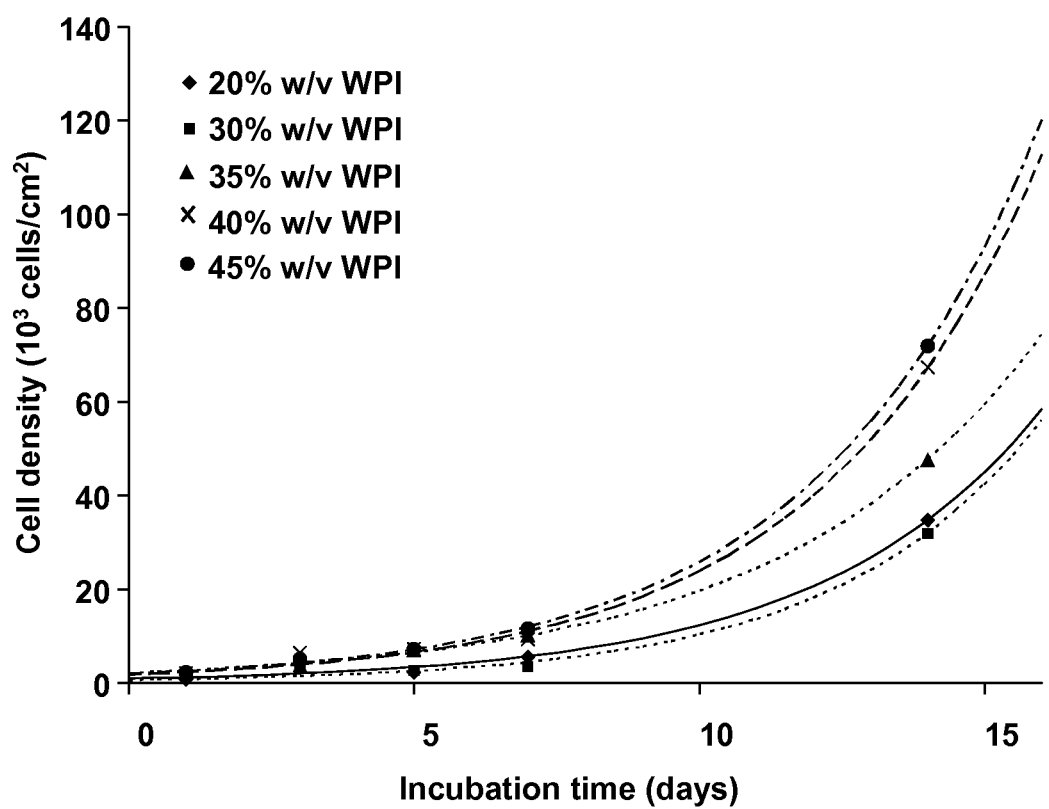
FIG. 19 illustrates the exponential growth curves based on proliferation data for MC3T3-E1, subclone 4 cells, cultured for 1-14 days on bioscaffolds containing varying scaffold concentration of WPI with 10 mM $CaCl_2$ And 0% amylopectin. The curves represent regressed fits of the data to the exponential growth model.
Figure 20:
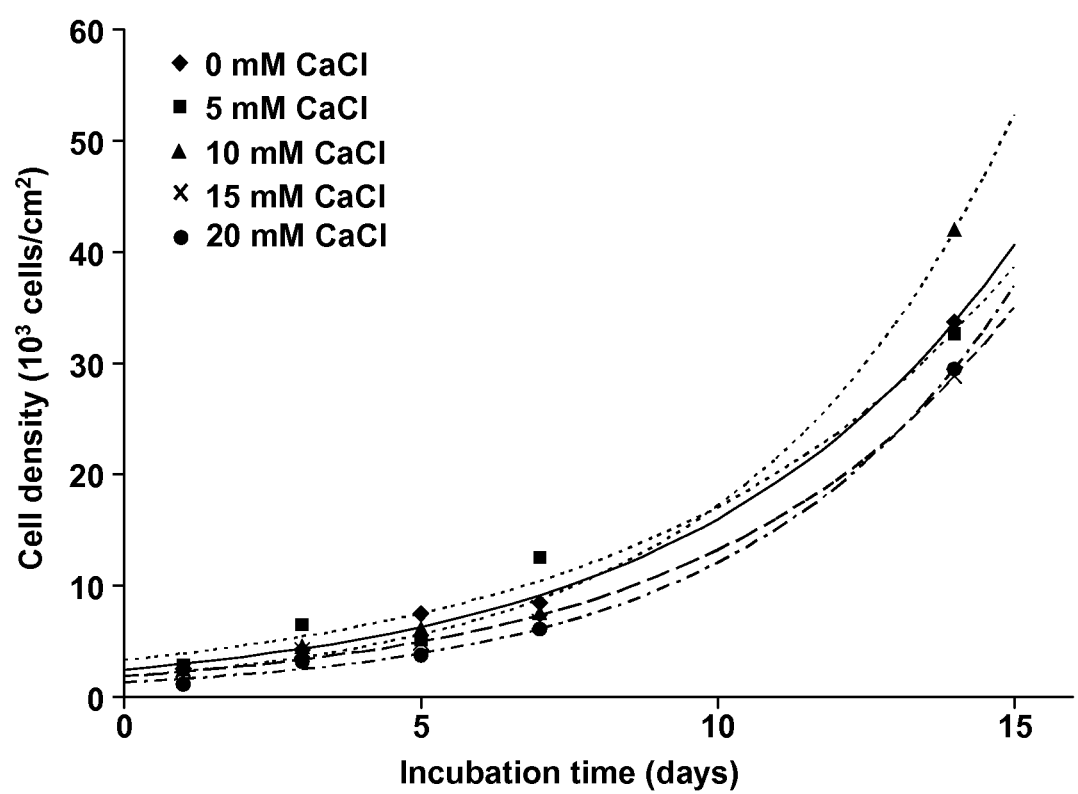
FIG. 20 illustrates represent the exponential growth curves based on proliferation data for MC3T3-E1, subclone 4 cells, cultured for 1-14 days on bioscaffolds containing varying scaffold concentration of $CaCl_2$, with 35% w/v WPI and 0% amylopectin. The curves represent regressed fits of the data to the exponential growth model.
Figure 21:
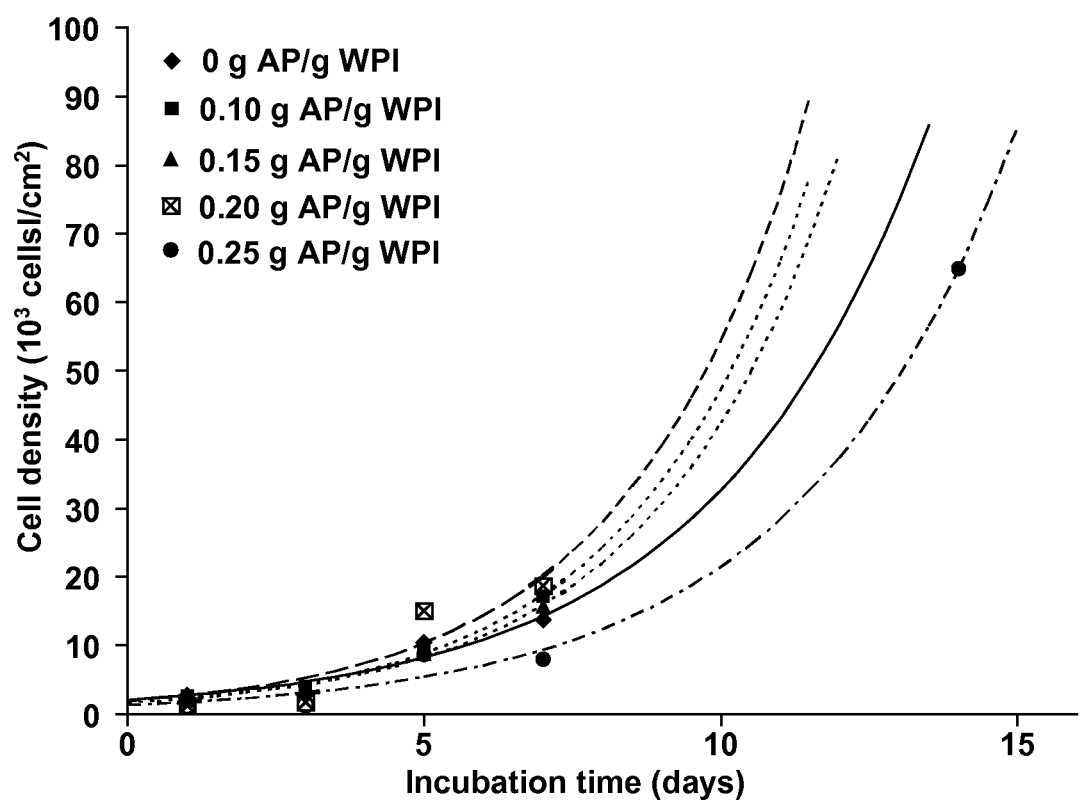
FIG. 21 illustrates the exponential growth curves based on proliferation data for MC3T3-E1, subclone 4 cells, cultured for 1-14 days on bioscaffolds containing varying scaffold concentration of amylopectin with 35% w/v WPI and 10 mM $CaCl_2$. The curves represent regressed fits of the data to the exponential growth model.

The cell density data for incubation times up to 14 days were plotted and fit to an exponential growth model. The data and exponential fits for varying concentrations of WPI, $CaCl_2$, and amylopectin are shown in FIGS. 19, 20, and 21, respectively. FIGS. 19, 20, and 21 represent the exponential growth curves based on proliferation data for MC3T3-E1, subclone 4 cells, cultured for 1-14 days on bioscaffolds containing varying scaffold concentration of WPI (FIG. 19; with 10 mM $CaCl_2$ and 0% amylopectin), $CaCl_2$ (FIG. 20, with 35% w/v WPI and 0% amylopectin), and amylopectin (FIG. 21, with 35% w/v WPI and 10 mM $CaCl_2$). The curves represent regressed fits of the data to the exponential growth model.

Figure 22:
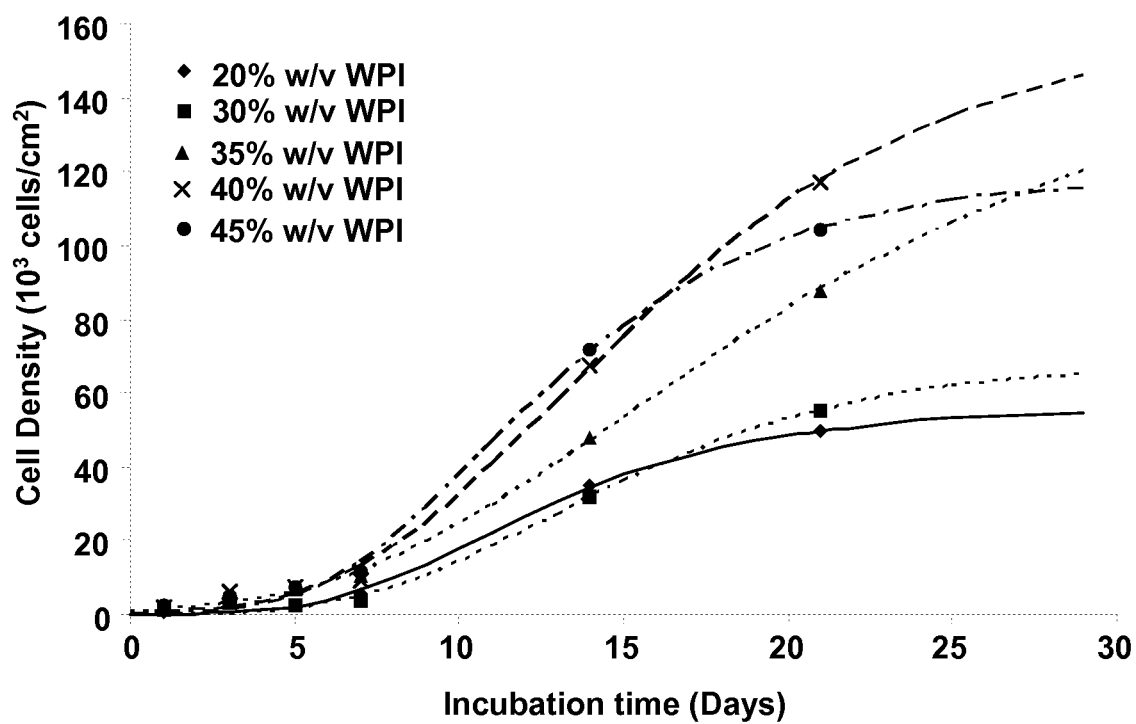
FIG. 22 illustrates the Gompertz model growth curves based on proliferation data for MC3T3-E1, subclone 4 cells, cultured for 1-21 days on bioscaffolds containing varying scaffold concentration of WPI with 10 mM $CaCl_2$ and 0% amylopectin. The curves represent regressed fits of the data to the Gompertz growth model.
Figure 23:
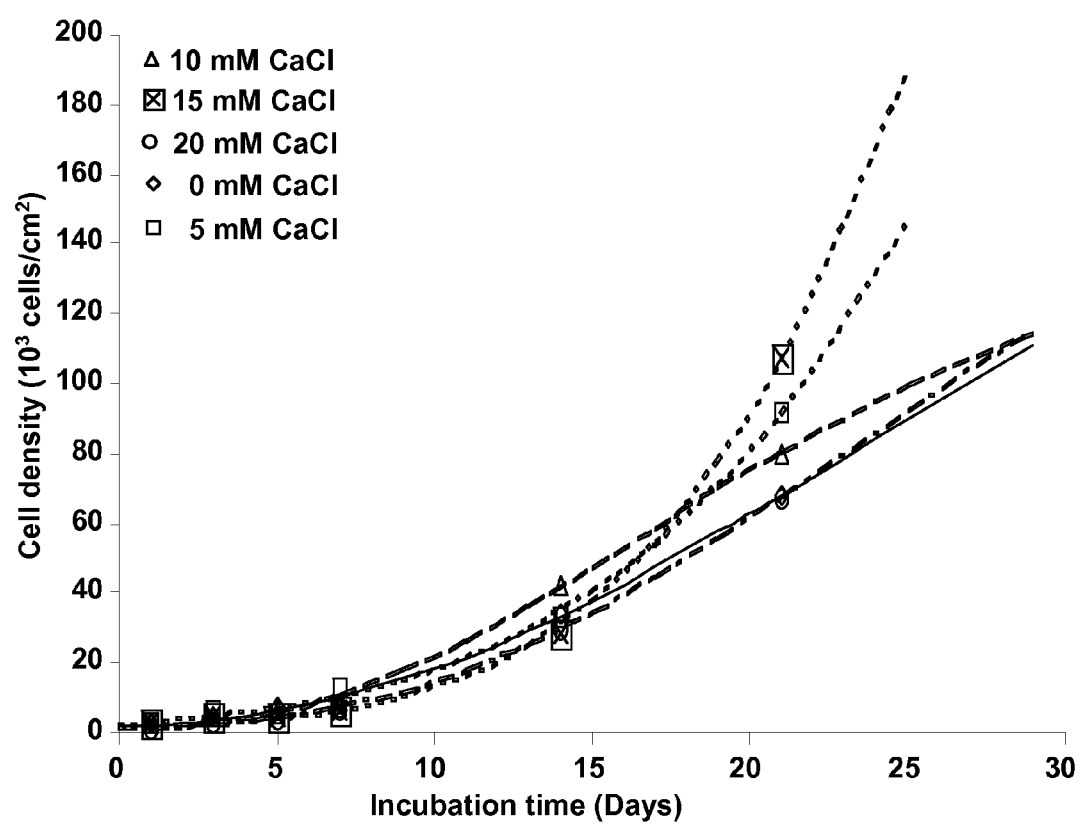
FIG. 23 illustrate the Gompertz model growth curves based on proliferation data for MC3T3-E1, subclone 4 cells, cultured for 1-21 days on bioscaffolds containing varying scaffold concentration of $CaCl_2$ with 35% w/v WPI and 0% amylopectin. The curves represent regressed fits of the data to the Gompertz growth model.
Figure 24:
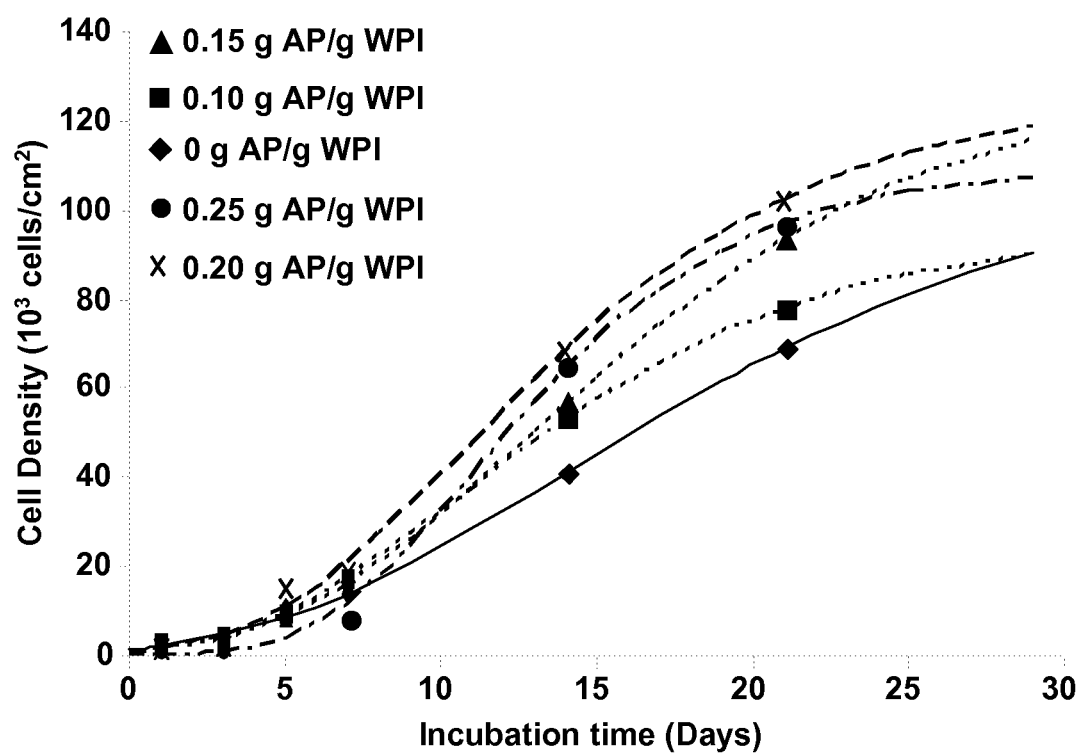
FIG. 24 illustrates the Gompertz model growth curves based on proliferation data for MC3T3-E1, subclone 4 cells, cultured for 1-21 days on bioscaffolds containing varying scaffold concentration of amylopectin with 35% w/v WPI and 10 mM $CaCl_2$. The curves represent regressed fits of the data to the Gompertz growth model.

The full set of cell proliferation data (21 days) was plotted and fit to the Gompertz function. These data and regression curves are shown for varying concentrations of WPI, $CaCl_2$, and amylopectin in FIGS. 22, 23, and 24, respectively. FIGS. 22, 23, and 24 represent the Gompertz model growth curves based on proliferation data for MC3T3-E1, subclone 4 cells, cultured for 1-21 days on bioscaffolds containing varying scaffold concentration of WPI (FIG. 22; with 10 mM $CaCl_2$ and 0%) amylopectin), $CaCl_2$ (FIG. 23, with 35% w/v WPI and 0% amylopectin), and amylopectin (FIG. 24, with 35% w/v WPI and 10 mM $CaCl_2$). The curves represent regressed fits of the data to the Gompertz growth model. The Gompertz function accurately described the growth pattern of cultures on most of the scaffolds tested.

Seeding Efficiency: The scaffolds in the study underwent static seeding with a cell suspension of 2,000 cells for one hour. The seeded scaffolds were rinsed with fresh media prior to incubation. The fraction of cells that remained adhered following the rinse was defined as the seeding efficiency. For each set of conditions, this parameter, $N_0$ in Eq. 1, was calculated from the non-linear regression of the data to the function describing exponential growth. The values for seeding efficiency onto each tested surface are listed in Table 1.

The cells adhered with high efficiency to the majority of scaffold surfaces—greater than 70% for two thirds of the tested compositions, with one third displaying greater than 80% efficiency. Additionally, scaffold composition was shown to impact the seeding efficiency. Scaffolds with low WPI content did not effect seeding as well as the higher-WPI scaffolds. At low WPI concentrations, suspended cells were unable to quickly adhere to the scaffold surface. However, with WPI concentration of 35% w/v or greater, seeding efficiency markedly increased and remained roughly constant. These higher-WPI scaffolds are stiffer than their lower-WPI counterparts—a property known as favorable to osteoblast adhesion. Strengthening this conclusion is the observed dependence of die seeding efficiency on $CaCl_2$ concentration; it mirrors previously reported results for gel stiffness with addition of $CaCl_2$ [32].

Amylopectin was not definitively found to impact the seeding efficiency, but the data nonetheless suggest an inverse relation between amylopectin concentration and seeding efficiency—also supported by the response of $N_0$ from the Gompertz model. Over the span of concentrations tested, the seeding efficiency values spanned 30%. The cause for the decreased efficiency is not believed to stem from the molecular structure of amylopectin. The structure contains multiple hydroxyl groups which should promote seeding. It is therefore more likely that it simply does not promote seeding as effectively as WPI, and the competitive effect creates the observed trend. A higher surface concentration of amylopectin leads to a lower concentration of functional groups inherent to WPI that enhance cell seeding, such as carboxylic acids, primary amines, or any adhesion moiety yet unknown. These seeding efficiencies exceeded those reported for seeding of scaffolds of collagen/hydroxyapatite (HA) [20] or PLA/calcium phosphate [21], and were achieved under more stringent seeding conditions, and comparable to those reported for centrifugal seeding of poly (ε-caprolactone-co-L-lactide) scaffolds [22].

TABLE 1

Non-Linear Regression Parameters Describing Osteoblastic Proliferation on WPI Scaffolds.

| Sample ID[a] | SE[b] (95% CI)[c] | k[d] (95% CI) (days$^{-1}$) | $k_+$[e] (95% CI) (days$^{-1}$) | k[f] (95% CI) (days$^{-1}$) | $N\infty$[g] (cells/cm$^2$) |
|---|---|---|---|---|---|
| W20/C10/A0 | 0.36 (0.10 to 0.63) | 0.259 (0.206 to 0.312) | 2.07 (0.00 to 4.30) | 0.214 (0.000 to 0.446) | 55600 |
| W25/C10/A0 | 0.24 (0.06 to 0.43) | 0.281 (0.227 to 0.336) | 1.63 (0.00 to 3.27) | 0.177 (0.000 to 0.354) | 69000 |
| W35/C10/A0 | 0.85 (0.76 to 0.93) | 0.221 (0.214 to 0.229) | 0.623 (0.420 to 0.826) | 0.112 (0.000 to 0.149) | 148000 |
| W40/C10/A0 | 0.71 (0.39 to 1.00) | 0.259 (0.226 to 0.291) | 1.10 (0.27 to 1.92) | 0.151 (0.000 to 0.264) | 159000 |
| W45/C10/A0 | 0.78 (0.68 to 0.89) | 0.256 (0.246 to 0.266) | 1.78 (0.48 to 3.08) | 0.203 (0.000 to 0.352) | 118000 |
| W35/C0/A0 | 0.97 (0.76 to 1.00) | 0.186 (0.170 to 0.203) | 0.351 (0.232 to 0.471) | 0.071 (0.000 to 0.095) | 208000 |
| W35/C5/A0 | 1.31[h] (0.72 to 1.89) | 0.163 (0.129 to 0.198) | —[i] | — | — |
| W35/C10/A0 | 0.72 (0.52 to 0.92) | 0.223 (0.203 to 0.244) | 0.589 (0.256 to 0.921) | 0.105 (0.000 to 0.165) | 148000 |
| W35/C15/A0 | 0.74 (0.58 to 0.89) | 0.195 (0.179 to 0.211) | — | — | — |
| W35/C20/A0 | 0.50 (0.40 to 0.60) | 0.224 (0.209 to 0.240) | 0.463 (0.323 to 0.602) | 0.078 (0.000 to 0.102) | 212000 |
| W35/C10/A0 | 0.81 (0.00 to 1.00) | 0.276 (0.113 to 0.439) | 0.447 (0.282 to 0.612) | 0.104 (0.065 to 0.142) | 112000 |
| W35/C10/A10 | 0.65 (0.53 to 0.77) | 0.335 (0.307 to 0.364) | 0.738 (0.629 to 0.848) | 0.150 (0.128 to 0.173) | 95800 |
| W35/C10/A15 | 0.63 (0.43 to 0.83) | 0.328 (0.278 to 0.378) | 0.684 (0.614 to 0.755) | 0.131 (0.118 to 0.145) | 130000 |
| W35/C10/A20 | 0.77 (0.00 to 1.00) | 0.333 (0.042 to 0.624) | 0.811 (0.380 to 1.243) | 0.154 (0.072 to 0.236) | 126000 |
| W35/C10/A25 | 0.53 (0.16 to 0.90) | 0.276 (0.226 to 0.328) | 1.939 (0.221 to 3.656) | 0.205 (0.023 to 0.386) | 110000 |

[a]Expressed as W(% w/v WPI)/C(mM $CaCl_2$)/A(% of WPI weight)
[b]Seeding efficiency, or fraction of adhered cells out of total seeded cells
[c]95% confidence interval by the Wald test
[d]Exponential growth constant based on cell density data for 14 days, fit to the exponential growth model
[e]Exponential growth constant based on cell density data for 21 days, fit to the Gompertz growth model
[f]Rate of retardation constant based on cell density data for 21 days, fit to the Gompertz growth model
[g]Theoretical scaffold saturation limit, predicted by the Gompertz growth model as time approaches infinity
[h]Anomalous value of efficiency, calculated as greater than 100%. Should be considered only qualitatively, in comparison to surrounding values
[i]Missing values for scaffolds for which convergence could not be reached for the Gompertz function Exponential Growth Rate Constant: The growth rate constants (k in Eq. 1) were obtained from fitting the data to an exponential growth model and are listed in Table 1. Based on the model, scaffold composition had little effect on the growth rate constant. Changing the WPI content had no impact on the growth rates on the scaffolds. WPI content was not expected to affect the growth rate, since the local environment detected by each cell could be considered saturated with WPI and therefore constant—resulting in a relatively constant growth rate. Likewise, the rate constant varied little with respect to $CaCl_2$. Although some upward variation was observed, a distinct trend could not be determined with statistical certainty. Calcium chloride added to the matrix increases surface roughness on the micrometer scale, likely to promote adhesion. The results of the study of amylopectin concentration were more complex. The comparison among the different concentrations could not be made, as four of the five scaffold concentrations tested exhibited a departure from exponential growth after only seven days—allowing only four data points to be used for the model regression. However, the highest-concentration data (0.25 g/g WPI) could be fit reliably to the 14-day data but not to the 7-day data. Because the true departure from exponential growth occurs somewhere between the two, the parameters extracted from the different fits could not be directly compared. Thus, conclusions regarding the effects of amylopectin on cell proliferation were based on the assessment afforded by the full-range fit to the Gompertz model.

Gompertz Function Rate Constants: The fit to the Gompertz function was valuable in determining primarily two parameters—the growth rate constant, $k_+$, and the rate of retardation constant, $k_-$. The remaining parameter included in the model—representing the initial cell density—was not used. After 21 days in culture, 13 of the 15 scaffolds showed an approach to scaffold saturation, and decelerating cell proliferation. Two curves could not be fit to the Gompertz model, since they were still primarily characterized by exponential growth, and there was insufficient data to converge on a single solution for the saturation value of the scaffold. The outcome merely indicates that over 21 days, proliferation of these cultures is still well characterized by the exponential function.

The growth rate constant $k_+$ and rate of retardation constant $k_-$ obtained for each set of conditions are listed in Table 1. The growth rate constant, $k_+$, represents a parameter similar to the rate constant obtained from the exponential growth fit. For WPI as well as for $CaCl_2$, no trend could be established for this parameter. While an observational trend occurred when WPI was varied, with a minimum rate at 35% w/v WPI, it could not be validated statistically. Two of the scaffold compositions in the calcium chloride data set still exhibited exponential growth at the end of the experiment, and could not be fit to the Gompertz function, leaving insufficient data to establish a trend. As amylopectin concentration was increased, the data suggest an increased growth rate, but the trend could not be confirmed beyond the model uncertainty. The phenomenon may be a result of the added nutrient source available to proliferating cells. This branched carbohydrate is composed of glucose monomers and can be hydrolyzed to release glucose molecules for consumption.

For all compositions, the response of $k_-$ to composition was qualitatively similar to that of $k_+$. The uncertainty in the regression parameters obscured any trend with respect to WPI As with $k_+$, the three regressions were insufficient to establish a trend for $k_-$ with respect to $CaCl_2$ concentration. With increased amylopectin concentration in the scaffolds, the overall suggested trend was an increase in the value of $k_-$. For each growth curve, the limit of the Gompertz function as time approaches infinity was calculated. The value of the limit corresponds to a theoretical saturation cell density on the scaffold. These values are listed as $N_\infty$ in Table 1. While varied, the theoretical saturation densities did not exhibit any compositional dependence. For all tested compositions—spanning the full possible compositional ranges—the cultures thrived upon the scaffold surface and exhibited exponential growth for as long as growth area was available, and increasing cell numbers for the length of the study.

Figure 25A:
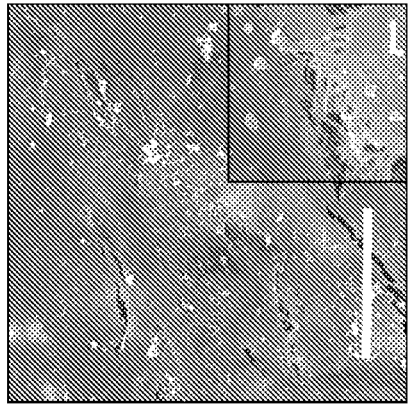
FIGS. 25A-F are SEM micrographs and elemental analysis of mineralized scaffolds.
Figure 25B:
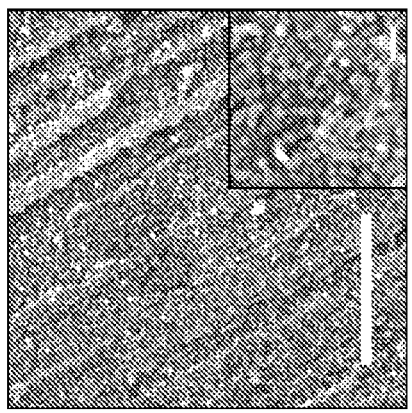
Figure 25C:
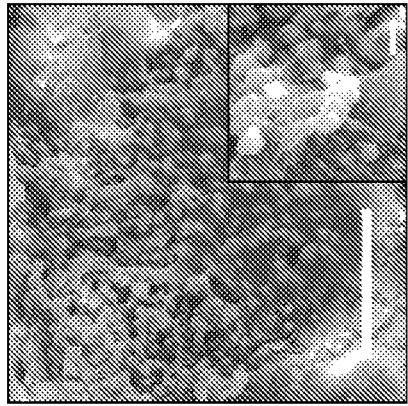
Figure 25D:
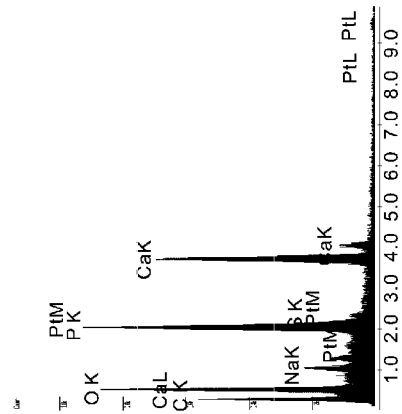
Figure 25E:
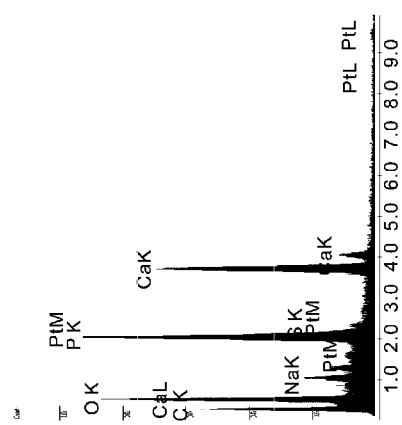
Figure 25F:
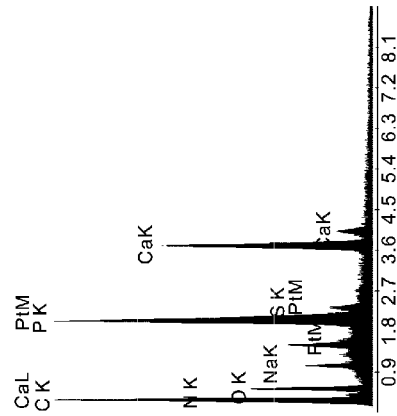

Scaffold Mineralization: It is shown in the representative micrograph in FIGS. 25A-F that after 28 days in culture, the scaffolds were fully confluent, and that the cells had differentiated and begun to lay down a mineralized matrix. FIGS. 25A-C show SEM micrographs of mineralized scaffolds with FIG. 25A showing MC3T3-E1, subclone 4 cells on a scaffold containing 35% w/v WPI scaffolds. FIG. 25B showing an acellular scaffold containing 45% w/v WPI, and FIG. 25C showing a subclone 24 (non-differentiating) cells on a scaffold containing 20% w/v WPI—all cultured for 28 days in mineralization medium. The scale bar in the figure represents 20 μm; and the inlay bar represents 2 μm. FIGS. 25D-25F show the elemental analysis of the mineralized scaffolds using EDS spectra and showing the analysis for the cells of FIG. 25A (FIG. 25D), FIG. 25B (FIG. 25E) and FIG. 25C (FIG. 25F), respectively. The x axis represents energy in keV, and the y axis represents intensity in counts. The x-ray microanalysis showed a prevalent calcium and phosphorus content, indicating a calcium phosphate phase over the scaffold (FIG. 25D). It was likewise found that acellular scaffolds cultured under the same conditions developed a calcium phosphate layer on the surface (FIGS. 25B and 25D), which points to a pre-treatment possibility. When a non-differentiating subclone of MC3T3-E1 cells was cultured under the same conditions, no calcium phosphate phase could be detected, although the culture itself thrived and fully populated the surface (FIGS. 25C and 25F).

The analysis of the scaffolds containing 0 mM $CaCl_2$ makes evident that this matrix component actively provides the calcium necessary for mineralization, and the nominal 1.8 mM $Ca^{2+}$ ions present in the mineralization medium is not sufficient for bone formation. No additional calcium source was provided in this study in order to elucidate this contribution. FIGS. 26A-D show SEM micrographs of 35% w/v WPI mineralized scaffolds with FIG. 26A showing MC3T3-E1, subclone 4 cells on a scaffold with 0 mM $CaCl_2$. FIG. 26B showing an acellular scaffold containing with 0 mM $CaCl_2$. FIG. 26C showing MC3T3-E1, subclone 4 cells on a scaffold with 20 mM $CaCl_2$, and 26D showing an acellular scaffold containing with 20 mM $CaCl_2$, —all cultured for 28 days in mineralization medium. The scale bar in the figure represents 50 μm; and the inlay bar represents 2 μm. FIGS. 26E-26H show the elemental analysis of the mineralized scaffolds using EDS spectra and showing the analysis for the cells of FIG. 26A (FIG. 25E), FIG. 26B (FIG. 26F), FIG. 26C (FIG. 26G), and FIG. 25D (FIG. 25H), respectively. The X axis represents energy in keV, and the y axis represents intensity in counts. The cells grown on the scaffold did not produce any mineral layer, and no calcium phosphate precipitation took place on the surface of the acellular scaffold (FIGS. 26A, 26B, 26E and 26F). As expected, no calcium phosphate was found on the scaffold surface with the non-mineralizing subclone. When high levels of calcium were incorporated into the scaffold, extensive mineralization resulted on the acellular scaffolds (FIGS. 26D and 26H), though mineralization on the cell growth surface was limited (FIGS. 26C and 26G).

The effects of the use of amylopectin as a scaffold additive on the mineralization process are summarized in FIGS. 27A-G. FIGS. 27A-27D are SEM micrographs of mineralized scaffolds of varying amylopectin concentration using scaffolds of 35% w/v WPI and 10 mM $CaCl_2$ scaffolds with FIG. 27A showing a scaffold containing 0.05 g amylopectin per g WPI with MC3T3-E1, subclone 4 cells. FIG. 27B showing a scaffold with acellular, containing 0 g amylopectin per g WPI, FIG. 27C showing a scaffold containing 0.25 g amylopectin per g WPI with subclone 4 (differentiating) cells, and FIG. 27D showing a scaffold containing 0.25 g amylopectin per g WPI with subclone 24 (non-differentiating) cells—all cultured for 28 days in mineralization medium. The scale bar represents 50 µm; and the inlay scale bar represents 5 µm. FIGS. 27E-27H show the EDS spectra with elemental analysis of FIG. 27A (FIG. 27D), FIG. 27B (FIG. 27E), FIG. 27C (FIG. 27G) and FIG. 27D (FIG. 27H). X axis represents energy in keV; y axis represents intensity in counts. No adverse impact was found with amylopectin, and by qualitative analysis, scaffold mineralization was carried on uninhibited. High levels of calcium and phosphorous were found on acellular scaffolds of both low (FIGS. 27B and 27F) and high amylopectin concentrations (not shown), and for the differentiating-cell-populated scaffolds of both compositions (FIGS. 27A, 27C, 27E and 27G). Once again, the scaffolds cultured with the non-mineralizing subclones showed only trace concentrations of calcium and phosphorous (FIGS. 27D and 27H).

This marks the first bone-formation event on the surface of a whey protein gel. The results show that the proposed scaffold material supports the formation of a mineralized scaffold, and implicitly, the differentiation of the model preosteoblastic cell line into osteoblasts. Notably, mineralization occurred at nominal calcium ion levels—without added calcium above that already present in the complete growth medium. Without wishing to be bound by this theory, we believe that the calcium from the scaffold matrix itself was drawn upon in order to form a calcium phosphate phase. In addition, the mouse preosteoblasts growing on the WPI scaffold were found to have actin filaments that were aligned oriented to the cells, a proper morphology for tissue formation.

Culturing scaffolds that contained 0 mM $CaCl_2$ in mineralization conditions proved that these nominal calcium ion levels—1.8 mM $CaCl_2$ present in the growth medium—are sufficient to enable active mineralization by differentiated osteoblasts but not mineralization by deposition onto acellular scaffolds, although mineralized areas were more prevalent on calcium-containing scaffolds. The scaffolds found successful in this study achieved a level of cellular mineralization comparable to that of other scaffolds, known for their potential in bone regeneration.

The concentration of WPI in die scaffold did not exhibit a qualitative difference in achieving mineralization on the scaffold surface. Mineralization was found to proceed uninhibited in the presence of amylopectin in the gel matrix. Amylopectin has several beneficial contributions to the properties of the scaffold-cell system, such as increased compressive strength and modulus and increased kinetic growth rate of cultured cells. It is therefore important that it presents no adverse impact on mineralization.

The morphology of the acellular scaffolds varied with composition. The structures of scaffolds containing 0 or 10 mM $CaCl_2$ showed a highly regular linear pattern over the full range of the scaffold (FIGS. 25B and 26B). This was attributed to the microscopic structure of the aluminum molds the gel was cast from. When $CaCl_2$ content was doubled, or when a high level of amylopectin was incorporated into the matrix, this pattern was no longer exhibited (FIGS. 26D and 27B, respectively). The difference is believed to be the effect of the composition on the scaffold degradation rate. At 20 mM, the scaffold is below its peak strength, and less stiff than at lower salt concentration. Both could contribute to enhanced degradation. Amylopectin, on the other hand, increases both the compressive strength and modulus of the gel (results not shown), but it may cause irregularities in the matrix that promote degradation. The results of this analysis above demonstrate the suitability of WPI for use as a bone tissue regeneration scaffold based on the cellular-interaction characteristics required of such a device.

In the two-dimensional in vitro experiments performed, the MC3T3-E1 (mouse preosteoblasts) cells showed a high affinity towards the naïve WPI gels as well as the composites containing amylopectin. The cells adhered with high efficiency by static seeding in short seeding times (1 hour), with enough force to survive a subsequent rinse prior to incubation. After a short incubation, they displayed the desired flat, stellate morphology indicating high-quality adhesion to the surface. The cells were found to remain viable for long-term incubation (3 and 4 weeks in culture). On all tested gel surfaces—spanning the feasible range of compositions—the cells exhibited exponential growth kinetics until saturation of the scaffold occurred. Generally, the cell density data were well-described by an exponential growth model for growth up to 14 days, and by the more complex Gompertz function for growth up to 21 days, where deceleration of growth caused by scaffold saturation took place. The proliferation kinetics depended to a degree on scaffold compositions. Seeding efficiency was enhanced by scaffold concentrations of at least 35% w/v WPI and 0-10 mM $CaCl_2$. The growth rate constants were roughly independent of composition, with a suggested increased rate for increasing $CaCl_2$ and amylopectin concentration. The rate of retardation constant did not exhibit a compositional dependence. When provided with ascorbic acid to induce differentiation and an inorganic phosphate source, the cells were able to form a mineralized extracellular matrix during a 28-day culture period.

Calcium and phosphorous were detected on all acellular scaffolds initially containing calcium in the matrix, indicating the deposition of a calcium phosphate layer on the surface. Saturation of almost all seeded scaffolds was reached during the 28-day period, and scaffolds seeded with the differentiating subclone of the cell line showed mineralized ECM, though only sporadic mineralization was seen on surfaces containing 0 mM $CaCl_2$. This indicated that the calcium source built into the matrix aided in scaffold mineralization. Scaffolds seeded with non-mineralizing subclones served as negative controls and showed no evidence of calcium phosphate formation, though the cultures thrived on the WPI and composite surfaces. The proliferation and mineralization behavior of the WPI scaffolds were found to be suitable for use in bone regeneration. All tested scaffolds supported both proliferation and mineralization (and implicitly, osteoblastic differentiation) of progenitor cells. The optimal cellular behavior was observed for scaffolds contained high WPI, low-to-medium $CaCl_2$, and high amylopectin concentrations.

EXAMPLE 7

WPI Concentration Effects on Gel Pore Structure

Porosity and pore network characteristics are among the most important properties in tissue engineering for dictating the level of success of a scaffold. Whey protein isolate (WPI) gels of different concentrations were analyzed for porosity and pore network structure using x-ray microcomputed tomography (XMCT).

Materials and Methods: All water used in this work was >18 MΩ water from a Direct-Q® 3 water purification system (Millipore, Billerica, Mass.), and the source of WPI powder, calcium chloride dihydrate and sodium azide were as described above. Samples were prepared as described above. Briefly, WPI powder was added to an aqueous $CaCl_2$ solution of half the volume and double the concentration desired for the final mixture. Sodium azide, 0.2%, was added to the suspension as a preservative. The mixtures were each vortexed to mix and allowed to equilibrate overnight. They were then adjusted to volume for the final target concentrations of 20%, 35%, and 45% w/v WPI by adding water and gently agitating. The precursor suspension was cast into cylinders (L=7.62 cm, D=10 mm) and gelation was thermally induced by curing at 80° C. for 60 min. The solid gels were cooled at room temperature and kept in a moist, sealed environment at room temperature to maintain the gel structure until testing. The three gel samples are hereafter referred to as 20WPI, 35WPI, and 45WPI.

Microtomography: X-ray microfocus computed tomography was used to create high resolution images comprised of cubic voxels (or 3D pixels), which were 14.59 μm on an edge. XMCT data were collected, processed, and segmented by Dr. Allen H. Reed at the Naval Research Laboratory, Stennis Space Center. The x-rays projections were analyzed and converted to two-dimensional grayscale (16-bit) images. Because the 2D images that are produced are perfectly registered along the length, or z-axis, of the material, a 3D image was readily obtained by stacking the slices (Data not shown). This technique is fully described in Dvora, 2010. The 3D image was used to analyze for pore distribution and pore network structure as described in Dvora 2010.

Viscometry: Viscosities of WPI suspensions from 20% to 45%) w/v WPI in water were measured using a cone and plate rheometer (Rheometric SR-5000N, Piscataway, N.J.) at shear rates ranging between 0.1 and 50 $s^{-1}$, as appropriate for each suspension. The shear rates tested varied with suspension viscosity. The viscosity dependence on WPI concentration was used in subsequent calculations to describe the pore network structure derived from entrapped bubbles in the precursor suspensions.

Figure 28A:
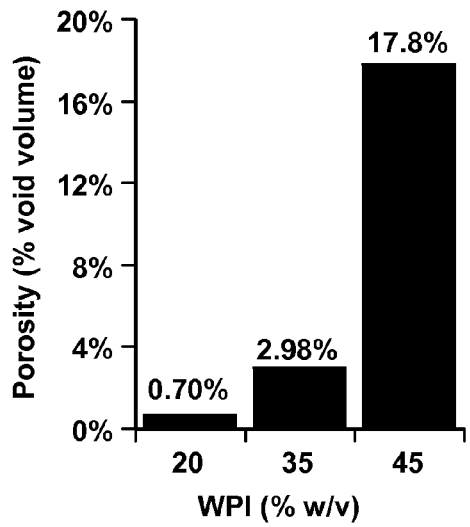
FIGS. 28A-28D shows mean bulk values for 20%, 35%, and 45% w/v WPI gels as obtained by analysis of XMCT data for the following properties.
Figure 28B:
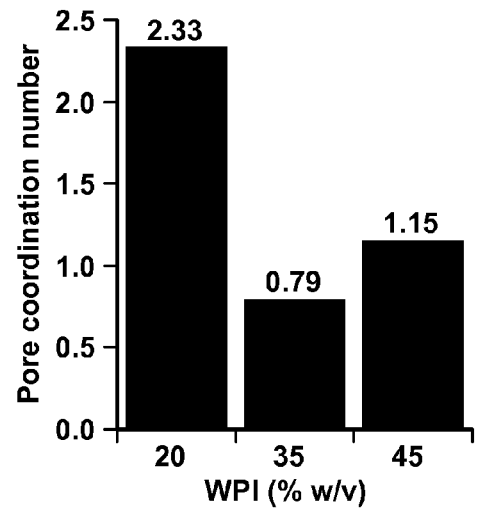
Figure 28C:
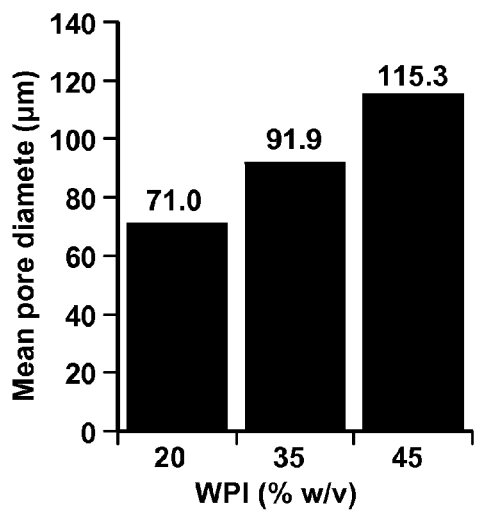

Results—Pore Distribution: Three WPI gel samples were analyzed by XMCT and a full 3D mapping of each sample was constructed. This voxel map included every pore within the solid and from it several key properties of the pore network were determined. FIGS. 28A-28D shows mean bulk values for the following properties of the 20WPI, 35WPI and 45WPI gels: FIG. 28A, porosity; FIG. 28B, pore coordination number; FIG. 28C, pore diameter; and FIG. 28D, throat diameter. As shown in FIG. 28A, porosity showed strong dependence on WPI concentration. The greatest porosity achieved was 17.8%, observed for 45WPI, while only nominal void volume was observed for 20WPI. Additionally, the small void content found in 20WPI was primarily located in a cluster of large pores at the outer edge of the sample (data not shown). The porosity was also evaluated for variation with respect to spatial position—both radially and axially within each sample. No characteristic of the pore network structure expressed any discernable trend along the axial direction. However, for the two porous samples, the porosity was higher in the center of the cylindrical sample and decreased radially.

Figure 28D:
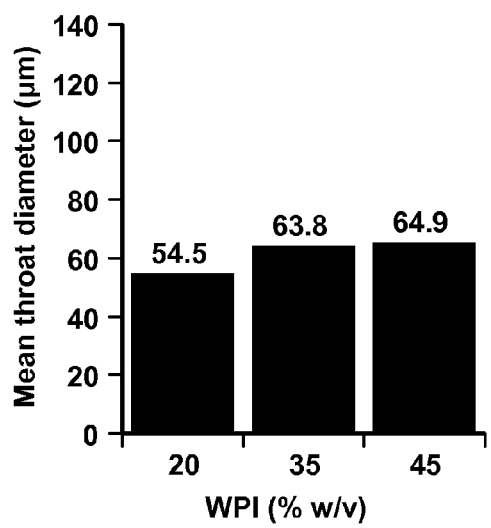

The pores in these scaffolds showed limited interconnectivity, as expressed by the pore coordination numbers (FIG. 28B), with the average coordination number observed in the 20WPI scaffold falsely high because of the inhomogeneity. In fact, the gel matrix exhibited higher interconnectivity with increased protein concentration. The concentration affected the inscribed pore diameters as well, but the differences in the mean pore size were relatively small—approximately 20 μm between each pair (FIG. 28C). However, because of the 20WPI scaffold irregularity, the mean pore diameters are falsely large. The effect is further clarified by examination of the pore size distributions (data not shown). The number of pores was highly influenced by WPI concentration, with relatively few pores found in the 20WPI sample. This trend was consistent with the overall porosity measurement. Also, the shape of the distribution varied with WPI concentration. For low WPI, the distribution was highly positively skewed, with pores smaller than 30 μm occurring most frequently. For the intermediate concentration, 35% w/v WPI, the distribution was much closer to Gaussian, while for high WPI, the distribution was once again positively skewed, but with most pores between 80 and 120 μm, and smaller pores less frequently observed. The latter distribution was also much wider, with a long tail, indicating a significant number of pores larger than 200 μm. The median pore sizes of the two porous scaffolds (35WPI and 45WPI) were almost equal, both approximately 100 μm. The average throat diameter—diameter of the inscribed connections between pores—appeared roughly independent of WPI concentration (FIG. 28D). The two porous samples, 35WPI and 45WPI showed almost identical average throat sizes, and the average throat size for 20WPI is not a meaningful quantity, due to the localization of the pores on one narrow section of the sample.

Figure 29A:
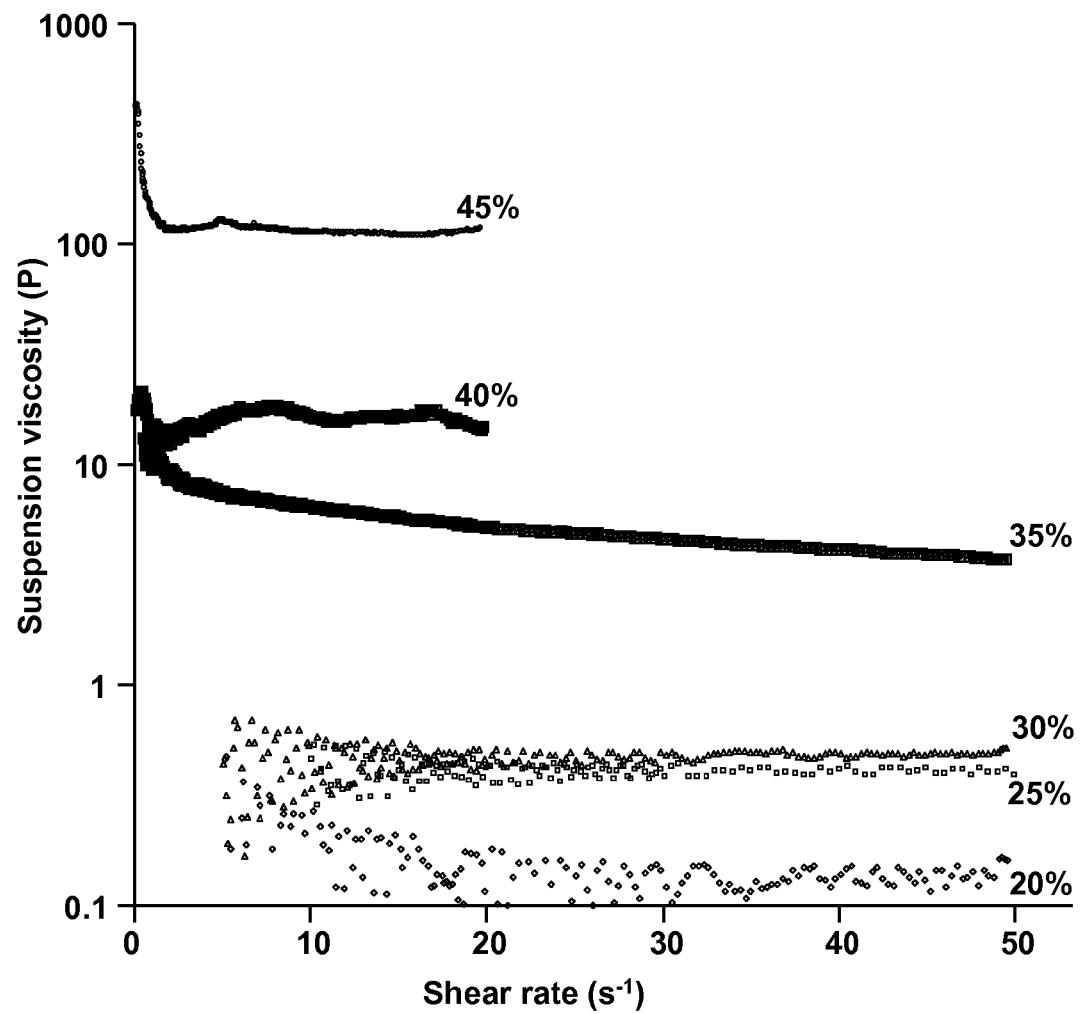
FIGS. 29A and 29B illustrate viscosity variation with WPI suspension concentration.
Figure 29B:
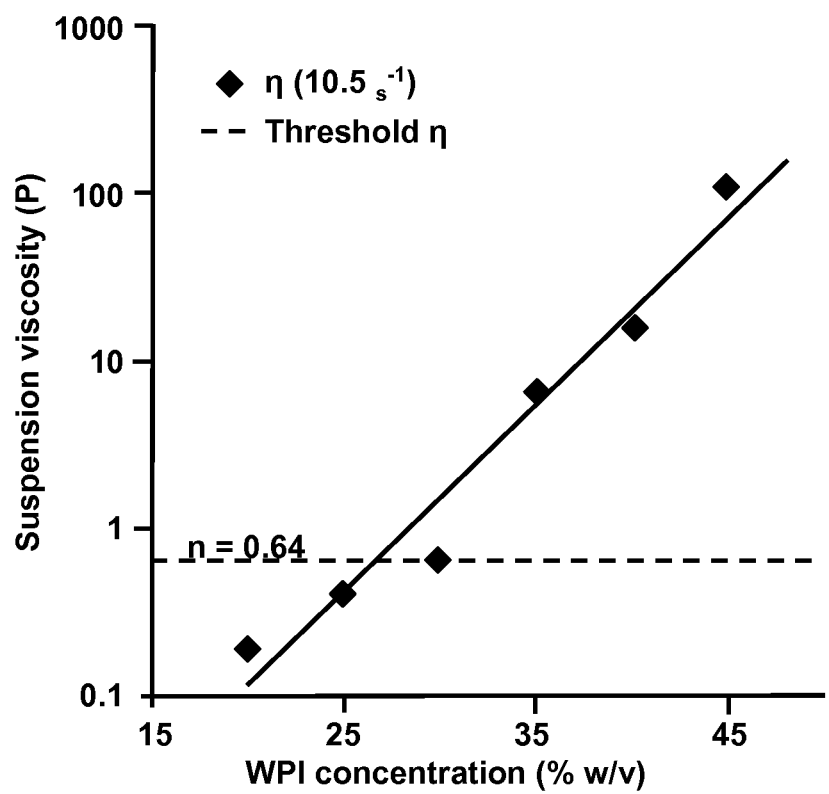

Results—Viscosity: WPI suspensions, subjected to processing identical to that used for gelation samples, were tested at various shear rates and the viscosities measured at shear rates appropriate for each suspension. The results are shown in FIGS. 29A and 29B. FIG. 29A shows the viscosities of six WPI suspensions (20%, 25%, 30%, 35%, 40% and 45% w/v WPI) measured over a range of shear rates; and FIG. 29B shows viscosities for a shear rate of 10.5 $s^{-1}$ using cone and plate configuration with the calculated threshold viscosity to support 100 μm bubbles indicated by the horizontal line. Of the six suspensions tested, the three more dilute suspensions exhibited Newtonian behavior, registering a constant viscosity with respect to shear rate. The three more concentrated suspensions demonstrated shear-thinning behavior, and a yield stress was observed for the two most concentrated suspensions, as typical of Bingham plastics. At a relatively low shear rate (averaged values between 10 and 11 $s^{-1}$), which is relevant to the analysis, the viscosity varied exponentially with WPI concentration, spanning almost three orders of magnitude (FIG. 28B). The pores in the gel matrix originate from air bubbles in the gel precursor suspension that remain trapped during the curing of the gel. Therefore the observed pore network characteristics stem primarily from the fluid properties of the suspension. Without wishing to be bound by this theory, we believe there exists a threshold viscosity that is necessary and sufficient to prevent bubbles of the median diameter (approximately 100 μm) from rising to the interface within the time required for the sample to become solid (approximately 10 min). Moreover, the value of the threshold viscosity lies between the measured viscosity of the 20% w/v WPI suspension and that of 35% w/v WPI.

For use in bone tissue regeneration, an optimal scaffold should contain high porosity (void volume of at least 80-90%), with pores that are highly interconnected, with most or all of the inner porosity accessible from the scaffold surface. The mean pore size should be at least 100 μm. Based on these criteria, an optimal scaffold using WPI could be made by incorporating more void volume into the matrix. This could be accomplished by porogen incorporation or foaming of the precursor suspension, since the suspensions can be made viscous enough to support large enough bubbles and the air-liquid interface is stable enough to allow for large interfacial area. However, without modification the pores of the WPI gels are sufficiently large to facilitate cell migration and survival. Modification of the process to produce higher porosity could also improve both throat diameters and interconnectivity.

The WPI gel pore network structure was found to depend heavily on WPI concentration in the gel precursor suspension. It was determined that a threshold WPI concentration was necessary to obtain any detectable pore content in the material. This threshold is between 20% and 35% w/v WPI, and is dictated primarily by the viscosity of the gel precursor suspension. Between 20%) and 35% w/v WPI, the suspension undergoes a shift from Newtonian to shear-thinning characteristics, and experiences a 33-fold increase in viscosity. The added suspension viscosity imparts a drag force great enough to trap large air bubbles introduced during suspension preparation that escape during gelation when the viscosity is lower.

Pore size distributions within the proper range for successful 3D cultures can be achieved for the porous gels (35% and 45% w/v WPI). Using the current processing technique, the highest porosity attained was 17.8%, which is below the optimal range for bone regeneration. Pore interconnectivity and inter-pore throat diameters were also found to be low for the application. Additional void volume could be readily incorporated by modifying the current scaffold fabrication technique.

EXAMPLE 8

Characteristics of WPI Films Produced by Electrospinning

Materials and methods. A method of electrospinning was developed for the whey protein isolate (WPI) and the non-woven mats created by the process were characterized. Whey protein isolate (WPI) powder (Davisco Foods International) containing 97.6% protein by weight was used as provided. Trifluoroacetic acid (TFA) (>98%) was purchased from Sigma-Aldrich. Solutions containing 0.30-0.60 g WPI/mL TFA were prepared in a well-vented fume hood by gradual addition of WPI to TFA and vortexed to mix in a 50 mL centrifuge tube. Each solution was loaded into a 5 mL polypropylene lock-tip syringe and fed through Tygon® R 3603 laboratory tubing, and out of a 38.1 mm (1.5 in), 18-gauge blunt-ended needle using a KDS 100 syringe pump (kd Scientific Inc., Holliston, Mass.). Electrospinning was performed in a custom apparatus constructed in-house. The needle was connected to a high-voltage source and placed in an adjustable, insulating stand orthogonally to a grounded copper collection plate. The needle and plate construct was encased in an insulated polycarbonate chamber. Operation variables were manipulated to determine the operational range and impact on the electrospun fibers. Flow rate was varied from 0.1 to 2.5 mL per hour; applied voltage was varied from 10 to 30 kV; and the distance between the needle and the collection plate was varied from 120 to 180 mm. Electrospun fibers were collected with forceps and stored in nitrogen in a sealed centrifuge tube covered in aluminum foil until characterized, to protect against changes due to light or oxygen. The electrospun fibers were sputter-coated with gold and viewed with a Cambridge Stereoscan 260 scanning electron microscope (SEM) at 4 kV. Micrographs of the fibers were used to compare fiber diameter, uniformity, and general appearance and to gauge the dependence of these properties on process variables. Image analysis for fiber diameters was performed using ImageJ for Microscopy software.

Figure 30:
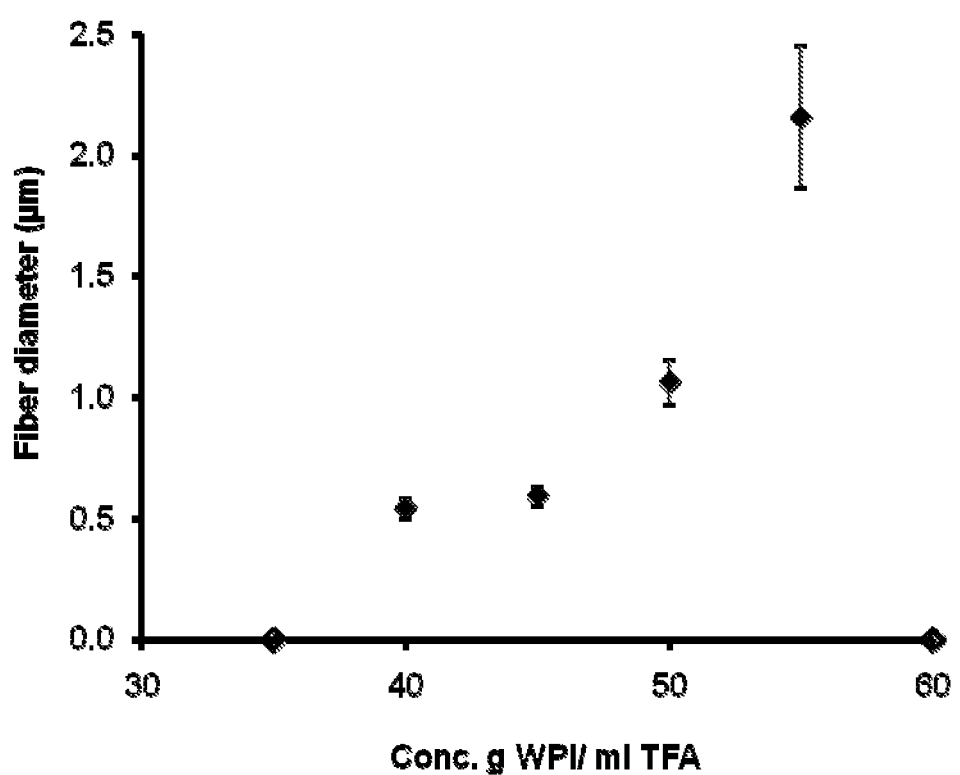
FIG. 30 illustrates the effect on electrospun fiber diameter with increasing protein concentration. The empty markers represent non-spinning solutions.

Results—Electrospinning Parameters. WPI solutions in TFA were able to be electrospun under a range of conditions. Since samples initially displayed good spinning characteristics at a voltage of 18.6 kV, a flow rate of 0.1 mL/hr, and a collector distance of 12 cm, these control parameters were used when varying WPI concentration. Protein content resulting in spinnable solutions ranged from 0.40 g WPI to 0.55 g WPI per mL TFA. FIG. 30 shows the change in electrospun fiber diameter with the amount of WPI. Increasing the protein concentration was found to increase fiber diameter fourfold across the range of spinnable solutions (FIG. 30). The change in concentration also affected beading in the sample, or the presence of nanobeads among the fully-formed fibers. This undesired phenomenon was observed in lessening degrees between 0.40 and 0.50 g WPI/mL TFA, then to a greater extent at 0.55 g WPI/mL TFA—the boundary of the spinnable range. Solutions of concentration above and below the tested range did not yield electrospun fibers. Outside the range the rheological properties of the spinning solutions were unsuitable for fiber formation.

Figure 31:
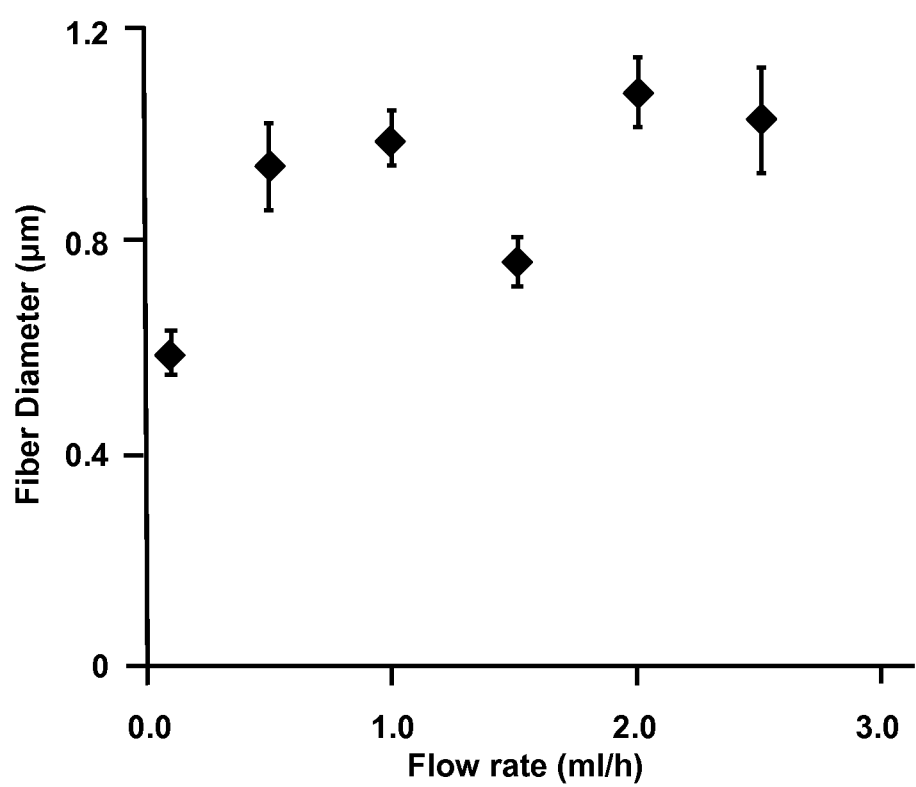
FIG. 31 illustrates the effect on electrospun fiber diameter with increasing solution flow rate.

Solutions of 0.45 g WPI/mL TFA were subjected to 18.6 kV with a collector distance of 120 mm to test the effects of the solution flow rate on the spinnability of the solution and resulting fiber diameters. FIG. 31 shows the effects of solution flow rate on the diameter of the electrospun fiber. Flow rates were varied from 0.1 mL/hr to 2.5 mL/hr. The data suggested a modest rise in fiber diameter between flow rates of 0.1 and 1.0 mL/hr, with roughly constant diameter between 1 and 2.5 mL/hr (FIG. 31).

Figure 32:
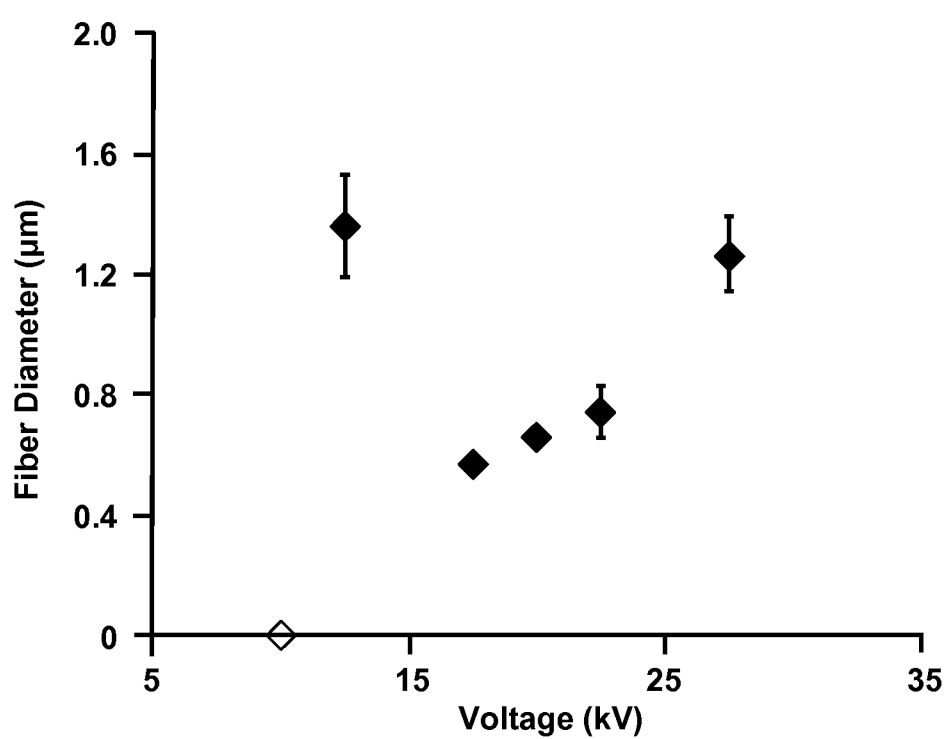
FIG. 32 illustrates the effect on electrospun fiber diameter with increasing voltage.
Figure 33:
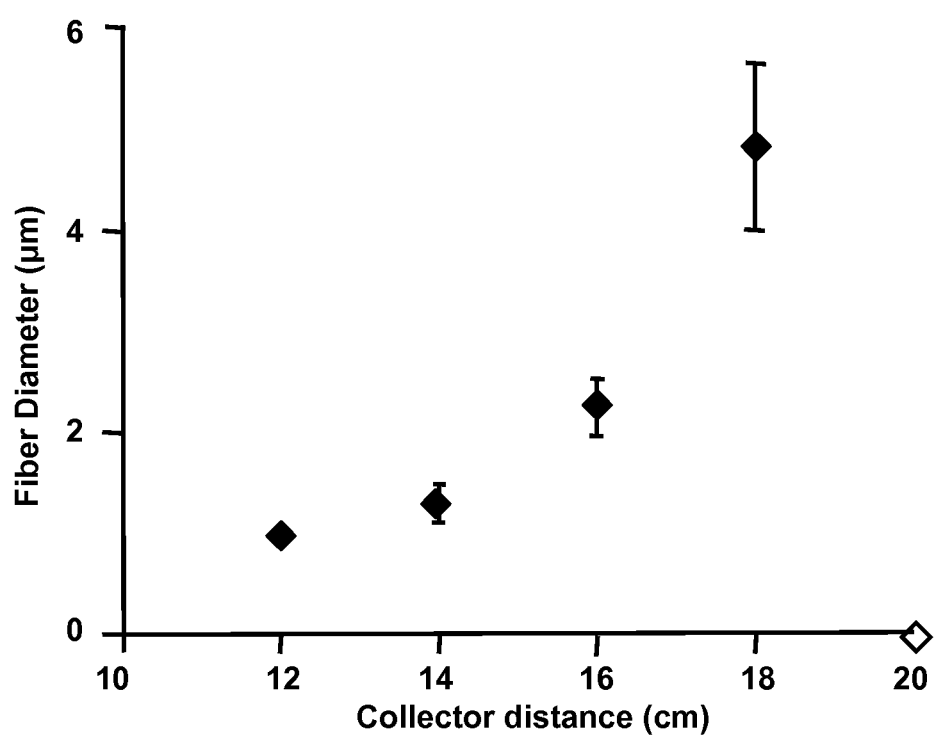
FIG. 33 illustrates the effect on electrospun fiber diameter with increasing collector plate distance from the needle tip. The empty marker indicates non-spinning distance.

To test the effect of voltage on the electrospun WPI fiber morphology and diameter, solutions of 0.45 g WPI/mL TFA were flowed at 0.5 ml. In for a distance of 120 mm towards the collection plate. Voltages between 0 and 30 kV were applied to the solutions. FIG. 32 shows the effect of applied voltage on the diameter of the electrospun fiber. The range allowing for successful electrospinning was between 12.5 and 27.5 kV. For most of the spinnable range of voltages, the fiber diameter was proportional to the voltage applied (FIG. 32). The exception occurred at the voltage corresponding to the onset of spinnability—12.5 kV. Scanning electron micrographs highlighting fiber morphology for the tested voltages were viewed. The fiber diameters resulting from 12.5 kV voltage were the largest in the range and appeared wavy and discontinuous (data not shown). The intermediate voltages were more suitable, forming longer, smooth, straight fibers. Additionally, as shown in FIG. 32, fiber diameter at 17.5 kV was less than half that for fibers spun at 12.5 kV. Branching of the fibers was observed throughout the range, with the intermediate voltages minimizing branching and resulting in the smoothest, most continuous strands. Overall, nanofibers as narrow as 150 nm were observed, corresponding to an applied voltage of 22.5 kV The effect of the vertical distance traversed by the fibers to reach the collection plate was tested by flowing WPI solutions of 0.45 g WPI/mL TFA at a rate of 0.5 mL/hr and applying 18.6 kV to the needle. The distance from the tip of the needle to the collection plate was varied from 120 to 200 mm. The results are shown in FIG. 33 which plots the diameter of the electrospun fibers against the collector distance. Electrospun fibers were formed for distances between 120 and 180 mm. Fiber diameter was a strong function of spinning distance; as the distance to the collection plate increased, fiber diameter increased (FIG. 33), but so did fiber branching as the smoothness of the fibers decreased.

A successful method of electrospinning never-before spun WPI has been established. WPI was fully dissolved in trifluoroacetic acid and electrospun into non-woven mats of fibers. The operating range for fiber formation was established, and fibers ranging in diameter from 150 to 4800 nm were created. This technique may be useful in making mats and scaffolds by ability to spin fibers of varying diameter and shape.

EXAMPLE 9

Attaining the Optimum Scaffold Pore Network

The current technique of electrospinning suffers a disadvantage in requiring the use of trifluoroacetic acid (TFA)—a toxic solvent—the removal of which must be exhaustive in order to enable spun scaffolds to come into contact with a biological environment. Either the development of a purification protocol or a technique to spin WPI in water or another benign solvent would be required. Additionally, the electrospun fibers are highly soluble in water as well as ethanol—an obstacle for use in an aqueous environment. It is believed that the fiber network can be cross-linked and rendered insoluble as seen for bovine serum albumin (BSA), which is the most water-soluble component of WPI. Aged BSA fibers have been found to lose their solubility. It is likely that the same can be achieved for WPI fibers and perhaps accelerated using a strong UV source. This possibility will be investigated to solve the solubility problem of electrospun WPI. It must be noted that if the challenges of electrospinning WPI can be addressed, it will still be necessary to combine it with a technique to incorporate macroporosity into the scaffold, since electrospun non-woven mats generally contain nanopores, but no pores on the order of hundreds of micrometers, as those necessary for a bone tissue scaffold.

A second possible method for increasing the overall porosity and interconnectivity of WPI scaffolds is a technique known as salt leaching. Many cases in the literature can be found where NaCl crystals of a specific size range were incorporated into a non-solvating, organic solution of the matrix polymer and served as place-holders for matrix pores. The salt was later dissolved with water, leaving behind an interconnected, high-void-volume network. Although NaCl cannot serve this function in an aqueous precursor suspension, a similar procedure may be employed if optimized. Sodium sulfate is almost water-insoluble at room temperature, but solubility increases by an order of magnitude at 32.4° C. This phenomenon may be employed to build porosity into WPI gels by incorporating microparticles of $Na_2SO_4$ into the precursor suspension, then dissolving the salt at 32.4° C. By characterizing the contribution of the salt particles and refining the process to yield the proper porosity, interconnectivity, and pore size, the procedure will be optimized to overcome the pore network limitations.

A third possible method to correct the observed pore network is a variation of gas foaming during gelation. Preliminary studies have shown that incorporation of ethanol and a small concentration of surfactant, such as Triton™ -X100, elicits a rapid foaming response during gelation at 80° C., due to the boiling of ethanol in the system. If the technique can be characterized and optimized to predictably achieve the proper porosity and pore size by controlling composition, this method can serve to overcome the current limitations.

EXAMPLE 10

Nanocomposite Design and Testing

The mechanical properties of the strongest composite formed were still insufficient for load-bearing applications of the material. The contribution of a nano-phase, crystalline, polysaccharide filler will be investigated. If other material combinations are an indication, the use of nanocrystalline cellulose or amylopectin will improve the composite mechanical properties, launching them into the range appropriate for withstanding normal stresses. Different fillers should be tested, as well as functionalization of the nanophase. Polysaccharide nanocrystals can be functionalized with primary amines or carboxylic acids, or even some sulfhydryl groups that would contribute to strong interfacial forces binding filler to protein matrix.

EXAMPLE 11

Degradation Studies

The success of an implantable bone regeneration scaffold hinges on its degradation properties and mechanism. The scaffold should clear the site of injury within a time period on the order of months. The degradation should not cause the material to lose load-bearing capacity prior to the formation of enough regenerating bone to take over the function. Also, the degradation products must be non-toxic, and should not accumulate in any organ. The degradation properties of WPI gels will be measured in the future as an important aspect of scaffold design.

EXAMPLE 12

3D Scaffold Testing

All cellular response experiments above were conducted in two dimensions—on a flat surface. Bone and the cells that comprise it have inherent three-dimensional characteristics, such as intercellular sensing, environmental sensing and response, and specific surface area considerations. Having established WPI gel as a viable growth surface, the next step will be to evaluate its behavior in three-dimensional culture. It is expected that the 3D structure will improve cellular growth and promote differentiation on the scaffold by providing additional environmental signaling.

EXAMPLE 13

Stem Cell Response

In vitro studies throughout this project used a model immortal cell line of osteoblast-like cells. The choice of cell line was common, and universally accepted as a useful preliminary indication of cell behavior. These tests will be followed with similar tests using stem cells as well as other suitable primary cell lines. These are the cells that will be responsible for osteogenesis in the implant environment. It is expected that the WPI scaffold will also be a good scaffold to support the growth, regeneration and differentiation of stem cells. In addition, growth factors and other compounds can be added to the WPI matrix to support growth and differentiation.

EXAMPLE 14

Immunogenicity Studies of WPI

Concerns have been raised in response regarding the immunogenicity of WPI, which would prevent its effective use in vivo. However, gels made with WPI were found to be non-cytotoxic, and promoted the adhesion and long-term proliferation of osteoblast cells. This behavior, however, is independent of the possible response in the presence of cells controlling the immune response. A study was done with WPI-PEG mixed gels implanted subcutaneously in mice, showing that immunogenicity is not a concern for up to 60 days [30]. This supports the assertion that current processing methods remove immunogenic recognition factors from the network, but a similar study will be conducted to provide proof of the material biocompatibility. Because the implant environment can only be reproduced to a degree in vitro, in vivo testing cannot be avoided. Bone formation with or without preseeding and preculturing of cells in WPI gels at different lengths of time will be measured to show the suitability of WPI scaffolds. Given the pronounced breakdown of tertiary structure of the proteins of WPI during processing and the WPI-PEG in vivo compatibility [30], it is expected that the WPI gels will be biocompatible.

EXAMPLE 14

Other Applications for WPI Hydrogels

The properties of WPI gels were found to vary widely with composition and processing. This versatility is useful for applications other than the one explored here. Other uses of WPI hydrogels include without limitation wound-dressing, regeneration scaffold of other tissues (e.g., skin, cartilage or connective tissue), controlled releases of drugs or small molecules, biodegradable fishing lures, for electrospun non-woven mats, chemical sensor or biosensor, or as an environmentally benign, economically favorable column packing material. WPI as an abundant, inexpensive natural material, possesses many attractive characteristics.

EXAMPLE 15

Preparation of Fishing Lure Samples

To hone in on the optimum material properties, lure samples of varying compositions were prepared. The concentration of WPI was varied from 20% to 35% wt/volume. $CaCl_2$, was varied from 0 to 20 mM. Amylose was varied between 0 and 0.10 g/g WPI. The suspensions were homogenized using a hand mixer and loaded into three molds for lure shapes. The samples were cured at 80° C. in a heated press for a curing time between 10 and 30 minutes. At the end of curing, the samples were firm and rubbery and could be torn by hand. When hydrated (as when freshly prepared or kept in a moist environment), they were flexible enough to be bent 180 degrees without fracturing. The mechanical properties have not been quantified, but the composition of samples best approaching the desired texture is close to 25% wt in water (no $CaCl_2$). Degradation kinetics are not known, but expected to be on the order of weeks to months without the aid of enzymatic hydrolysis.

Without wishing to be bound by this theory, it is believed that the use of NaCl, from about 0 mM to about 100 mM, instead of $CaCl_2$ may be a better option for the texture of fishing lures. Sodium ions do not interact as strongly with WPI amino groups as do calcium ions. A sodium network is therefore more fine-stranded and continuous instead of aggregates as seen using calcium ions. The resulting sodium gel would have lower firmness than with calcium chloride. In addition, the range of NaCl is broader than the range of $CaCl_2$, up to 100 mM for NaCl as compared to 10 mM for $CaCl_2$. This allows more flexibility and control in fabrication of the lures. Samples were made with 25-35% WPI and up to 100 mM NaCl at cure times between 10 and 30 min. The optimal conditions appeared to be about 28% WPI, and 5-15 mM NaCl. The resultant gel showed a more continuous, less globular structure. The "lure" was translucent, less firm, and more flexible than the $CaCl_2$ gel described above, but still showed similar strength in tension. Overall, the lure showed significantly higher elasticity and a more "rubber-like" feel and texture.

EXAMPLE 16

Addition of Compounds to WPI Hydrogels

The WPI hydrogels can also be used to incorporate various compounds, including drugs and other therapeutic compounds, and slowly release the compounds over time. To make the initial WPI mixture, the desired amount of a salt solution (Ca or Na salt) at the desired concentration will be measured. The desired concentration of WPI will be added to the salt solution, and the solution will be mixed thoroughly, e.g., by vortex or stirring. The desired amount of amino acid crystals will be folded into the solution, and gently stirred for only a few seconds so that crystals are maintained. The solution with crystals will be poured into molds and thermally cured. The cured hydrogel will be tested for time of release of dissolved amino acids and time to degradation of the hydrogel.

EXAMPLE 17

Addition of Individual WPI Components

To test the effect of the individual WPI components on the hydrogel consistency, various amounts of β-lactoglobulin, α-lactalbumin, or bovine serum albumin will be added to the WPI mixture prior to curing. The range of addition to be tested will be beta-lactoglobulin: up to 2× the amount already present in WPI; alpha-lactalbumin: up to 5× the amount already present in WPI; and bovine serum albumin: up 5× the amount already present in WPI. The mixtures will be vortexed thoroughly before pouring into molds for curing. After curing, the hydrogels will be compared for strength and degradation time. It is expected that increasing ratio of β-lactoglobulin to other components will make the WPI hydrogel stronger and more rigid.

EXAMPLE 18

WPI Hydrogels with Glycerol

WPI hydrogels were produced using WPI (20-45 wt %) and with 10 mM calcium chloride using varying mixtures of glycerol and water. The glycerol:water ratios tested were 0:1 (0% glycerol, 100% water), 1:3 (25% glycerol, 75% water), 1:1 (50% glycerol, 50% water), 3:1 (75% glycerol, 25% water), and 1:0 (100% glycerol, 0% water). The samples were mixed with an immersion mixer until the sample was visually homogenous and then cast and heated to 80° C. for 30 minutes. The resulting hydrogels visually had properties that were indistinguishable from each other. However, the samples containing glycerol increased in flexibility with increasing glycerol concentration. The flexibility was determined using a benchtop two-point bending test with a constant mass applied at the center of the sample, and using the level of deflection qualitatively to indicate flexibility.

After processing and flexion testing, the samples were divided into two sets for cell growth analysis as compared to a control (plasma treated tissue culture flask) and for drying analysis. The samples used for cell growth were seeded with 10,000 MC3T3-E1 preosteoblasts and placed in growth media as described above for 48, 72, and 96 hours. Microscope examination of the scaffolds showed no discernable difference in cell growth on any of the scaffolds and the control. Thus the addition of glycerol did not change the cell growth kinetics.

The samples used to analyze the stability of the gel hydration were placed in a sterile environment (BSL II biological safety cabinet) for a time period of up to 6 months. A sample was removed and observed for hydration and flexibility every month. Visually, the samples containing glycerol showed no change over the 6 month study period. In contrast, the water-only sample showed a significant loss in dimension due to water loss for all samples during the study. Additionally, the water-only samples appeared to lose all removable water (as some water is likely to remain trapped in the scaffold for a significant amount of time) within the first month, with no discernable change in sample properties after the first month. The water-only samples were very stiff and showed no flexibility after the first month of aging, as analyzed using the two-point bending analysis described above. The glycerol samples showed no discernable loss of dimension during the drying process for any sample tested. The two-point bending analysis confirmed this result and the glycerol samples showed no appreciable change in flexibility over the entire 6 month study.

The glycerol-containing gels showed at least two advantages over WPI gels with no glycerol: the gels containing glycerol had higher flexibility, and the gels maintain their hydrated state for a substantially longer period of time (greater than 6 months) when glycerol is incorporated in the matrix in quantities equal to or greater than that of water. There were no significant changes in processing of the gel as glycerol shows similar solvent properties to water. The glycerol/water WPI gels are useful for producing fully biodegradable fishing lures in addition to use as scaffolds or mats for more flexible tissues, particularly cartilage and skin. A potential composition for a flexible, biodegradable fishing lure would be 20-45% WPI, 0-25 mM salt, and glycerol in a concentration ≥ 25%. The composition that would be preferred for use in tissue scaffolds for non-bone tissue is 20-45% WPI, 0-25 mM salt (preferred calcium chloride), and glycerol in a concentration ≥ 20%. To either the fishing lure or the tissue scaffold could be added compounds to make the structure more useable, including but not limited to, cellulose, amylose, amylopectin, glycogen, dextran, other polysaccharides, and polymers.

REFERENCES

[1] Goldstein S A, Wilson D L, Sonstegard D A, Matthews L S. The mechanical properties of human tibial trabecular bone as a function of metaphyseal location. Journal of Biomechanics. 1983; 16:965-9.

[2] Yaszemski M J, Payne R G, Hayes W C, Langer R, Mikos A G. In vitro degradation of a poly(propylene fumarate)-based composite material. Biomaterials. 1996; 17:2127-30.

[3] Murugan R, Ramakrisbna S. Nano-featured scaffolds for tissue engineering: A review of spinning methodologies. Tissue Engineering. 2006; 12:435-47.

[4] Shin H, Jo S, Mikos A G. Biomimetic materials for tissue engineering. Biomaterials. 2003; 24:4353-64.

[5] Drury J L, Mooney D J. Hydrogels for tissue engineering: scaffold design variables and applications, Biomaterials, 2003; 24:4337-51.

[6] Kanungo B P, Silva E, Vliet K V, Gibson L J, Characterization of mineralized collagen-glycosaminoglycan scaffolds for bone regeneration, Acta Biomaterialia. 2008; 4:490-503.

[7] Drury J L, Mooney D J. Hydrogels for tissue engineering: scaffold design variables and applications. Biomaterials. 2003; 24:4337-51,

[8] Kinselia J E, Whitehead D M. Proteins in whey: chemical, physical, and functional properties. Advances in Food and Nutrition Research. 1989; 33:343-438.

[9] Fox P F. Milk proteins as food ingredients. International Journal of Dairy Technology, 2001; 54:41-55.

[10] Vardhanabhuti B, Foegeding E A, Rheological properties and characterization of polymerized whey protein isolates. Journal of Agricultural and Food Chemistry. 1999; 47:3649-55.

[11] Marangoni A G, Barbut S, McGauley S E, Marcone M, Narine S. On the structure of particulate gels—the case of salt-induced cold gelation of heat-denatured whey protein isolate. Food Hydrocolloids. 2000; 14:61-74.

[12] Walzem R L, Dillard C J, German J B, Whey components: Millennia of evolution create functionalities for mammalian nutrition: What we know and what we may be overlooking. Critical Reviews in Food Science & Nutrition. 2002; 42:353,

[13] Laurencin C T, Attawia M A, Elgendy H E, Herbert K M. Tissue engineered bone-regeneration using degradable polymers: The formation of mineralized matrices. Bone. 1996; 19:S93-S9.

[14] Kato K, Toba Y, Matsuyama H, Yamamura I, Matsuoka Y, Kawakami H, et al. Milk basic protein enhances the bone strength in ovariectomized rats. Journal of Food Biochemistry. 2000; 24:467-76.

[15] Takada Y, Aoe S, Kumegawa M. Whey protein stimulates the proliferation and differentiation of osteoblastic MC3T3-E1 cells. Biochemical and Biophysical Research Communications. 1996; 223:445-9.

[16] Uenishi K, Ishida H, Toba Y, Aoe S, Itabashi A, Takada Y. Milk basic protein increases bone mineral density and improves bone metabolism in healthy young women. Osteoporosis International. 2007; 18:385-90.

[17] Takada Y, Kobayashi N, Matsuyama H, Kato K, Yamamura J, Yahiro M, et al. Whey protein suppresses the osteoclast-mediated bone resorption and osteoclast cell formation. International Dairy Journal. 1997; 7:821-5.

[18] Bryant C M, McClements D J. Influence of xanthan gum on physical characteristics of heat-denatured whey protein solutions and gels. Food Hydrocolloids. 2000; 14:383-90.

[19] Ostojić S, Pavlović M, Živić M, Filipović Z, Gorjanović S, Hranisavljević S, et al. Processing of whey from dairy industry waste. Environmental Chemistry Letters, 2005; 3:29-32.

[20] Mockaitis G, Ratusznei S M, Rodrigues J A D, Zaiat M, Foresti E. Anaerobic whey treatment by a stirred sequencing batch reactor (ASBR): effects of organic loading and supplemented alkalinity. Journal of Environmental Management. 2006; 79:198-206.

[21] Teo J Y. Beitle R. Novel solvent stable micro-porous membrane made of whey protein isolate gel. Journal of Membrane Science. 2001; 192:71-82.

[22] Kuwata K, Hoshino M, Forge V, Era S, Batt C A, Goto Y. Solution structure and dynamics of bovine beta-lactoglobulin A. Protein Science. 1999; 8:2541-5.

[23] Chrysina E D, Brew K, Acharya K R. Crystal structures of apo- and holo-hovine alpha-lactalbumin at 2.2-A resolution reveal an effect of calcium on inter-lobe interactions. Journal of Biological Chemistry. 2000; 275:37021-9.

[24] Foegeding E A, Davis J P, Doucet D, McGuffey M K. Advances in modifying and understanding whey protein functionality. Trends in Food Science & Technology, 2002; 13:151-9.
[25] Patocka G, Cervenkova R, Narine S, Jelen P, Rheological behaviour of dairy products as affected by soluble whey protein isolate. International Dairy Journal. 2006; 16:399-405.
[26] Vardhanabhuti B, Foegeding E A. Rheological properties and characterization of polymerized whey protein isolates. Journal of Agricultural and Food Chemistry. 1999; 47:3649-55.
[27] van den Berg L, van Vliet T, van der Linden E, van Boekel MAJS, van de Velde F, Breakdown properties and sensory perception of whey proteins/polysaccharide mixed gels as a function of microstructure. Food Hydrocolloids. 2007; 21:961-76.
[28] Mulvihill D M, Kinsella J E. Gelation of beta-lactoglobulin—effects of sodium-chloride and calcium-chloride on the rheological and structural properties of gels. Journal of Food Science. 1988; 53:231-6,
[29] Kuhn P R, Foegeding E A. Mineral salt effects on whey-protein gelation. Journal of Agricultural and Food Chemistry. 1991; 39:1013-6.
[30] Rouabhia M, Gilbert V, Wang H X. Subirade M. In vivo evaluation of whey protein-based biofilms as scaffolds for cutaneous cell cultures and biomedical applications. Biomedical Materials. 2007; 2:S38-S44.
[31] Ju Z Y, Kilara A. Gelation of pH-aggregated whey protein isolate solution induced by heat, protease, calcium salt, and acidulant. Journal of Agricultural and Food Chemistry. 1998; 46:46 (5) 1830-5,
[32] Kinekawa Y-I, Fuyuki T, Kitabatake N, Effects of salts on the properties of sols and gels prepared from whey protein isolate and process whey protein. Journal of Dairy Science. 1998; 81:1532-44.
[33] Hussain F, Hojjati M, Okamoto M, Gorga R E. Review article: Polymer-matrix nanocomposites, processing, manufacturing, and application: An overview, Journal of Composite Materials, 2006; 40:1511-75.
[34] Grunert M, Winter W T. Nanocomposites of cellulose acetate butyrate reinforced, with cellulose nanocrystals. Journal of Polymers and the Environment. 2002; 10:27-30.
[35] Cao X, Dong H, Li C M, New nanocomposite materials reinforced with flax cellulose nanocrystals in waterborne polyurethane. Biomacromolecules. 2007; 8:899-904.
[36] Goldstein A S, Juarez T M, Helmke C D, Gustin M C, Mikos A G. Effect of convection on osteoblastic cell growth and function in biodegradable polymer foam scaffolds. Biomaterials. 2001; 22:1279-88.
[37] Ju Z Y, Kilara A. Properties of gels induced by heat, protease, calcium salt, and acidulant from calcium ion-aggregated whey protein isolate. Journal of Dairy Science. 1998; 81:1236-43,
[38] Caussin F, Framelart M H, Maubois X L, Bouhallab S, Mineral modulation of thermal aggregation and gelation of whey proteins: from beta-lactoglobulin model system to whey protein isolate, Lait. 2003; 83:1-12,
[39] Liu C, Xia Z, Czernuszka J T. Design and development of three-dimensional scaffolds for tissue engineering. Chem Eng Res Design 2007; 85:1051-1064.
[40] Chung H J, Park T G. Surface engineered and drug releasing pre-fabricated scaffolds for tissue engineering. Advanced Drug Delivery Reviews 2007; 59:249-262,
[41] Hutmacher D W, Scaffolds in tissue engineering bone and cartilage. Biomaterials 2000; 21:2529-2543.
[42] Lee S H, Shin H. Matrices and scaffolds for delivery of bioactive molecules in bone and cartilage tissue engineering. Advanced Drug Delivery Reviews 2007; 59:339-359.
[43] Ju Z Y, Kilara A. Aggregation induced by calcium chloride and subsequent thermal gelation of whey protein isolate. J. Dairy Sci 1998; 81:925-931,
[44] Ju Z Y, Hettiarachchy N, Kilara A. Thermal properties of whey protein aggregates. J Dairy Sci 1999; 82:1882-1889.
[45] ASTM Standard D 638-97, Standard test method for tensile property of plastics. Annual Book of ASTM Standards. West Conshonocken, Pa., USA: ASTM International; 1998; pp. 46-58.

The complete disclosures of all references cited in this specification are hereby incorporated by reference. Also incorporated by reference are the complete disclosures of the following: Mia Dvora, "Designing a whey protein based material as a scaffold for bone regeneration," a thesis submitted to Louisiana State University, August 2010; Mia Dvora and James E. Henry, "Altering the Mechanical Properties of Protein-Based Solids", 2006 AIChE (American Institute of Chemical Engineers) Annual Meeting, San Francisco, Calif., Nov. 12-17, 2007; Mia Dvora, Allen Reed, Karsten Thompson, and James E. Henry, "X-Ray tomography for analysis of biological scaffold materials," an abstract and presentation given at the 2007 AIChE (American Institute of Chemical Engineers) Annual Meeting, Salt Lake City, Utah, Nov. 4-9, 2007; Mia Dvora and James E. Henry, "Characterization of whey protein isolate sol-gels as scaffolds for bone regeneration," an abstract and presentation given to the 2007 AIChE Annual Meeting, Salt Lake City, Utah, Nov. 4-9, 2007; Mia Dvora and James E. Henry, "Design of a whey protein isolate composite as a bone regeneration scaffold: optimization of mechanical properties," an abstract and poster given at the 2008 International Symposium on Polymer Physics, Xiamen, China, Jun. 8-12, 2008; Mia Dvora and James E. Henry, "Optimization of preosteoblast proliferation rate on whey protein gels for bone tissue regeneration," an abstract and presentation given to the 2008 AIChE Annual Meeting, Philadelphia, Pa., Nov. 16-21, 2008; and Mia Dvora and James E. Henry, "Whey protein isolate sol-gel as a scaffold for bone tissue regeneration: investigating the osteoprogenitor response," and "Whey protein isolate sol-gel as a scaffold for bone tissue regeneration", two abstracts and posters given at the 2009 American Chemical Society Annual Meeting, Washington, D.C., Aug. 16-20, 2009. In the event of an otherwise irreconcilable conflict, however, the present specification shall control.

What is claimed:

1. A fishing lure comprising a hydrogel; wherein said hydrogel comprises a mixture of a first component, a second component, a third component, and a fourth component; wherein said first component comprises whey protein isolate; wherein said second component comprises amylopectin, amylose, or both; wherein said third component comprises calcium chloride, sodium chloride, or both; and wherein said fourth component comprises water, glycerol, or both; wherein said hydrogel contains no collagen; and wherein said fishing lure is configured into any shape or design capable of attracting fish.

2. The lure as in claim 1, wherein the concentration of whey protein isolate is from 25% to 45% wt/v.

3. The lure as in claim 1, wherein the concentration of whey protein isolate is from 30% to 40% wt/v.

4. The lure as in claim 1, wherein the lure is biodegradable.

5. The lure as in claim 1, wherein said mixture additionally comprises one or more compounds selected from the group consisting of chitosan, alginate, chondroitan, fibrin, hyaluronic acid, gelatin, poly(ethylene) glycol, poly(lactic acid) poly(glycolic) acid, poly(lactic-co-glycolic acid), poly (ether ketone), poly($\epsilon$-caprolactone), poly(alpha-hydroxyester)s, and polyglycolide.

6. The lure as in claim 1, wherein said fourth component comprises glycerol.

7. The lure as in claim 1, wherein said second component comprises amylopectin.

8. The lure as in claim 7, wherein the concentration of amylopectin is from 5% to 15% w/w.

9. The lure as in claim 1, wherein said mixture additionally comprises one or more fish attractants selected from the group consisting of proteins other than collagen, amino acids, fish extracts not containing collagen, vertebrate blood, and other vertebrate extracts not containing collagen.

10. The lure as in claim 1, wherein said third component comprises sodium chloride.

11. The lure as in claim 1, wherein said third component comprises calcium chloride.

12. The lure as in claim 11, wherein the concentration of said calcium chloride is from 5 mM to 20 mM.

13. The lure as in claim 1, wherein said second component comprises amylopectin or amylose; and wherein said third component comprises calcium chloride or sodium chloride.

* * * * *

SEQUENCE LISTING

<160> NUMBER OF SEQ ID NOS: 3

<210> SEQ ID NO 1
<211> LENGTH: 5
<212> TYPE: PRT
<213> ORGANISM: Homo sapiens

```
<400> SEQUENCE: 1

Ile Lys Val Ala Val
1               5

<210> SEQ ID NO 2
<211> LENGTH: 5
<212> TYPE: PRT
<213> ORGANISM: Homo sapiens

<400> SEQUENCE: 2

Tyr Ile Gly Ser Arg
1               5

<210> SEQ ID NO 3
<211> LENGTH: 12
<212> TYPE: PRT
<213> ORGANISM: Homo sapiens

<400> SEQUENCE: 3

Arg Asn Ala Ile Ala Ala Glu Ile Ile Lys Asp Ile
1               5                   10
```